US011024429B2

(12) United States Patent
Patek et al.

(10) Patent No.: US 11,024,429 B2
(45) Date of Patent: Jun. 1, 2021

(54) METHOD, SYSTEM AND COMPUTER READABLE MEDIUM FOR ADAPTIVE AND ADVISORY CONTROL OF DIABETES

(75) Inventors: Stephen D. Patek, Charlottesville, VA (US); Boris P. Kovatchev, Charlottesville, VA (US)

(73) Assignee: UNIVERSITY OF VIRGINIA PATENT FOUNDATION, Charlottesville, VA (US)

( * ) Notice: Subject to any disclaimer, the term of this patent is extended or adjusted under 35 U.S.C. 154(b) by 1027 days.

(21) Appl. No.: 14/241,383

(22) PCT Filed: Aug. 26, 2012

(86) PCT No.: PCT/US2012/052422
§ 371 (c)(1),
(2), (4) Date: Mar. 9, 2015

(87) PCT Pub. No.: WO2013/032965
PCT Pub. Date: Mar. 7, 2013

(65) Prior Publication Data
US 2015/0190098 A1     Jul. 9, 2015

Related U.S. Application Data

(60) Provisional application No. 61/528,129, filed on Aug. 26, 2011.

(51) Int. Cl.
G16H 50/50     (2018.01)
A61B 5/00      (2006.01)
A61B 5/145     (2006.01)
A61M 5/168     (2006.01)
A61M 5/172     (2006.01)
G16H 50/30     (2018.01)
G16H 20/17     (2018.01)
G16H 20/30     (2018.01)
A61B 5/11      (2006.01)

(52) U.S. Cl.
CPC ............ *G16H 50/50* (2018.01); *A61B 5/002* (2013.01); *A61B 5/0022* (2013.01); *A61B 5/1118* (2013.01); *A61B 5/14532* (2013.01); *A61B 5/486* (2013.01); *A61B 5/4812* (2013.01); *A61B 5/4839* (2013.01); *A61B 5/4848* (2013.01); *A61B 5/4857* (2013.01); *A61B 5/4866* (2013.01); *A61B 5/7225* (2013.01); *A61B 5/7275* (2013.01); *A61B 5/7278* (2013.01); *A61B 5/7282* (2013.01); *A61B 5/743* (2013.01); *A61B 5/7475* (2013.01); *A61M 5/16886* (2013.01); *A61M 5/1723* (2013.01); *A61B 2505/07* (2013.01); *A61B 2560/0295* (2013.01); *A61B 2560/0475* (2013.01); *G16H 20/17* (2018.01); *G16H 20/30* (2018.01); *G16H 50/30* (2018.01)

(58) Field of Classification Search
None
See application file for complete search history.

(56) References Cited

U.S. PATENT DOCUMENTS

| 6,923,763 B1 | 8/2005 | Kovatchev et al. |
| 7,523,004 B2 | 4/2009 | Bartkowiak et al. |
| 2009/0006061 A1 | 1/2009 | Thukral et al. |
| 2015/0190098 A1 | 7/2015 | Patek et al. |

FOREIGN PATENT DOCUMENTS

| EP | 2748747 A1 | 7/2014 |
| WO | 0224065 A1 | 3/2005 |
| WO | 2008157780 A1 | 12/2008 |
| WO | 2009059187 A1 | 5/2009 |
| WO | 2013032965 A1 | 3/2013 |

OTHER PUBLICATIONS

Lalo Magni et al: "Model Predictive Control of Type 1 Diabetes: An in Silico Trial", Journal of Diabetes Science and Technology, vol. 1, No. 6, Nov. 1, 2007 (Nov. 1, 2007), pp. 804-812.
Cobelli C et al: "Diabetes: Models, Signals, and Control", IEEE Reviews in Biomedical Engineering, IEEE, USA, vol. 2, Jan. 1, 2009 (Jan. 1, 2009), pp. 54-96.
L Magni et al: "Model Predictive Control of Type 1 Diabetes added to Conventional Therapy", Preprints of the 18th IFAC World Congress, Aug. 28, 2011 (Aug. 28, 2011), pp. 7108-7113.
Office Action (Communication) dated Jul. 2, 2018, by the European Patent Office in corresponding European Patent Application No. 12 826 8232. (4 pages).
Canadian Office Action dated Mar. 26, 2019, by the Canadian Patent Office in corresponding Canadian Patent Application No. 2,846,854. (5 pages).
Office Action dated Apr. 1, 2020, by the Canadian Patent Office in corresponding Canadian Patent Application No. 2,846,854. (4 pages).
The extended European Search Report dated Mar. 1, 2021, by the European Patent Office in corresponding European Application No. 20191889.3. (10 pages).
Office Action dated Mar. 17, 2021, by the Canadian Patent Office in corresponding Canadian Patent Application No. 2,846,854. (3 pages).

*Primary Examiner* — Lori A. Clow
(74) *Attorney, Agent, or Firm* — Buchanan Ingersoll & Rooney PC; Robert J. Decker

(57) ABSTRACT

An Adaptive Advisory Control (AA Control) interactive process involving algorithm-based assessment and communication of physiologic and behavioral parameters and patterns assists patients with diabetes with the optimization of their glycemic control. The method and system may uses all available sources of information about the patient; (i) EO Data (e.g. self-monitoring of blood glucose (SMBG) and CMG), (ii) Insulin Data (e.g. insulin pump log files or patient treatment records), and (iii) Patient Self Reporting Data (e.g. self treatment behaviors, meals, and exercise) to: retroactively assess the risk of hypoglycemia, retroactively assess risk-based reduction of insulin delivery, and then report to the patient how a risk-based insulin reduction system would have acted consistently to prevent hypoglycemia.

99 Claims, 16 Drawing Sheets

METHOD, SYSTEM AND COMPUTER READABLE MEDIUM FOR ADAPTIVE AND ADVISORY CONTROL OF DIABETES

RELATED APPLICATIONS

The present application claims priority from U.S. Provisional Application Ser. No. 61/528,129 filed Aug. 26, 2011, entitled "Method, System and Computer Program Product for Adaptive Advisory Control of Diabetes," the disclosure of which is hereby incorporated by reference herein in its entirety.

GOVERNMENT RIGHTS

This invention was made with government support under Grant No. DK085623 awarded by The National Institutes of Health, and Grant No. 0931633 awarded by The National Science Foundation. The government has certain rights in the invention.

BACKGROUND OF THE INVENTION

In health, glucose metabolism is tightly controlled by a hormonal network including the gut, the liver, the pancreas, and the brain to ensure stable fasting blood glucose (BG) levels and transient postprandial glucose fluctuations. In Type 1 Diabetes Mellitus (T1DM), intensive insulin treatment attempting to approximate near-normal levels of glycemia markedly reduces chronic complications [49,61], but may risk potentially life-threatening severe hypoglycemia (SH)—a result from imperfect insulin replacement [25,60]. Consequently hypoglycemia has been identified as the primary barrier to optimal diabetes management [15,17]. Thus, people with T1DM face a life-long behaviorally-controlled optimization problem: to maintain strict glycemic control without increasing their risk for hypoglycemia [14]. Glucose variability, or the magnitude and the speed of BG fluctuations, is both the measurable result from this behavioral optimization and the principal feedback to the patient for his/her optimization of diabetes control. In other words, BG fluctuations in diabetes result from the action of a complex dynamical system perturbed by a behavioral event generator and dependent on two metabolic processes: (i) interaction between exogenous insulin and carbohydrate utilization and (ii) hormonal defenses against hypoglycemia known as counterregulation.

Approached from a systems biology point of view, the bio-behavioral control of T1DM is therefore comprised of: (i) behaviorally-triggered processes of commonly stable glucose fluctuations (e.g. regular postprandial glucose excursions) interrupted by generally random hypoglycemia-triggering behavioral events (e.g. insulin overdose, missed food, or excessive exercise [9,26]); and (ii) physiologic processes depending on a person's metabolic parameters such as insulin sensitivity [4] or counterregulation, which counteracts insulin-induced hypoglycemia, but also suffers from occasional depletion of counterregulatory reserves occurring with repeated hypoglycemia and known as hypoglycemia-associated autonomic failure (HAAF, [16]).

Attempts to use technology aiding the control of diabetes led to the formulation of the artificial pancreas idea, which can be traced back to developments that took place over thirty years ago when the possibility for external BG regulation in people with diabetes had been established by studies using intravenous (i.v.) glucose measurement and i.v. infusion of glucose and insulin. Systems such as the Bio-stator™ have been introduced and used in hospital setting to maintain normoglycemia by exerting both positive (via glucose or glucagon) and negative (via insulin) control [1,10,39,48,53]. Detailed description of the major early designs can be found in [6,11,13,21,22,52]. More work followed, spanning a broader range of BG control techniques, such as adaptive control [7,23], physiologic modeling [52,56], control specific to intensive care units [3], or linear quadratic Gaussian optimization (LQG) [24,41]. However, i.v. closed-loop control remains cumbersome and unsuited for outpatient use. An alternative to extracorporeal i.v. control has been presented by implantable i.v.-i.p. systems employing intravenous sampling and intra-peritoneal (i.p.) insulin delivery [37,51,55]. The implementation of these systems, however, requires considerable surgery. Thus, with the advent of minimally-invasive subcutaneous (s.c.) continuous glucose monitoring (CGM), increasing academic, industrial, and political effort has been focused on the development of s.c.-s.c. systems, using CGM coupled with insulin infusion pump and a control algorithm [2,8,29,31]. So far, encouraging pilot results have been reported [12,28, 54,58,62]. The pioneering studies of Hovorka et al. [27,28, 29] and Steil et al. [58] have outlined the two major types of controllers deemed suitable for s.c. use—MPC (model-predictive control) and PID (proportional-integral-derivative) control, respectively. To date, the first trials of fully s.c.-s.c. systems have been exclusively using PID [58,62]; nevertheless, MPC [20,27,38,45] became the approach of choice targeted by recent research [12,28,54]. There are two important reasons making MPC preferable: (i) PID is purely reactive, responding to changes in glucose level, while a properly tuned MPC allows for prediction of glucose dynamics [50,54,57,65] and, as a result, for mitigation of the time delays inherent with s.c. glucose monitoring [5,36,59, 63] and s.c. insulin infusion [40,64]; (ii) MPC allows for relatively straightforward personalizing of the control using patient-specific model parameters. Methods for meal or hypoglycemia detection have been recently developed [18, 19] and self-learning technology has been tested as well. It has been shown that a class of algorithms (known as run-to-run control) can "learn" specifics of patients' daily routine (e.g. timing of meals) and then optimize the response to a subsequent meal using this information [42,43,66], or account for circadian fluctuation in insulin resistance (e.g. dawn phenomenon observed in some people [44]).

BRIEF SUMMARY OF INVENTION

An aspect of an embodiment of the present invention introduces, among other things, the new paradigm of Adaptive Advisory Control (AA Control)—an interactive process involving algorithm-based assessment and communication of physiologic and behavioral parameters and patterns to patients with diabetes, with the goal of assisting the optimization of their glycemic control. Specifically, Applicant has introduced, but not limited thereto, the following:

The Notion of Stochastic Process of Human Behavior:

Behavioral events (meals, exercise, going to bed, waking up) cause the system (person) to change its state, e.g. fasting-to-fed, pre-to-post exercise, awake↔asleep. These states form the "state space" of possible situations a person could encounter. Each transition from one state to another corresponds to a behavioral event. In other words, the behavioral event generator causes system transitions from one state to another. These transitions occur with different probabilities for different people; thus each person is identified by the specific transition probabilities of his/her behavior. This concept was formally described by a stochastic process ξ(n) built upon the concept of stochastic transitions, i.e. transitions which allow identical precursors at one state to have different consequences at the next. Suppose that at its step n (n=1, 2, . . . ) the process ξ(n) is described by a random variable $x_n$, having its values in some set $X_n$. A stochastic transition of the process ξ from $X_n$ to its next stage $X_{n+1}$ is defined by the probabilities P(ξ(n+1)=$x_{n+1}$/ξ(n) ∈ S) for any, $x_{n+1}$ ∈ $X_{n+1}$ and S ∈ $S_n$. Thus, each person is identified by an individual behavioral trajectory defined by his/her own transition probabilities {$p_{ij}$} between any two states (i) and (j). This representation enables a formal description of behavioral patterns that may be considered one of the keys (but not limited thereto) to the methods (and systems and computer readable mediums) in this invention—for each person the transition probabilities can be estimated from data, which serves as the base for tracking behavioral patterns. For example, an estimator can be devised that slides along a window of continuous glucose monitoring (CGM) data and identifies system (person) state changes. To illustrate this action, FIG. 1 graphically presents pilot results in the case of meal observation in a subject from a previously reported study [32]: The meal observer slides down along the days of observation (top-to-bottom). The probability of meal occurring at a certain time is color coded from black (very low) to white (very high). It is seen that, after a week of observation (top line), the times of meals are already well defined and remain stable across 30 days of observation. Breakfast (7:30 AM) and dinner at 8:30 PM appear defined best for this person [46].

Further, estimation of a person's risk for hypoglycemia can be based on our risk analysis theory [35] and on the observation that hypoglycemic episodes typically follow detectable patterns of system disturbances [33] as graphically illustrated in FIG. 2: after 10 days of observation a pattern emerges (black line) which shows a tendency for lower BG at 6 AM and 12 PM. Brighter spots indicate higher likelihood (certainty); thus for this person hypoglycemia pre-breakfast is likely. Finally, assessment of system stability can be done as graphically presented in FIG. 3, which depicts the glucose rate of change clearly identifying fasting overnight state (bright area continuing until 7 AM), and usual times of waking up, and going to bed (11 PM) for a participant in a previously reported study.

An aspect of an embodiment of the present invention introduces an Adaptive Advisory (AA) system assisting the control of diabetes via recognition of key treatment-related bio-behavioral patterns. The methods (and systems and computer readable medium) of aspect of embodiments of the invention may use all available sources of information about the patient; (i) BG Data (e.g. self-monitoring of blood glucose (SMBG) and CMG 22), (ii) Insulin Data (e.g. insulin pump log files or patient treatment records 32), and (iii) Patient Self Reporting Data (e.g. self treatment behaviors, meals, and exercise 52) to:
1. Retroactively assess the risk of hypoglycemia, retroactively assess risk-based reduction of insulin delivery, and then report to the patient how a risk-based insulin reduction system would have acted consistently to prevent hypoglycemia,
2. Develop and periodically refine a mathematical model of the patient consisting in both
   a. a dynamic systems model of the patient's glucose/insulin system, relating oral carbohydrates, physical activity, and subcutaneous insulin infusion to the patient's blood glucose concentration, and
   b. a probabilistic model of the patient's metabolically significant behaviors, which particularly describes the variability of patient behavior, and
3. Retroactively compute optimal insulin delivery schedules based on the physiological and behavioral models above, and then report to the patient how an optimal insulin dosing algorithm would have acted consistently to achieve tight glycemic control.

Based on the physiological and behavioral net effect models above and real-time CGM/SMBG and insulin pump data, the AA system (and method and computer readable medium) can provide on demand correction-insulin advice to the patient. The AA system can be implemented in any contemporary computing device, including portable computers, tablets, a media player (e.g., MP3 based or video player), cellular phone, and smart phones (e.g., personal digital assistant (PDA), as well as Internet-based applications or network applications that have access to the patient data stream.

An aspect of an embodiment of the present invention provides a processor-based method for providing posterior assessment of the risk of hypoglycemic of a patient. The method may comprise: providing an algorithm to compute a statistic, $R_{hypo}$(record), for the risk of hypoglycemia based on the absolute BG levels, BG variability, and insulin delivery that is highly correlated to the posterior (conditional) probability of hypoglycemia, P($E_{hypo}$|record), where $E_{hypo}$ denotes the event of hypoglycemia in the next day and record refers to the subject's historical BG, insulin delivery, and activities record; and providing the computed statistic, $R_{hypo}$(record), whereby actionable prior warning of the possibility of hypoglycemia about the patient is so provided to patient or user.

An aspect of an embodiment of the present invention provides a processor-based method for retroactively providing a safe level of insulin for the patient. The method may comprise: providing an algorithm to retroactively compute a risk-based insulation attenuation factor to the subject's record of insulin delivery; and providing the computed risk-based insulation attenuation factor and applying the risk-based attenuation factor so that any internal threshold is provided to the patient or user for deciding on reduced temporary basal rates before meals and/or following exercise in the future that may be implemented.

An aspect of an embodiment of the present invention provides a processor-based method for providing a "net effect" based patient adoptive model. The method may comprise: providing an algorithm to compute: a dynamic model of the patient's metabolic system, wherein the dynamic model includes descriptive parameters of an individual physiology of the model patient; a corresponding inferred history of behavioral "net effect" model that explains the glucose variability in the historical record through the dynamic model; wherein the "net effect" model includes a mathematical representation perturbations of the model patient; and an update of the patient's physiological parameters based on both (i) the ability of the dynamic model to predict future BG based on known inputs and (ii) the ability of the model to produce net effect curves that are consistent with the patient's record of the perturbations. The method may further comprise providing the update to the patient or user whereby patient or user can use the update for future course of action.

An aspect of an embodiment of the present invention provides a method that may comprise providing a retroactive assessment of the patient's optimal rate of insulin delivery, wherein the algorithm: retroactively computes what the patient's optimal rate of insulin delivery would have been over a predetermined period of historical time given that the disturbances to the system are exactly the historical of net effect curves computed for the patient over that interval of time, wherein for each "history" of net effect curves there is a corresponding "history" of insulin delivery rates that account for meals, exercise, and corrections for each day in the considered interval of time; maps between the net effect curve for a given day and the model-based response of an optimal controller, wherein these vectors of optimal responses are collected and analyzed, and presented to the patient or user for a day-by-day review of insulin treatment; extracts features from the optimal responses that correspond to important but random events by subtracting discrete amounts of insulin associated with meals or accounting for discrete insulin deficits associated with temporary basal rates around exercise, whereby the remaining schedule of insulin delivery corresponds to a representation of the patient's "optimal" basal pattern each day in the historical record; and identifies consistency in the retroactively computed optimal basal rates, such optimal basal rates in a plurality of duration segments representing the patient's treatment duration. The method may further comprise: providing to the patient or user the median level of basal insulin that would have been applied in each segment, wherein the patient or user could use this information to (i) decide upon on reduced temporary basal rates before meals and/or following exercise in the future or (ii) adjust the patient's long-term basal rate profile.

An aspect of an embodiment of the present invention provides a method that may comprise providing an on-demand adaptive correction of insulin advice model. The method may comprise providing an algorithm to include the following computations:

retrospective detecting for meal and exercise activities; stochastic modeling to provide a description about the timing and content of meals and exercise; and providing insulin correction advice to a patient or user that would be in response to a patient and user request.

An aspect of an embodiment of the present invention provides a system for providing posterior assessment of the risk of hypoglycemic of a patient. The system may comprise: a retroactive risk-based safety module having a processor to compute a statistic, $R_{hypo}$(record), for the risk of hypoglycemia based on the absolute BG levels, BG variability, and insulin delivery that is highly correlated to the posterior (conditional) probability of hypoglycemia, $P(E_{hypo}|record)$, where $E_{hypo}$ denotes the event of hypoglycemia in the next day and record refers to the subject's historical BG, insulin delivery, and activities record; and the processor outputs the computed statistic, $R_{hypo}$(record), whereby actionable prior warning of the possibility of hypoglycemia about the patient is so provided to patient or user.

An aspect of an embodiment of the present invention provides a system for retroactively providing a safe level of insulin for the patient. The system may comprise: a retroactive risk-based safety module having a processor to retroactively compute a risk-based insulation attenuation factor to the subject's record of insulin delivery; and the processor outputs the computed risk-based insulation attenuation factor and applying the risk-based attenuation factor so that any internal threshold is provided to the patient or user for deciding on reduced temporary basal rates before meals and/or following exercise in the future that may be implemented.

An aspect of an embodiment of the present invention provides a system for providing a "net effect" based patient adoptive model. The system may comprise: a net effect estimator module having a processor to compute: a dynamic model of the patient's metabolic system, wherein the dynamic model includes descriptive parameters of an individual physiology of the model patient; and a corresponding inferred history of behavioral "net effect" model that explains the glucose variability in the historical record through the dynamic model; wherein the "net effect" model includes a mathematical representation perturbations of the model patient; and a model updater module having a processor to compute: an update of the patient's physiological parameters based on both (i) the ability of the dynamic model to predict future BG based on known inputs and (ii) the ability of the model to produce net effect curves that are consistent with the patient's record of the perturbations. The system outputs the update to the patient or user whereby patient or user can use the update for future course of action.

An aspect of an embodiment of the present invention provides a system configured to provide a retroactive assessment of the patient's optimal rate of insulin delivery. The system comprises a retrospective optimal control analyzer module having a processor configured to: retroactively compute what the patient's optimal rate of insulin delivery would have been over a predetermined period of historical time given that the disturbances to the system are exactly the historical of net effect curves computed for the patient over that interval of time, wherein for each "history" of net effect curves there is a corresponding "history" of insulin delivery rates that account for meals, exercise, and corrections for each day in the considered interval of time; and map between the net effect curve for a given day and the model-based response of an optimal controller, wherein these vectors of optimal responses are collected and analyzed, and presented to the patient or user for a day-by-day review of insulin treatment. The system further comprise a retro-optimal basal rate extractor module having a processor configured to: extract features from the optimal responses that correspond to important but random events by subtracting discrete amounts of insulin associated with meals or accounting for discrete insulin deficits associated with temporary basal rates around exercise, whereby the remaining schedule of insulin delivery corresponds to a representation of the patient's "optimal" basal pattern each day in the historical record; and identify consistency in the retroactively computed optimal basal rates, such optimal basal rates in a plurality of duration segments representing the patient's treatment duration. Also, the system may be configured to: provide an output to the patient or user the median level of basal insulin that would have been applied in each segment, wherein the patient or user could use this information to (i) decide upon on reduced temporary basal rates before meals and/or following exercise in the future or (ii) adjust the patient's long-term basal rate profile.

An aspect of an embodiment of the present invention provides a system configured to provide an on-demand adaptive correction of insulin advice model. The system may comprise: a retrospective meal and exercise detector module having a processor to provide retrospective detecting for meal and exercise activities; a meal and exercise stochastic modeler module having a processor to provide stochastic modeling to provide a description about the timing and content of meals and exercise; and a correction bolus advisor module having a processor to provide and output insulin correction advice to a patient or user that would be in response to a patient and user request.

An aspect of an embodiment of the present invention provides a non-transitory computer readable medium containing program instructions for providing posterior assessment of the risk of hypoglycemic of a patient, wherein execution of the program instructions by one or more processors of a computer system causes the processor to carry out the following steps of: providing an algorithm to compute a statistic, $R_{hypo}$(record), for the risk of hypoglycemia based on the absolute BG levels, BG variability, and insulin delivery that is highly correlated to the posterior (conditional) probability of hypoglycemia, $P(E_{hypo}|record)$, where $E_{hypo}$ denotes the event of hypoglycemia in the next day and record refers to the subject's historical BG, insulin delivery, and activities record; and providing the computed statistic, $R_{hypo}$(record), whereby actionable prior warning of the possibility of hypoglycemia about the patient is so provided to patient or user.

An aspect of an embodiment of the present invention provides a non-transitory computer readable medium containing program instructions for retroactively providing a safe level of insulin for the patient, wherein execution of the program instructions by one or more processors of a computer system causes the processor to carry out the following steps of: providing an algorithm to retroactively compute a risk-based insulation attenuation factor to the subject's record of insulin delivery; and providing the computed risk-based insulation attenuation factor and applying the risk-based attenuation factor so that any internal threshold is provided to the patient or user for deciding on reduced temporary basal rates before meals and/or following exercise in the future that may be implemented.

An aspect of an embodiment of the present invention provides a non-transitory computer readable medium containing program instructions for providing a "net effect" based patient adoptive model, wherein execution of the program instructions by one or more processors of a computer system causes the processor to carry out the following steps of: computing a dynamic model of the patient's metabolic system, wherein the dynamic model includes descriptive parameters of an individual physiology of the model patient; computing a corresponding inferred history of behavioral "net effect" model that explains the glucose variability in the historical record through the dynamic model; wherein the "net effect" model includes a mathematical representation perturbations of the model patient; computing an update of the patient's physiological parameters based on both (i) the ability of the dynamic model to predict future BG based on known inputs and (ii) the ability of the model to produce net effect curves that are consistent with the patient's record of the perturbations; and providing the update to the patient or user whereby patient or user can use the update for future course of action.

An aspect of an embodiment of the present invention provides a non-transitory computer readable medium providing a retroactive assessment of the patient's optimal rate of insulin delivery, wherein execution of the program instructions by one or more processors of a computer system causes the processor to carry out the following steps of: retroactively computing what the patient's optimal rate of insulin delivery would have been over a predetermined period of historical time given that the disturbances to the system are exactly the historical of net effect curves computed for the patient over that interval of time, wherein for each "history" of net effect curves there is a corresponding "history" of insulin delivery rates that account for meals, exercise, and corrections for each day in the considered interval of time; mapping between the net effect curve for a given day and the model-based response of an optimal controller, wherein these vectors of optimal responses are collected and analyzed, and presented to the patient or user for a day-by-day review of insulin treatment; extracting features from the optimal responses that correspond to important but random events by subtracting discrete amounts of insulin associated with meals or accounting for discrete insulin deficits associated with temporary basal rates around exercise, whereby the remaining schedule of insulin delivery corresponds to a representation of the patient's "optimal" basal pattern each day in the historical record; identifying consistency in the retroactively computed optimal basal rates, such optimal basal rates in a plurality of duration segments representing the patient's treatment duration; and providing to the patient or user the median level of basal insulin that would have been applied in each segment, wherein the patient or user could use this information to (i) decide upon on reduced temporary basal rates before meals and/or following exercise in the future or (ii) adjust the patient's long-term basal rate profile.

An aspect of an embodiment of the present invention provides a non-transitory computer readable medium providing an on-demand adaptive correction of insulin advice model, wherein execution of the program instructions by one or more processors of a computer system causes the processor to carry out the following steps of: retrospectively detecting for meal and exercise activities; stochastic modeling to provide a description about the timing and content of meals and exercise; and providing insulin correction advice to a patient or user that would be in response to a patient and user request.

It should be appreciated that while a particular time period may refer to a day, a different time period (or date) may be identified or a longer or shorter period may be substituted as desired or required.

These and other objects, along with advantages and features of various aspects of embodiments of the invention disclosed herein, will be made more apparent from the description, drawings and claims that follow.

BRIEF DESCRIPTION OF THE DRAWINGS

The foregoing and other objects, features and advantages of the present invention, as well as the invention itself, will be more fully understood from the following description of preferred embodiments, when read together with the accompanying drawings.

DETAILED DESCRIPTION OF THE INVENTION

Figure 4:
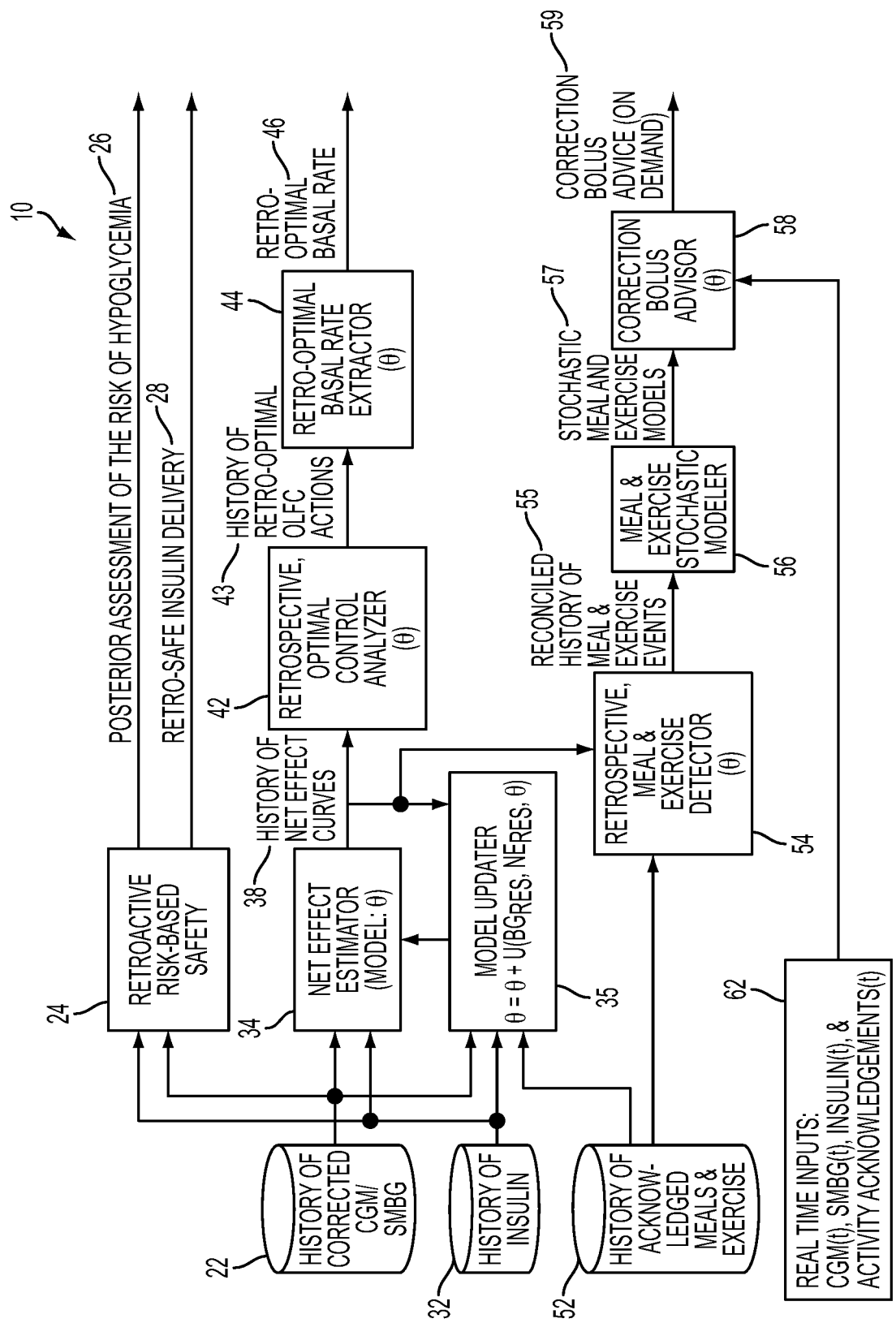
FIG. 4 provides a schematic of Overview of Adaptive Advisory (AA) System.

Some exemplary elements of the AA System 10 are illustrated in FIG. 4. All four primary functions of the system provide, among other things, long-term historical trends in the patient's physiological responses to carbohydrate intake and insulin, as well as to the patient's self treatment, eating, and exercise behaviors. The "retroactive" advisory components are designed to illustrate to the patient how a safety-supervised and/or optimal insulin regiment would have differed from what the patient actually did, providing the evidence needed by the patient to change his/her self treatment behaviors. The "on demand" component, which relies on real-time BG and insulin data in addition to the historical record, can advise the patient on correction insulin amounts, acting in a sense as an adaptive bolus calculator, i.e., adapted to the patient's physiology, anticipated future behaviors, and real-time metabolic state.

It is worth noting that the AA System above could easily be used in conjunction with a real time safety supervision system, in which CGM and insulin data inform model-based reductions to insulin delivery (e.g. attenuation of basal rate) in real time. The use of such a safety supervision system is entirely optional.

The subsections that follow provide a detailed description of the four main system components: (i) Retroactive Risk-Based Safety, (ii) "Net Effect"-Based Patient Adaptive Model, (iii) Retroactive Assessment of Optimal Insulin Delivery, and (iv) On Demand Adaptive Correction Insulin Advice.

It should be appreciated that the modules, systems, subsystems and devices associated with the invention may be integrally or separately formed in a variety of forms, and be in communication wirelessly or by-wire (or a combination of both) utilizing technology and approaches as would be available to one skilled in the art. Some non-limiting examples of device, module, network and system interfaces and communications may be referred to by all of the references, applications and publications disclosed herein (and are hereby incorporated by reference). Moreover, an example of possible interface and communication between the various systems, devices and networks is disclosed in (but not limited thereto) International Patent Application Serial No. PCT/US2008/082063, Magni, et al., entitled "Model Predictive Control Based Method for Closed-Loop Control of Insulin Delivery in Diabetes Using Continuous Glucose Sensing," filed Oct. 31, 2008; and U.S. patent application Ser. No. 12/740,275, Magni, et al., entitled "Predictive Control Based System and Method for Control of Insulin Delivery in Diabetes Using Glucose Sensing," filed Apr. 28, 2010—in particular see FIGS. 1-4 and 6-10 of Magni et al. (of which both of the disclosures are hereby incorporated by reference herein in their entirety).

Figure 5:
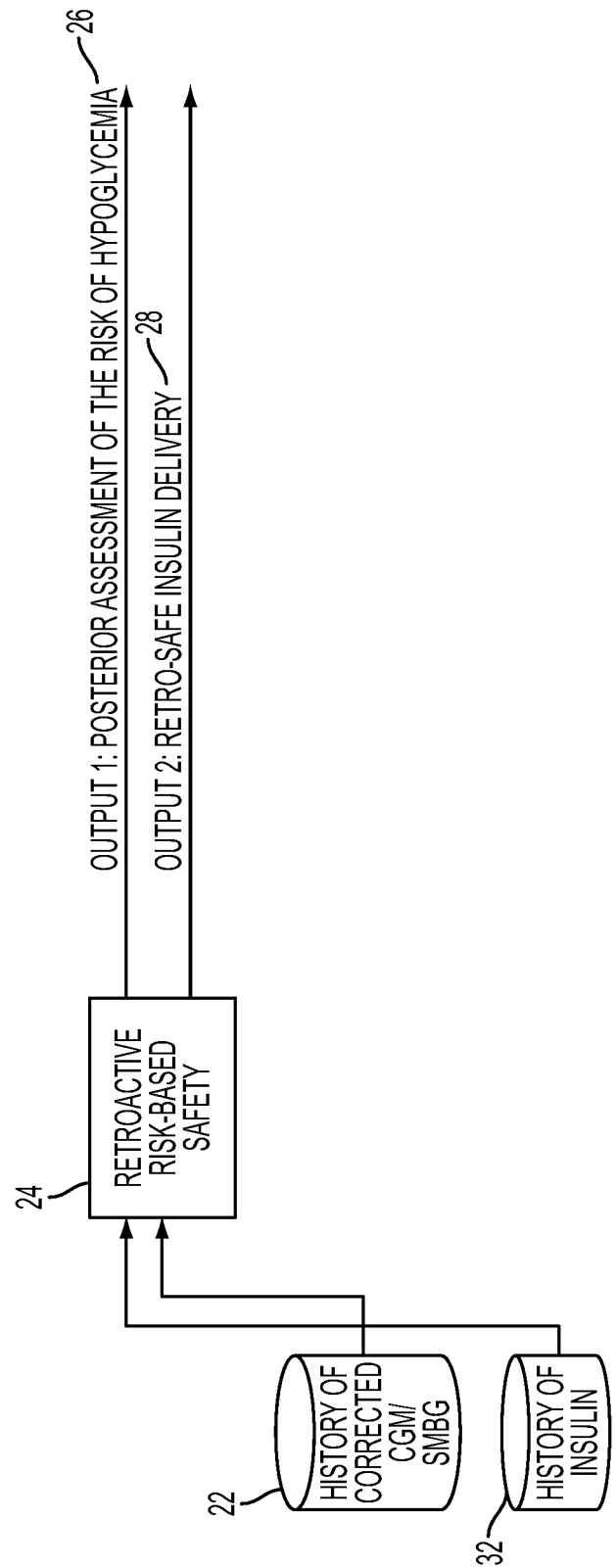
FIG. 5 provides a schematic of Retroactive Risk-Based Safety Assessment.

Component 1—Retroactive Risk-Based Safety:

The parts of the system devoted to Retroactive Risk-Based Safety assessment are illustrated in FIG. 5, resulting in two main outputs, both of which can be displayed to the patient for enhanced understanding of his/her risk of hypoglycemia as follows:

Output 1: Posterior Assessment of the Risk of Hypoglycemia:

This part of the Retroactive Risk-Based Safety subsystem analyzes the historical record and uses kernel density estimates of the patient's BG time series to compute a statistic, $R_{hypo}$(record), for the risk of hypoglycemia based on the absolute BG levels, BG variability, and insulin delivery that is highly correlated to the posterior (conditional) probability of hypoglycemia, $P(E_{hypo}|record)$, where $E_{hypo}$ denotes the event of hypoglycemia in the next day and record refers to the patients historical BG 22, insulin 32, and activities record 52. By explicitly informing the patient of the posterior probability of hypoglycemia 26 over the next treatment day, the patient gets actionable prior warning of the possibility of hypoglycemia. The patient could use this information to lower his/her own internal thresholds for deciding on reduced temporary basal rates before meals and/or following exercise. This "posterior assessment" of the risk of hypoglycemia is intended to complement existing methods for computing "BG profiles" that highlight hypoglycemia "risk zones" throughout the treatment day (as in FIG. 2). This invention does not claim the notion of a "BG profile", but rather it claims the method of computing the posterior probability of hypoglycemia given the patient's historical record (22, 32, 52).

It should be appreciated that the absolute BG levels and BG variability may be data derived from a patient's CGM device (or records or data storage of glucose readings) and the absolute insulin delivery may be data obtained from the patient's insulin pump device (or records or data storage of insulin delivery) from multiple daily injections. For instance, in various embodiments as disclosed throughout, the manifestation of the AA system is based on CGM and insulin pump data or manual injection of insulin data. However, in alternative embodiments, the components of the AA system can be realized without CGM or an insulin pump, though the time scale for making the computations would have to change considerable. For example, "net effect" curves based on SMBG and insulin pump data could be computed, though such a methodology would need extensively more such "net effect" curves to obtain an accurate representation of patient behavior. As a further example, an SMBG device may be utilized with a manual insulin injection device, such as an insulin pen, needle or similar type of devices.

Output 2: Retro-Safe Insulin Delivery 28:

This part of the Retroactive Risk-Based Safety subsystem analyzes the historical record and retroactively computes a risk based insulin attenuation factor to the patient's record of insulin delivery. In one embodiment of the method, the risk-based attenuation factor (alternatively insulin constraint) would be computed as in [30]:

$$\phi(R(t,\tau)) = \frac{1}{1 + k_{patient}R(t,\tau)}$$

where R(t, τ) is a measure of the risk of hypoglycemia between time t and t+τ based on the historical record of BG and insulin data up to time t, based on the BG symmetrization of function in [34] and $k_{patient}$ is a patient-specific "aggressiveness" factor. Other methods of computing attenuation factors exist, including methods based on assessing the patient's active insulin up to time t and adjusting the measured value of BG at time t, based on the patient's correction factor.

An exemplary key step of an embodiment of the invention (but not limited thereto) is that the system (and related method) looks for consistency in the retroactively computed attenuation factors. Specifically, the system computes kernel density estimates of φ(R(t, τ)) in 24 one-hour bins representing the patient's treatment day, and then presents to the patient the median level attenuation that would have been applied in each hour-long segment. Again, the patient could use this information to lower his/her own internal thresholds for deciding on reduced temporary basal rates before meals and/or following exercise in the future.

Figure 1:
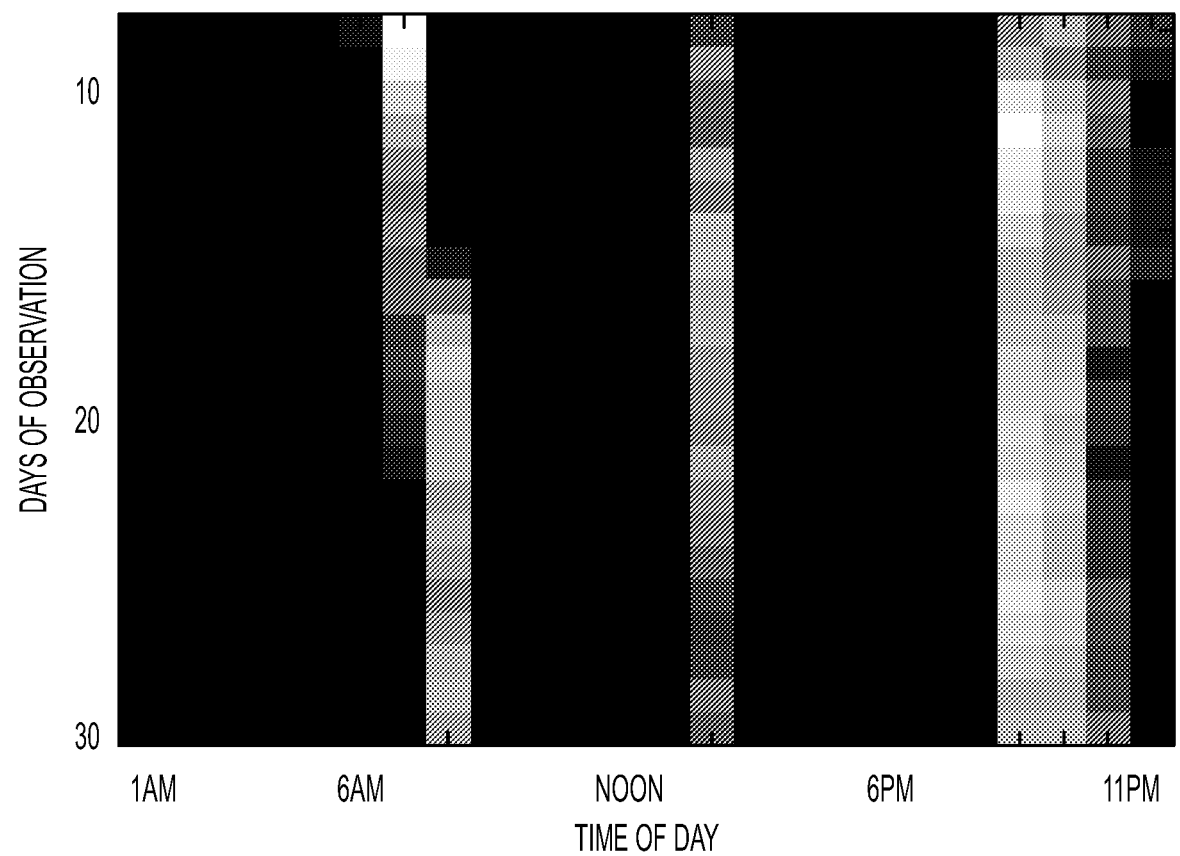
FIG. 1 graphically presents pilot results in the case of meal observation in a subject from a previously reported study, which represents an example of Probabilistic Assessment of Meal Behavioral Patterns.
Figure 2:
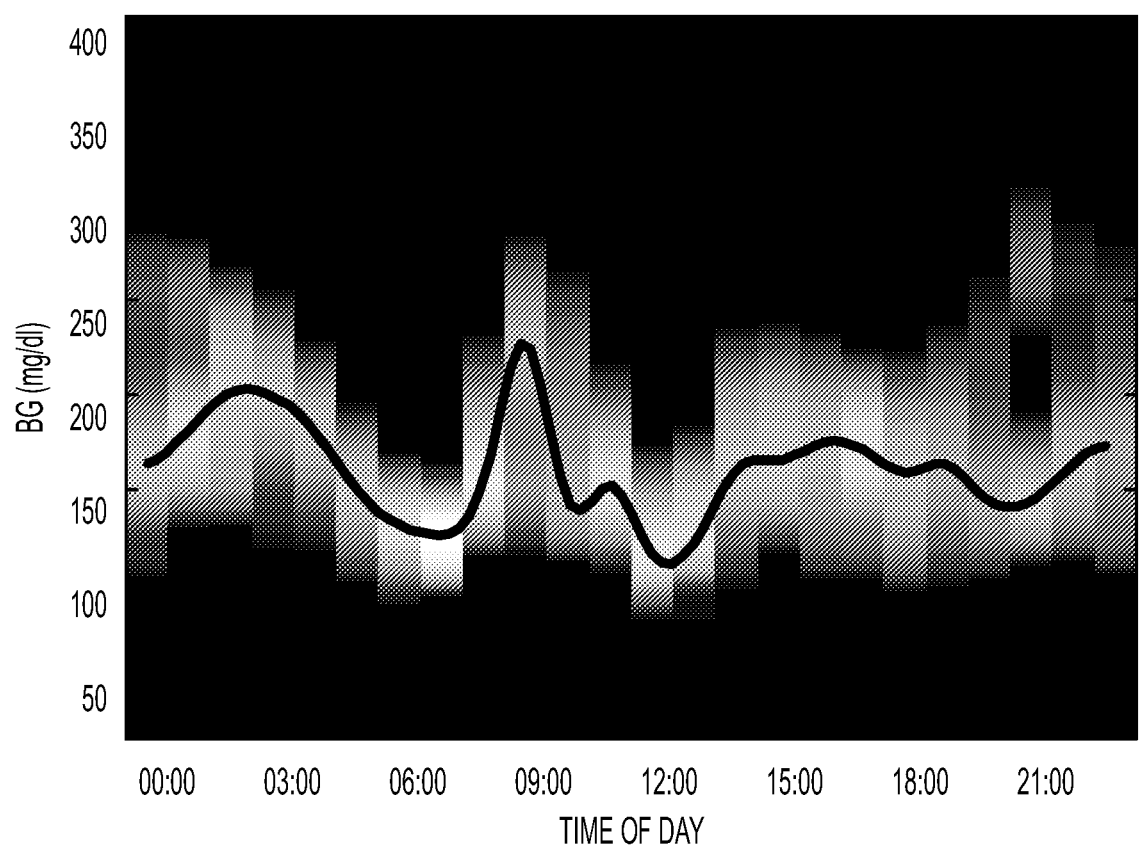
FIG. 2 graphically illustrates the observation that hypoglycemic episodes typically follow detectable patterns of system disturbances as provided by the subject, which represents an example of Probabilistic Assessment of Risks for Hypo- and Hyperglycemia.
Figure 3:
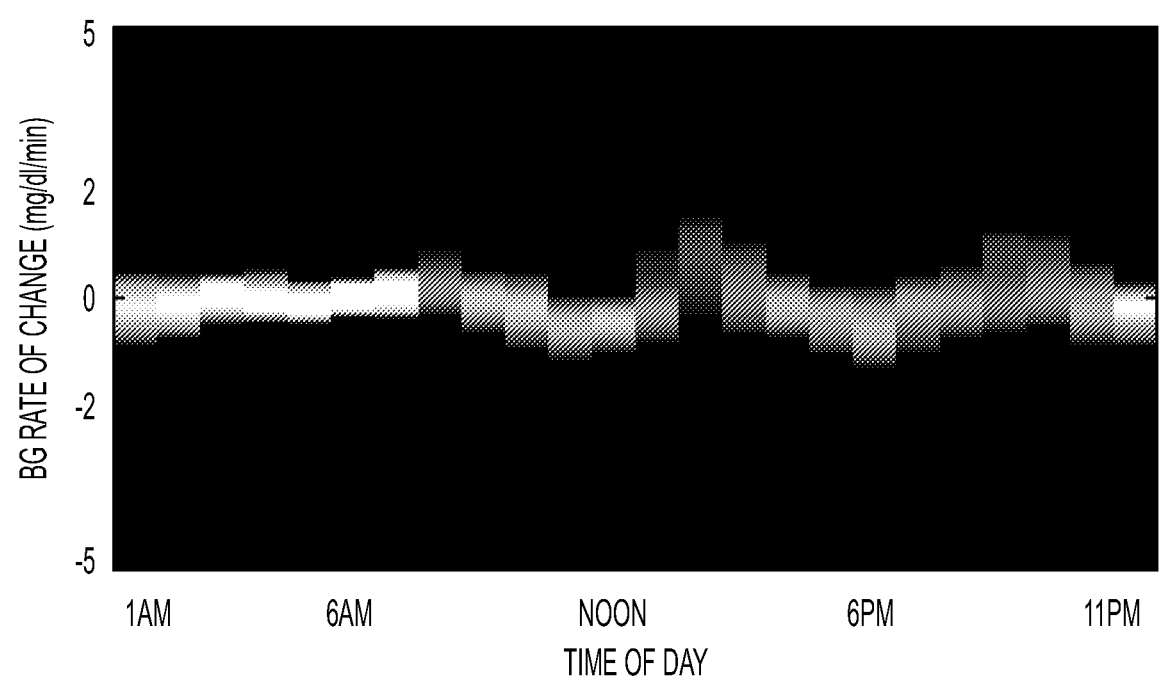
FIG. 3 graphically depicts the glucose rate of change clearly identifying fasting overnight state (bright area continuing until 7 AM), and usual times of waking up, and going to bed (11 PM) for a participant in a previously reported study, which represents an example of Probabilistic Assessment of System Stability Patterns (sleep/awake patterns).
Figure 6:
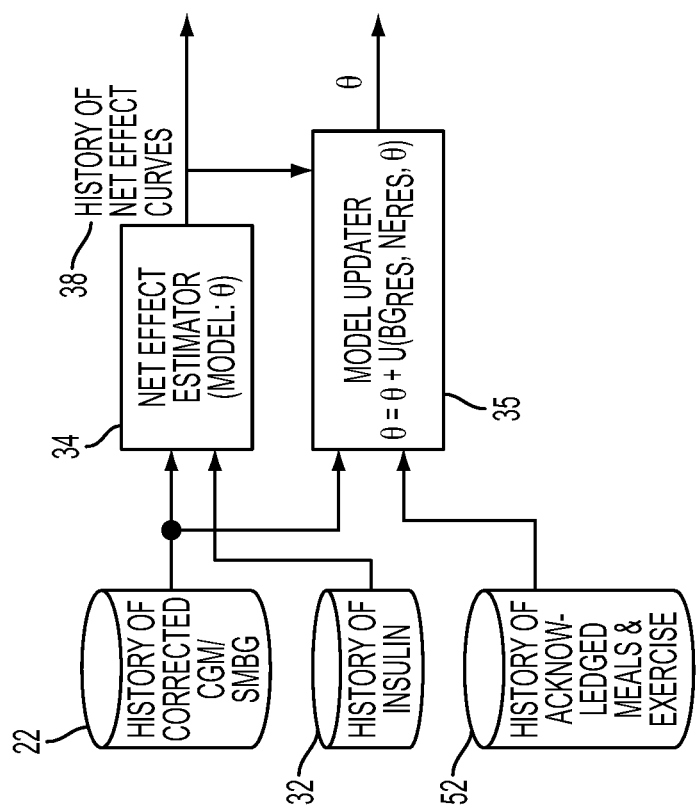
FIG. 6 provides a schematic of "Net Effect"-Based Patient Adaptive Model.

Component 2: "Net Effect"-Based Patient Adaptive Model:

The parts of the system devoted to the "Net Effect"-Based Patient Adaptive Model are illustrated in FIG. 6. The model that the AA System produces may include (but not limited thereto) two main components: (i) a dynamic model of the patient's metabolic system and (ii) a corresponding, inferred history of behavioral "net effect" curves that explain the glucose variability in the historical record through the dynamic model. In one aspect, the "Net Effect"-Based Patient Adaptive Model is, but not limited thereto, a formal mathematical representation of meal profiles such as those presented in FIG. 1, but also taking into account the influence of other system perturbations, such as physical activity, and sleep/awake periods (FIG. 3).

The metabolic model, descriptive of the patient's individual physiology, provides a mathematical representation of the dynamic relationship between oral carbs d (g/min), physical activity e (cal/min), subcutaneous insulin u (U/hr), and the patient's metabolic state vector X whose elements include glucose and insulin concentrations (mg/dl) in various compartments of the body and carbohydrate mass (mg) in the gut. Abstractly, this relationship can be described as a set of discrete-time nonlinear difference equations:

$$\chi(k+1)=F(\chi(k),u(k),d(k),e(k);\theta(k))$$

$$BG_{model}(k)=G(\chi(k),u(k),d(k),e(k);\theta(k))$$

where F and G are nonlinear system equations and θ(k) is a vector of parameter values that are characteristic of the patient, such as body weight, volumes of distribution in various compartments, various time constant that describe the rates of absorption and clearance between various compartments, some of which are prone to varying as a function of time k. This nonlinear representation can be linearized around any desired operating point (e.g. steady state glucose concentration) to yield a linear dynamic model:

$$x(k+1)=Ax(k)+B_u u_\delta(k)+B_d d(k)+B_e e(k)$$

$$y(k)=Cx(k)$$

where x is the vector of metabolic state differentials (away from the operating point), $u_\delta$ (U/hr) is the deviation in insulin delivery from the patient's steady state (basal) insulin delivery rate, A, $B_u$, $B_d$, $B_e$ are the state space matrices of the linear model, and y(k) represents BG deviation away from the desired operating point. (Note that the dependence on θ(k) is embedded within the state space matrices A, $B_u$, $B_d$, $B_e$.)

It should be appreciated that alternatively, the dynamic relationships can be described as a set of continuous-time nonlinear differential equations:

$$\dot{\chi}(t)=F(\chi(t),u(t),d(t),e(t);\theta(t))$$

$$BG_{model}(t)=G(\chi(t),u(t),d(t),e(t);\theta(t)).$$

Some of the novel elements of the "Net Effect"-Based Patient Adaptive Model are, but not limited thereto, described below.

Net Effect Estimator 34:

This element of the "Net Effect"-Based Patient Adaptive Model produces a "history" of virtual system inputs (a.k.a. "net effect") that reconciles the patient's historical record of BG 22 and insulin delivery 32. To be more specific, given the record of the patient's BG concentration and insulin delivery, $\{BG(k)\}_{k \in day}$ and $\{u(k)\}_{k \in day}$ the net effect that reconciles the historical information is the vector of virtual carbohydrate inputs $\{d_{n.e.}(k)\}_{k \in day}$ that minimizes the error function:

$$\text{dist}(\{BG(k)\}_{k \in day},\{BG_{model}(k)\}_{k \in day}|\{u(k)\}_{k \in day},\{d_{n.e.}(k)\}_{k \in day}),$$

where dist measures the distance between two vectors of BG concentration (in this case actual BG versus model-predicted BG) given the fixed record of insulin delivery $\{u(k)\}_{k \in day}$ and the candidate net effect vector $\{d_{n.e.}(k)\}_{k \in day}$.

Note that the resulting optimal net effect vector (aka. net effect curve 38) $\{d_{n.e.}(k)\}_{k \in day}$ optimal reconciles the BG and insulin data collected by the patient through a virtual carbohydrate signal, which captures all external influences on the patient as a single external disturbance signal measured in (mg/min). When the net effect curve 38 is positive this may correspond to the patient actually eating, or it may correspond a period of the day in which the patient is experiencing enhanced insulin sensitivity. When the net effect curve 38 is negative then this may correspond to the patient engaging in intense physical activity or exercise.

Note also that the computed net effect curve 38 is implicitly a function of the patient's physiological model, parameterized by θ(k). Thus a poorly adapted physiological model is likely to produce unusual-looking net effect curves 38, and the side-effect of a well-adapted physiological model is a set of net effect curves that correspond well to the patients record or recollection of daily activities, meal and exercise behaviors, and self treatment.

Different types of distance measures are possible for assessing the patients "net effect," including weighted $l_1$, $l_2$, and $l_\infty$ norms. The combination of the $l_2$ norm with the linearized version of the patient physiological model makes it particularly easy to compute daily net effect.

Model Updater 35:

It is common practice to use techniques of "system identification" to recursively update the parameters of dynamic model. In the context of model-based treatment of diabetes, such techniques allow for the estimation of the patients physiological model parameters $\{\theta(k)\}_{k \in day}$ including daily variability due to the patients circadian rhythm. Many techniques have been employed including linear least-squares fitting of the data, parametric and non-parametric system identification, adaptive recursive estimation. All of these techniques work to ensure endogenous consistency of the model with the data, generally taking "exact knowledge" of patient-inputs (meals and exercise) for granted. Of course, prior knowledge of the precise content and timing of meals and exercise is only possible within a clinical environment.

And, frequently requiring the patient to undergo such testing in order to track long time-scale variability, is not economically feasible.

An aspect of an embodiment of the present invention addresses, among other things, the latter concerns by integrating the notion of net effect into the long-term adaptation of the patient's physiological model parameters. As mentioned above, the side-effect of a well-adapted physiological model is a set of "net effect" curves 38 that correspond well to the patients record or recollection of daily activities, meal and exercise behaviors, and self treatment. Specifically, our system (and method and computer readable medium) may use a recursive procedure for updating the patients physiological parameters based on both (i) the ability of the model to predict future BG based on known inputs and (ii) the ability of the model to produce net effect curves 38 that are consistent with the patient's record of eating, exercise, and self-treatment behaviors. Mathematically, the net-effect based Model Updater, takes the form $$\theta := \theta + U(BG_{res}, NE_{res}; \theta),$$

where U is the recursive parameter update function, which could be gradient-based, $BG_{res}$ is a vector of BG model prediction errors (residuals) and $NE_{res}$ is a vector of errors between the computed net effect curve and the patient's record of actual (verified) behavioral inputs. In practice, it is justified to adjust the model on multiple time scales. For example, parameter updates can be computed daily based on BG residuals:

$$\theta := \theta + U_1(BG_{res}; \theta),$$

and updates based on net effect mismatch can be computed on a longer time scale, say every week or month:

$$\theta := \theta + U_2(NE_{res}; \theta).$$

Component 3: Retroactive Assessment of Optimal Insulin Delivery

Figure 7:
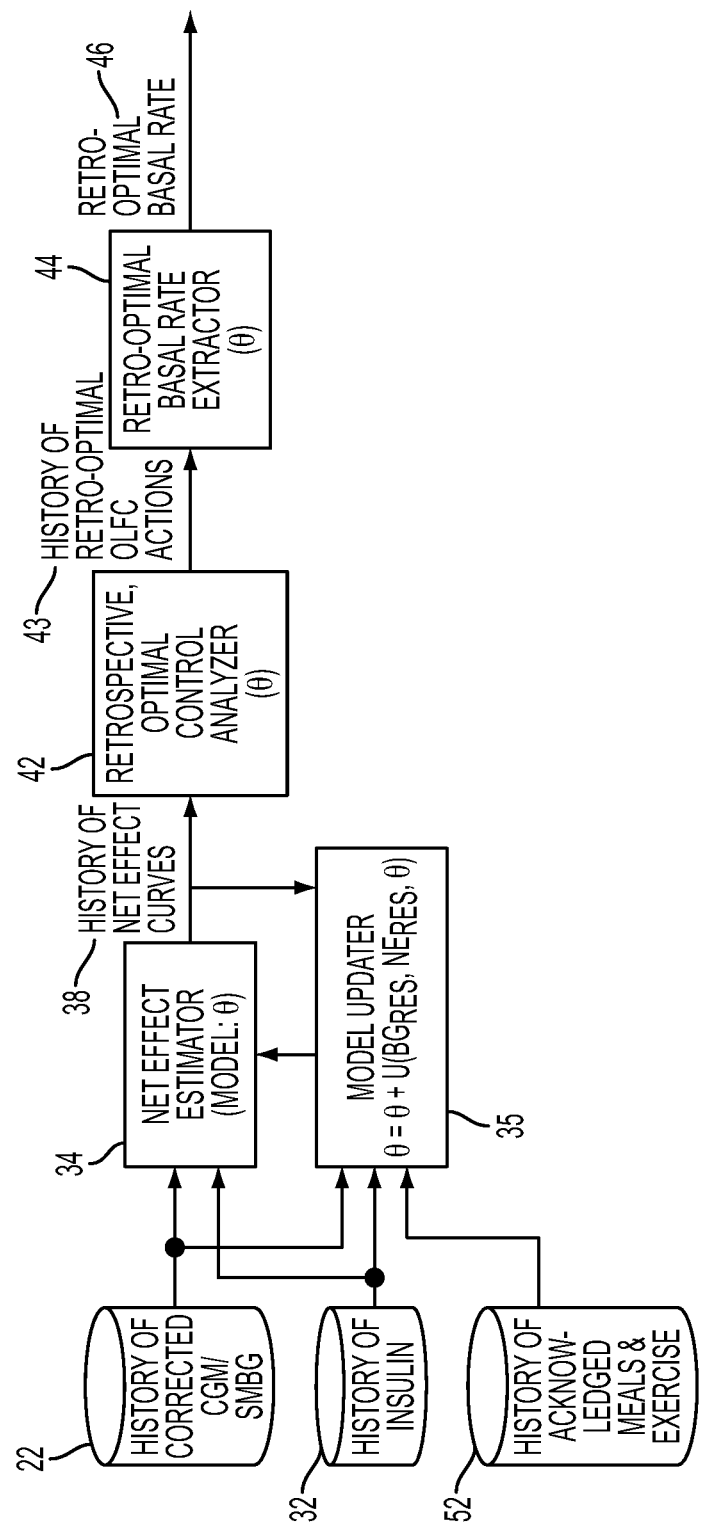
FIG. 7 provides a schematic of Retroactive Assessment of Optimal Insulin Delivery.

The parts of the system devoted to Retroactive Assessment of Optimal Insulin Delivery are illustrated in FIG. 7. One of the key elements of the Retroactive Assessment of Optimal Insulin Delivery subsystem, but not limited thereto, are (i) the Retrospective Optimal Control Analyzer 42 and (ii) the Retro-Optimal Basal Rate Extractor 44, both of which make use of the "Net Effect"-Based Patient Adaptive Model, as described in the following paragraphs.

Retrospective Optimal Control Analyzer 42:

This element of the Retroactive Assessment of Optimal Insulin Delivery subsystem serves to retroactively compute what the patient's optimal rate of insulin delivery would have been over a predetermined period of historical time given that the disturbances to the system are exactly the historical of net effect curves 38 computed for the patient over that interval of time. Thus, for each "history" of net effect curves there is a corresponding "history" of insulin delivery rates that account for meals, exercise, and corrections for each day in the considered interval of time. For example, associated with any day in the historical record, we have $$\{d_{n.e.}(k)\}_{k \in day} \to \{u_{opt}(k)\}_{k \in day}$$

i.e., there is a mapping between the net effect curve 38 for a given day and the model-based response of an optimal controller 42. These vectors of optimal responses can be collected and analyzed, and can be directly presented to the patient for a day-by-day review of insulin treatment. A specific form of this analysis takes shape in the Retro-Optimal Basal Rate Extract 46 described below.

It may be noted that the Retrospective Optimal Control Analyzer 42 uses both components of the "Net Effect"-Based Patient Adaptive Model, i.e. both the "history" of net effect curves computed for the patient and the adapted patient physiological model.

A beneficial feature of this architecture is that, but not limited thereto, errors in the patient model (i.e. θ misadapted to the patient) do not have a large effect on the retrospective optimal control analysis. The reason for this is that, while θ may be off, the net effect curves computed for the patient reconcile the actual insulin and BG data for the patient through the model. As long as θ is close ("in the ballpark"), the optimal control responses will still be patient-adapted.

Different types of optimal control methodologies (from the prior art, for example) could be employed to compute the optimal control responses $\{u_{opt}(k)\}_{k \in day}$, including deterministic and stochastic model predictive control algorithms [20,27,38,45]. The Open-Loop Feedback Control (OLFC) scheme of [47] is particularly well-suited for the various embodiments of the invention.

A novel aspect of an aspect of an embodiment of the present invention, but not limited thereto, is the concept, method, and system based on (i) feeding the patient's history of net effect curves 38 into various types of optimal control algorithms and (ii) retroactively analyzing the optimal responses, and informing the patient of through comparative analysis.

Retro-Optimal Basal Rate Extractor 44:

This element of the Retroactive Assessment of Optimal Insulin Delivery subsystem serves to (i) take the "history 43" of optimal control responses computed by the Retrospective Optimal Control Analyzer 42 and (ii) extract features from the optimal responses that correspond to important but random events (i.e. subtract discrete amounts of insulin associated with meals or account for discrete insulin deficits associated with temporary basal rates around exercise). The remaining schedule of insulin delivery corresponds to a representation of the patient's "optimal" basal pattern each day in the historical record.

Next, the Retro-Optimal Basal Rate Extractor 44 then looks for consistency in the retroactively computed optimal basal rates. Specifically, the system computes kernel density estimates of the optimal basal rates in 24 one-hour bins representing the patient's treatment day, and then presents to the patient the median level of basal insulin 46 that would have been applied in each hour-long segment. The patient could use this information to (i) decide upon on reduced temporary basal rates before meals and/or following exercise in the future or (ii) adjust his/her long-term basal rate profile.

Component 4: On Demand Adaptive Correction Insulin Advice

Figure 8:
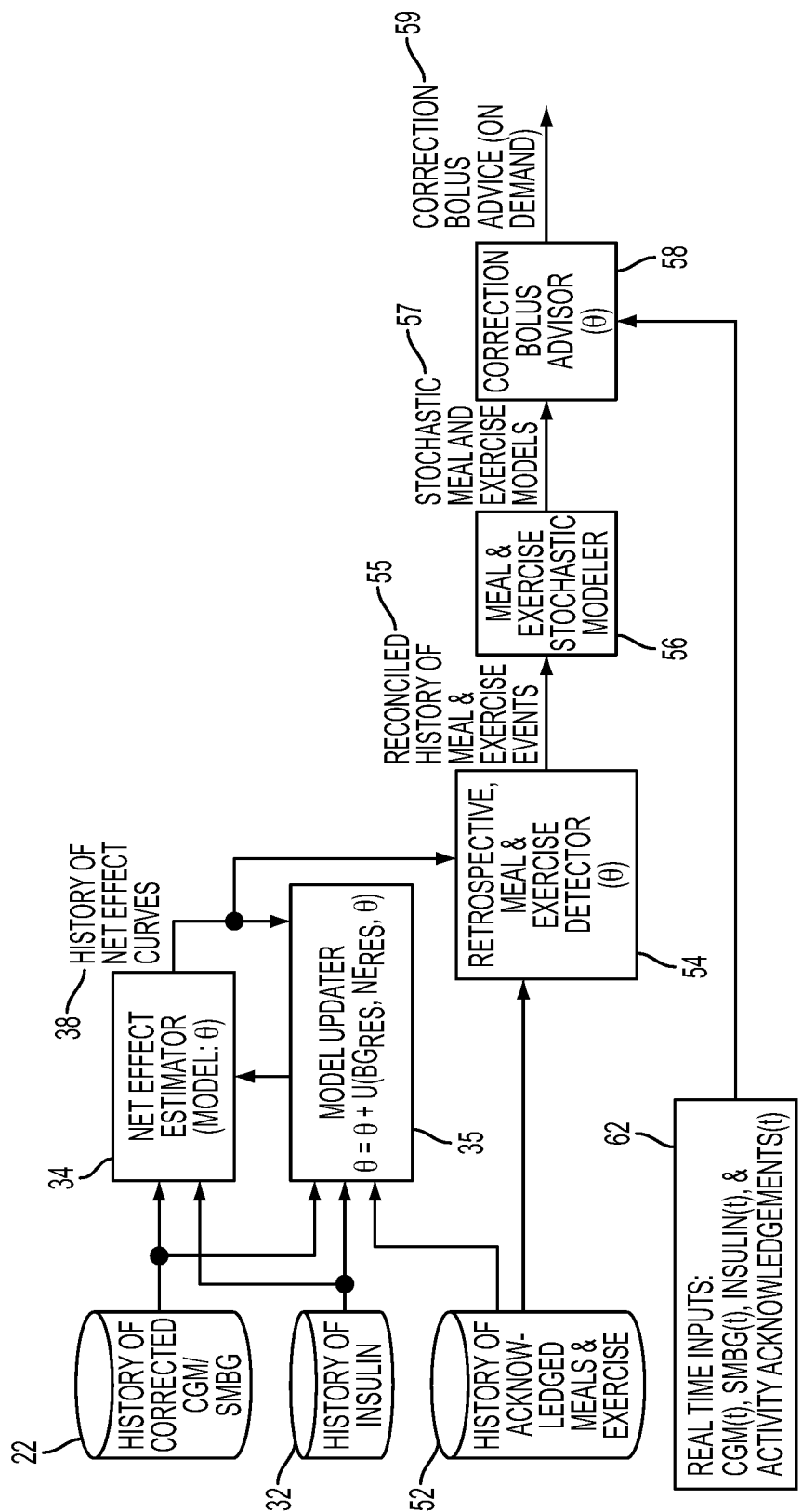
FIG. 8 provides a schematic of On Demand Adaptive Correction Insulin Advice.

Some of the exemplary parts of the system devoted to On Demand Adaptive Correction Insulin Advice are illustrated in FIG. 8. An over-arching goal, among other things, of this component of the Adaptive Advisory system (and related method) is to provide in-the-moment correction insulin advice to the patient based on both (i) the historical record 22, 32, 52 and (ii) real-time CGM/SMBG measurements and insulin pump data 62. One of the first steps of this system may be to develop a stochastic model of upcoming behavioral disturbances. With this model it is possible to reason about appropriate correction insulin amounts that anticipate meals and exercise that are forthcoming.

Some of the key elements, but not limited thereto, of the On Demand Adaptive Correction Insulin Advice subsystem may be (i) the Retrospective Meal & Exercise Detector, 54

(ii) the Meal & Exercise Stochastic Modeler 56, and (iii) the on demand Correction Bolus Advisor 58, described in the following paragraphs. These elements of the subsystem can work in tandem, and there is also independent value in each element individually.

Retrospective Meal & Exercise Detector 54:

This element of the On Demand Adaptive Correction Insulin Advice subsystem serves to reconcile 55 the current "history" of patient "net effect" curves 38 with the historical record of patient-acknowledged meals and exercise events to produce a validated (high-confidence) record of relevant patient behaviors. The Retrospective Meal & Exercise Detector 54 looks for discrepancies between (i) the net effect curves 38 computed from the available BG and insulin data for the patient and (ii) the meal and exercise events 55 that are acknowledged 62 by the patient through the systems user interface. When discrepancies arise the Retrospective Meal & Exercise Detector 54 suggests possible resolutions, such as "Perhaps you had a meal between 1 PM and 2 PM that you failed to acknowledge?" or "There is an indication to you engaged in intense physical activity between 3 PM and 3:30 PM. Is this true?" The responses from the patient are then taken to form the final, validated record of relevant patient activities.

Internally, the Retrospective Meal & Exercise Detector 54 employs a method of analyzing the net effect curves 36 to produce discrete estimates of meal and exercise events. The method may be based on, among other things, (i) identifying significant local extreme of the net effect curves, (ii) computing areas under the over time-windows that correspond to meals and exercise, (iii) computing most-likely times of meal and exercise events, and then (iv) confirming that the resulting estimation of meal and exercise behaviors yield model-predicted BG traces that are close to the actual record.

Meal & Exercise Stochastic Modeler 56:

This element of the On Demand Adaptive Correction Insulin Advice subsystem serves to take the reconciled (validated) history of behavioral events 55 above, and then produce a stochastic model 57 that describes the timing and content of meals and exercise. The model 57 essentially describes the patient's daily behavior as a sequence of non-overlapping meal and exercise regimes. Each regime is described in terms of (i) an earliest possible time at which the disturbance could "arrive" (e.g. the earliest possible breakfast time), (ii) a latest possible disturbance arrival time (e.g. the latest possible breakfast time), and (iii) a relative frequency distribution for the times at which the disturbance arrives within the regime that also accounts for the possibility that the disturbance will be "skipped" [67].

One of the key novel aspects here is the method by which meal regimes are determined from the reconciled history of meal and exercise events 55 (based on clustering analysis), for estimating the relative frequency distribution of meal timing within the regime, and for characterizing the random variable that describes the size of the meal or exercise disturbance associated with the regime.

Figure 9:
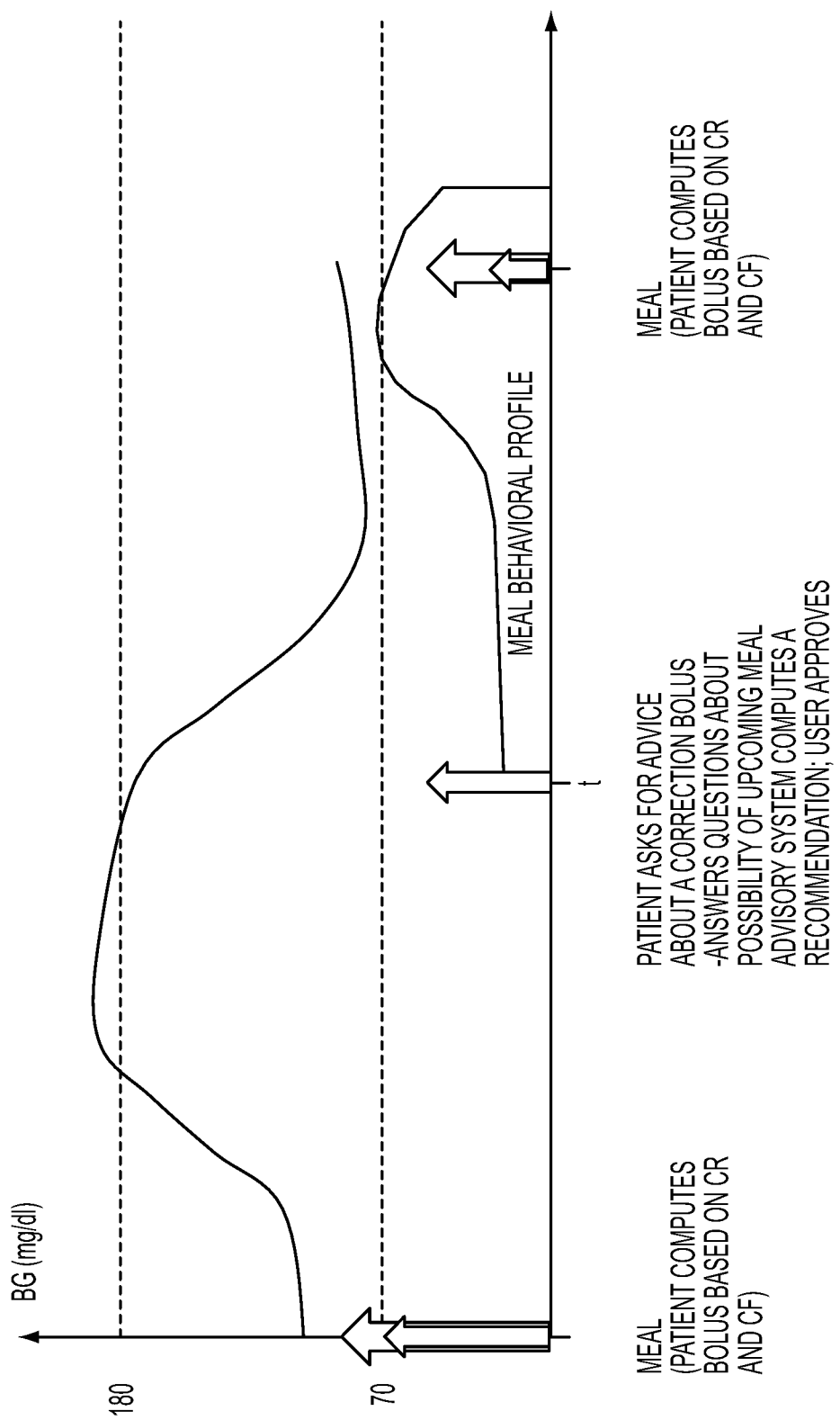
FIG. 9 graphically illustrates an example of the On Demand Adaptive Correction Insulin System.

Correction Bolus Advisor 58:

This element of the On Demand Adaptive Correction Insulin Advice subsystem serves to continuously monitor the patient's status and to provide correction insulin advice 59 in the moment the patient asks for it, based on (i) the stochastic model 57 above for upcoming behavioral disturbances and (ii) the current physiological model for the patient (i.e., dynamic model of the patient's metabolic system) that allows for the prediction of the impact of various alternative correction insulin amounts. The concept of this user-prompted advisory mode correction system is illustrated in FIG. 9. FIG. 9 graphically illustrates an example of the On Demand Adaptive Correction Insulin System. The system and method assumes that (i) the patient is in charge of computing insulin boluses at mealtimes using conventional methods and (ii) the patient uses our advisory system to address unplanned hyperglycemia, such as at time t shown in the figure. When the patient activates the advisory system, he/she has the option to provide information regarding the timing and content of the next meal, and the system proceeds to update the stochastic model 56 of meal and exercise timing (referred to as the Meal Behavioral Profile and illustrated as a shaded probability distribution in the figure). Next, the system computes an insulin recommendation that is optimal with respect the patient's future (random) metabolic trajectory. Specifically, the advised bolus is computed as the optimal solution to an indefinite-horizon linear quadratic problem defined by the uncertain time at which the patient will next eat.

One of the key benefits of the proposed method, but not limited thereto, is that it is minimally invasive and only provides advice in response to the user's interaction with the system. With the patient being ultimately "in charge," he/she can easily override the system in case of un-modeled metabolic disturbances, e.g. intense physical activity. Another benefit of the system, among other things, is that it allows the patient to implement a "conventional" bolusing strategy at mealtimes, including the option to implement an extended meal bolus to account for meals with high fat content. The framework that we present here computes correction bolus insulin recommendations based on a model of the patient's metabolism, and the framework can adapt to either a "population average" model or patient-specific metabolic models. In addition, recommended insulin boluses are computed with respect to a model of the patient's individual eating behavior. In particular, the system is constantly aware of the next meal opportunity and is prepared to optimize correction recommendations with respect to an empirical stochastic model for meal timing and size (including the possibility that the meal will be skipped). Knowing that the patient is responsible for mealtime boluses, the system will avoid making large corrections immediately prior to anticipated meals. Finally, the insulin recommendations produced by the system anticipate the patient's treatment behavior at the time of the next meal, knowing that the patient will compute a mealtime bolus based on his/her insulin to carbohydrate ratio (CR) and correction factor (CF).

Implementation of the Adaptive Advisory System

Figure 10:
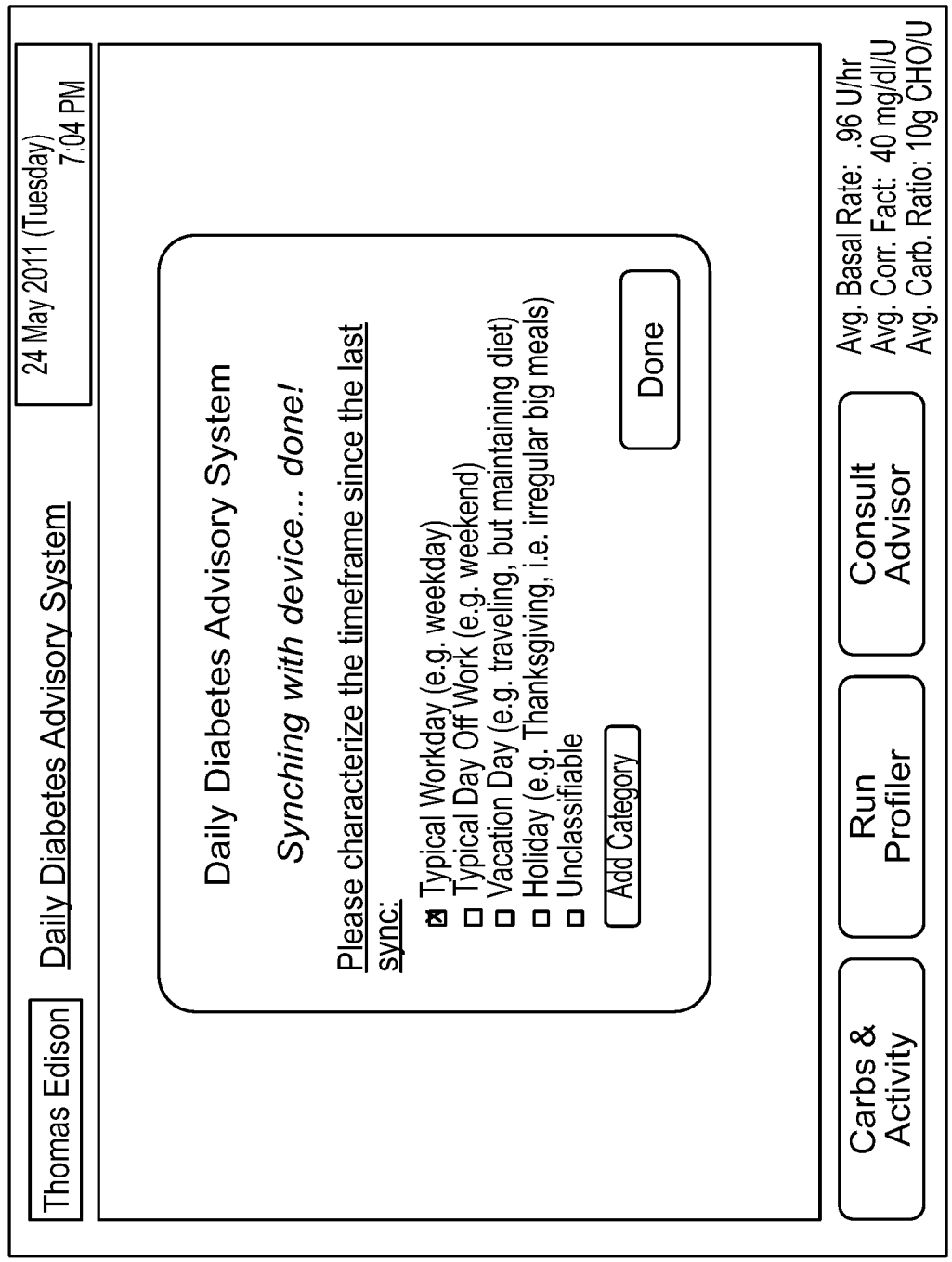
FIGS. 10-15 provide screenshots of one implementation of an embodiment of the AA System.
Figure 11:
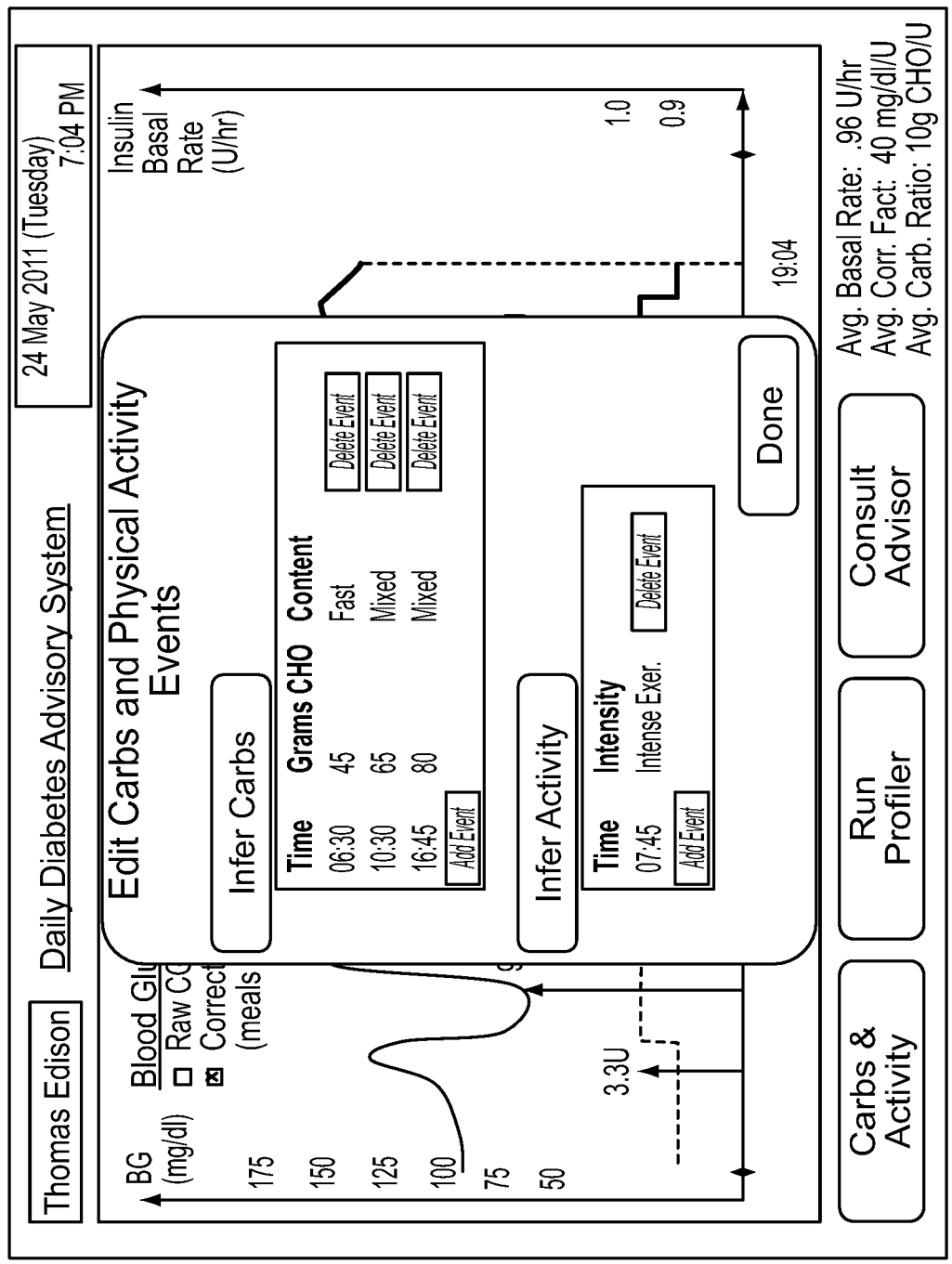
Figure 12:
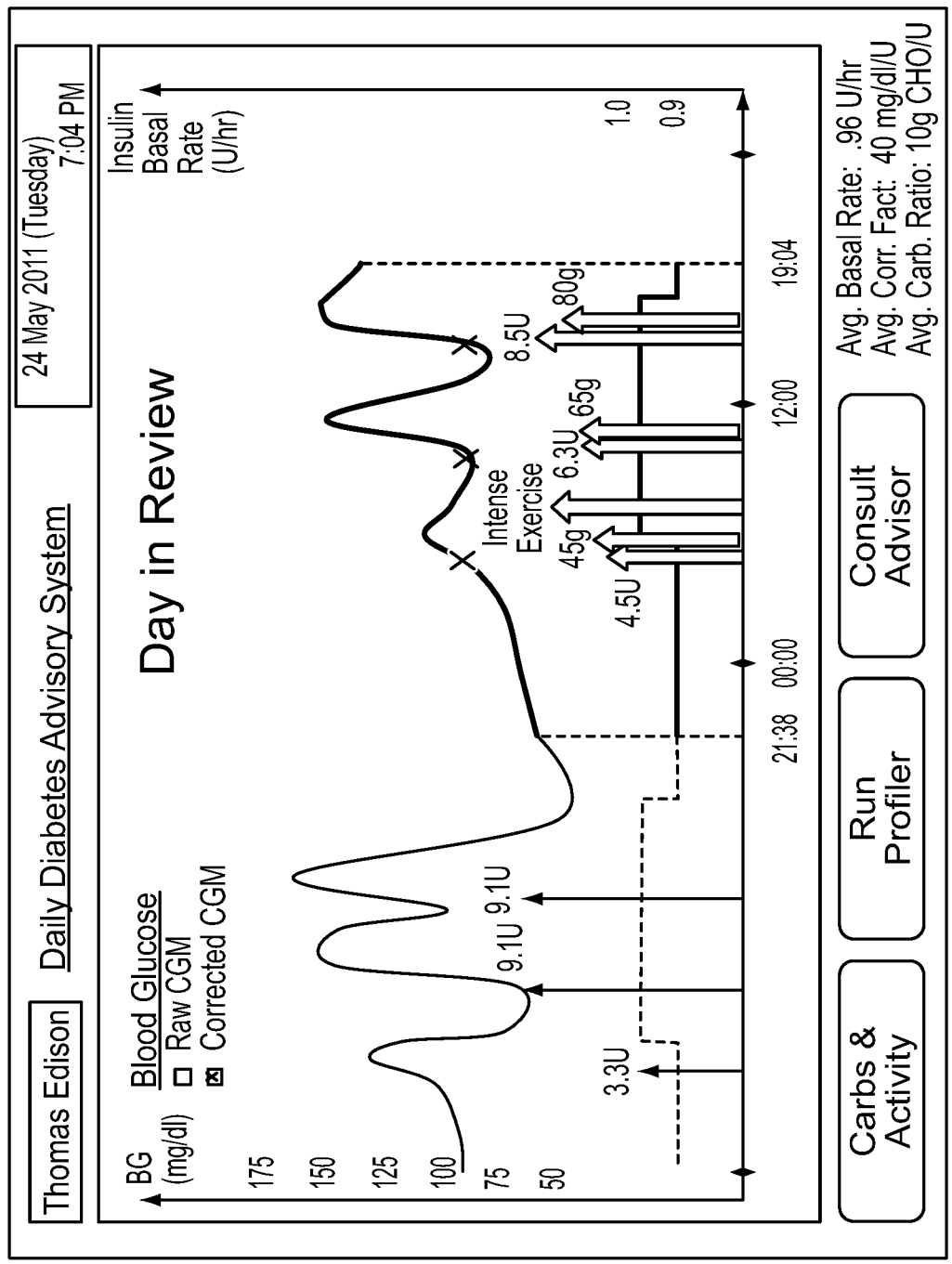
Figure 13:
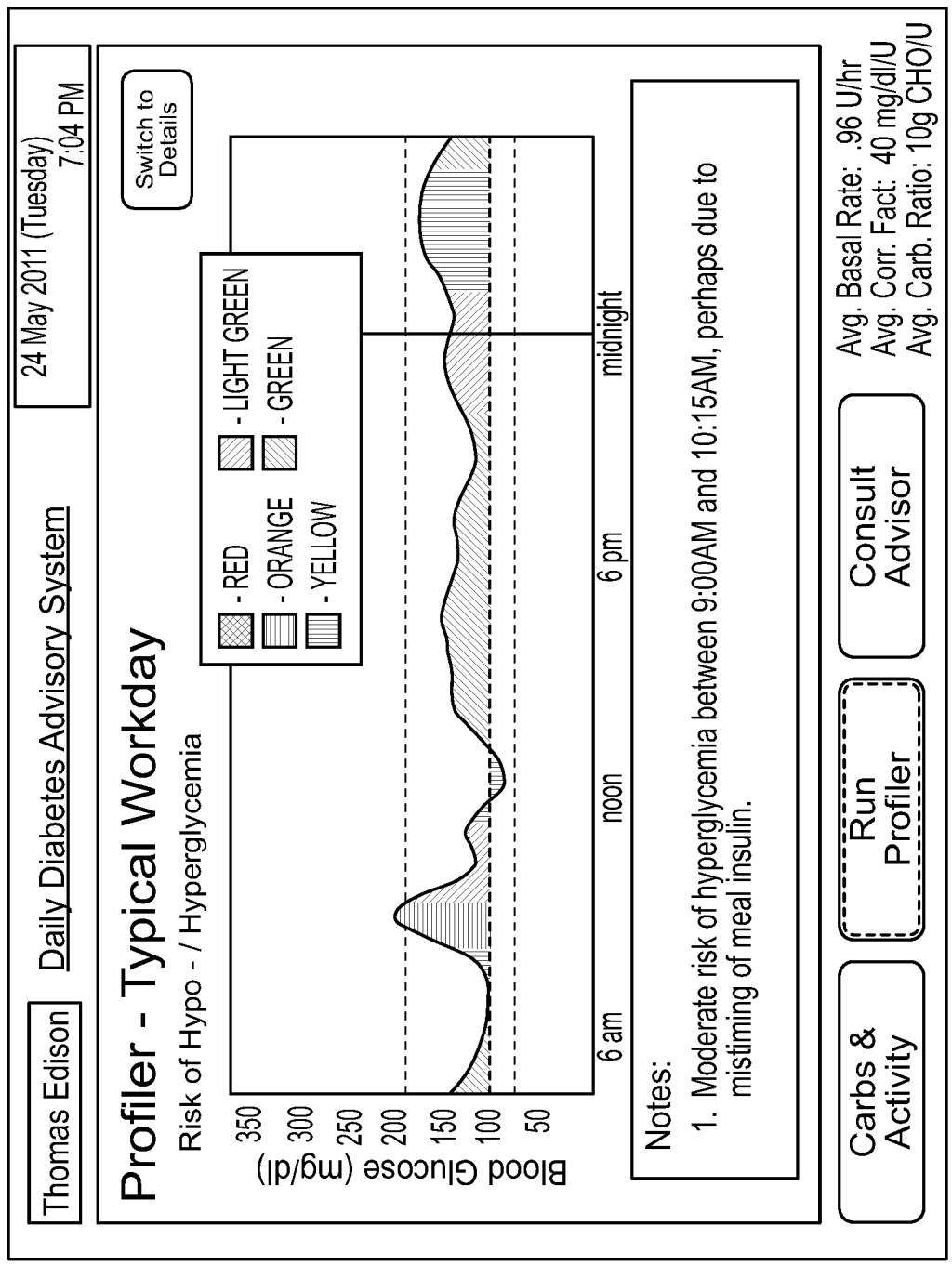
Figure 14:
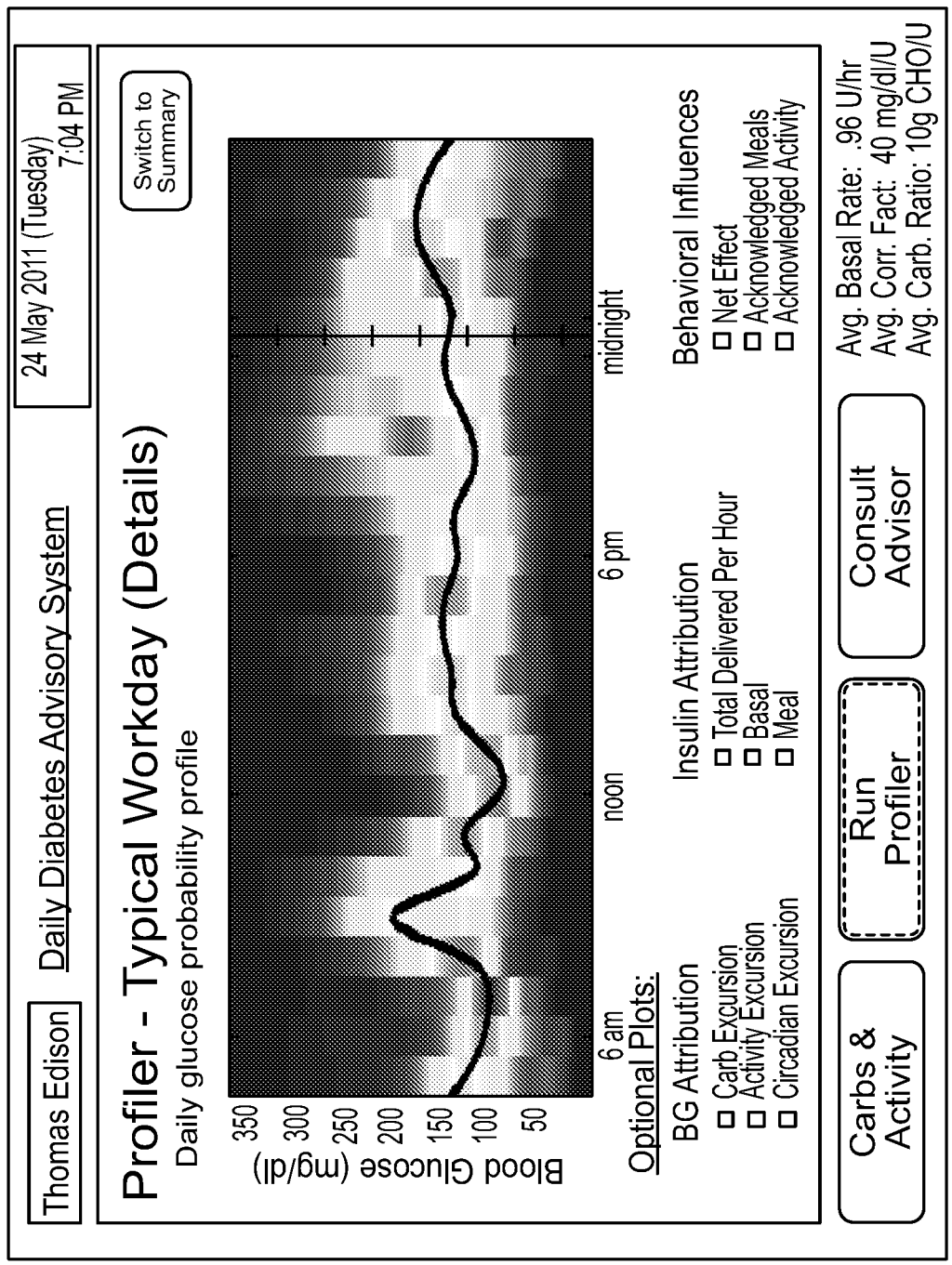
Figure 15:
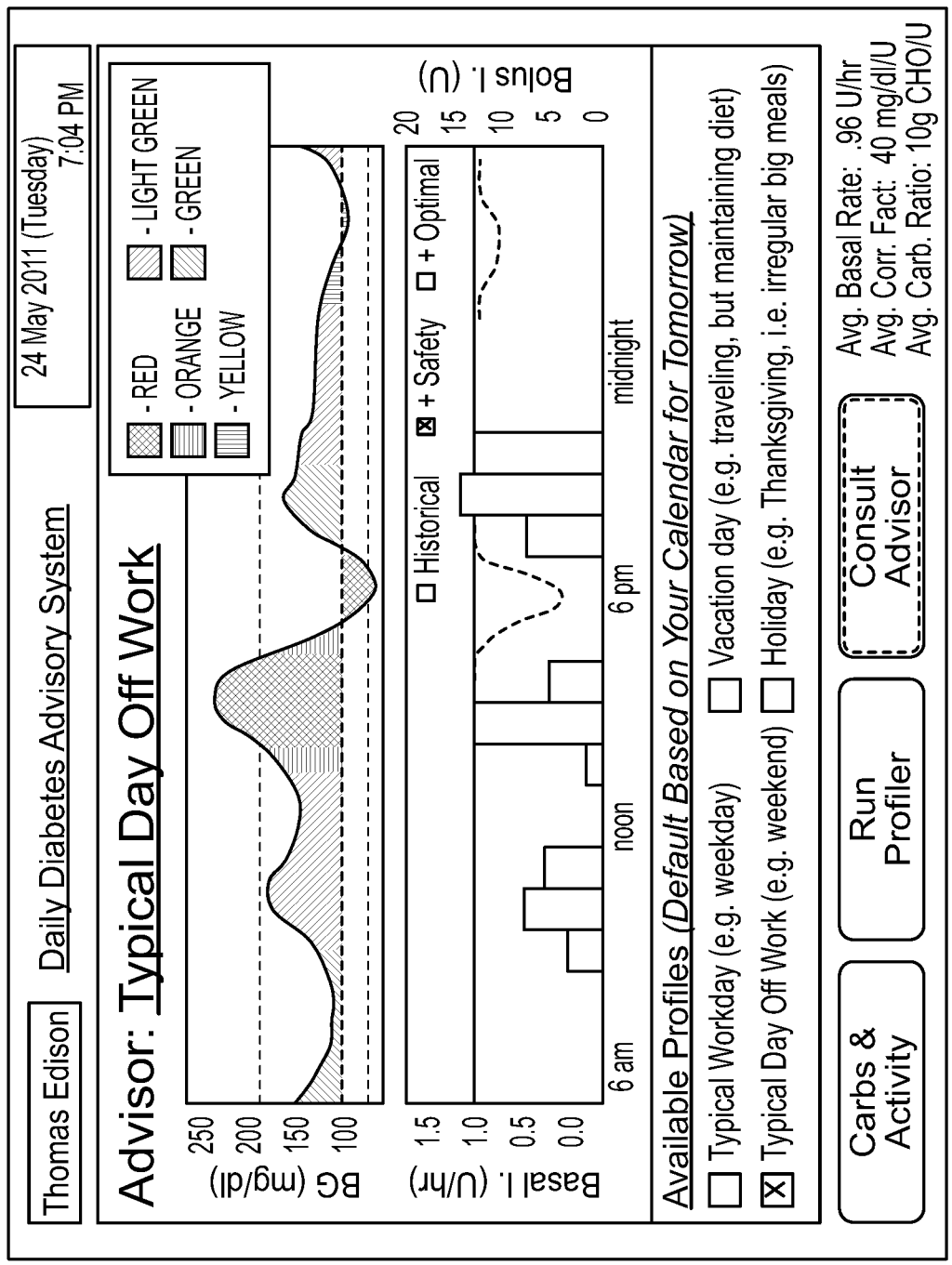

FIGS. 10-15 present screenshots of one possible implementation of the AA system on a personal computer. Similar implementations are possible on a tablet, portable computers (e.g., laptops or notebooks), via Internet applications or network applications, cellular phones, or on a smart phone such as PDAs (with appropriately reduced text and graphs if desired or required). Specifically:

FIG. 10 presents the initialization screen where the system is customized to a particular person;

FIG. 11 provides a screen that presents an opportunity for input of carbohydrate intake (meals) and physical activity by time and amount;

FIG. 12 provides a screen that is a representation of the day in review, including glucose trace and superimposed behaviorally-driven events;

FIGS. 13 and 14 provide screens that present daily profiles at a different level of detail (simple in FIG. 13 and with added probability plots in FIG. 14);

FIG. 15 provides a screen that presents an advisory screen including identified periods of risk for hyper- and hypoglycemia during a typical day off work (shaded red in upper screen panel), and system advice to reduce insulin dose to avoid hypoglycemia (dotted line in lower screen panel).

Figure 16:
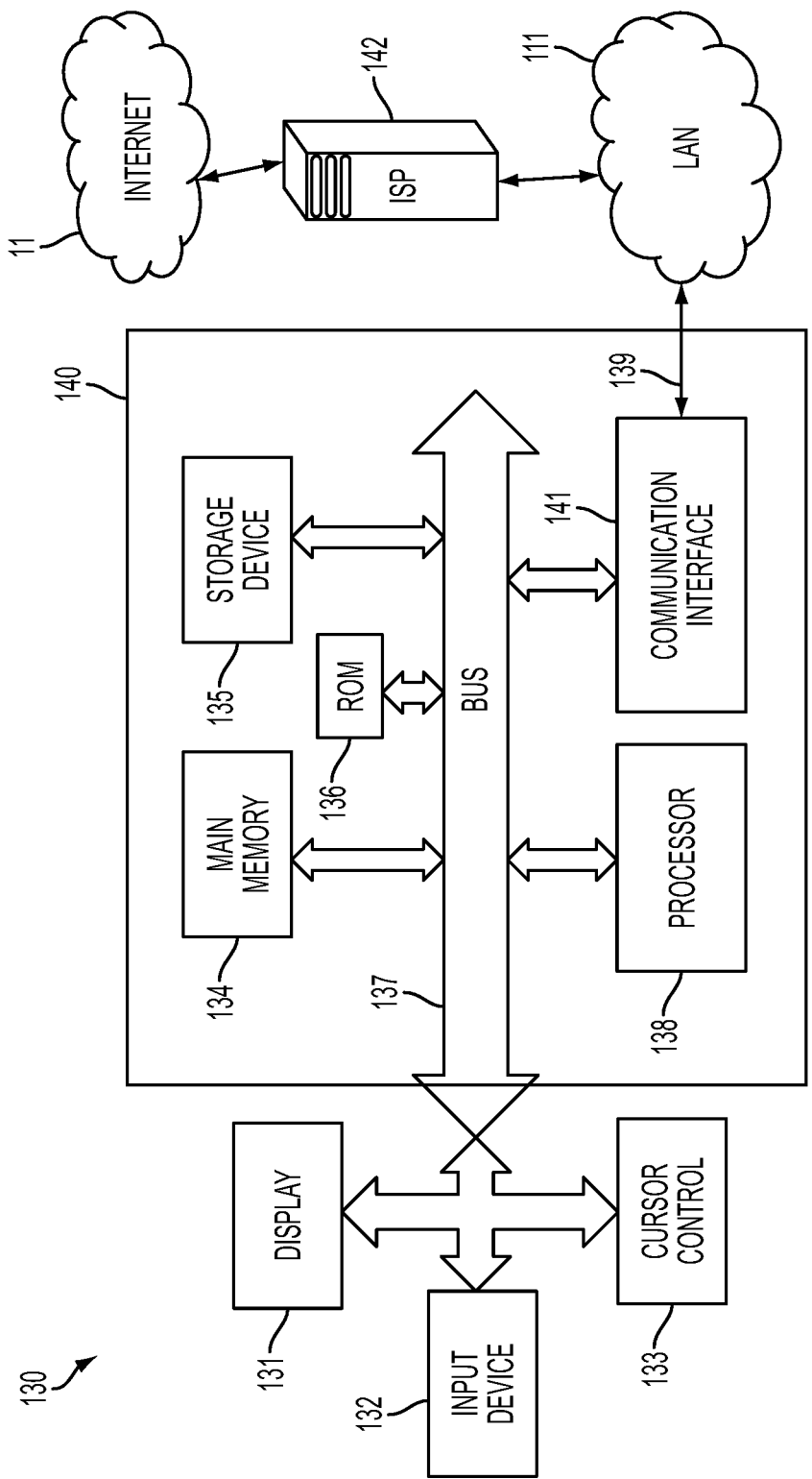
FIG. 16 is a schematic block diagram for a system or related method of an embodiment of the present invention in whole or in part.

FIG. 16 is a block diagram that illustrates a system 130 including a computer system 140 and the associated Internet 11 connection upon which an embodiment may be implemented. Such configuration is typically used for computers (hosts) connected to the Internet 11 and executing a server or a client (or a combination) software. A source computer such as laptop, an ultimate destination computer and relay servers, for example, as well as any computer or processor described herein, may use the computer system configuration and the Internet connection shown in FIG. 16. The system 140 may be used as a portable electronic device such as a notebook/laptop computer, a media player (e.g., MP3 based or video player), a cellular phone, a Personal Digital Assistant (PDA), an image processing device (e.g., a digital camera or video recorder), and/or any other handheld computing devices, or a combination of any of these devices. Note that while FIG. 16 illustrates various components of a computer system, it is not intended to represent any particular architecture or manner of interconnecting the components; as such details are not germane to the present invention. It will also be appreciated that network computers, handheld computers, cell phones and other data processing systems which have fewer components or perhaps more components may also be used. The computer system of FIG. 16 may, for example, be an Apple Macintosh computer or Power Book, or an IBM compatible PC. Computer system 140 includes a bus 137, an interconnect, or other communication mechanism for communicating information, and a processor 138, commonly in the form of an integrated circuit, coupled with bus 137 for processing information and for executing the computer executable instructions. Computer system 140 also includes a main memory 134, such as a Random Access Memory (RAM) or other dynamic storage device, coupled to bus 137 for storing information and instructions to be executed by processor 138.

Main memory 134 also may be used for storing temporary variables or other intermediate information during execution of instructions to be executed by processor 138. Computer system 140 further includes a Read Only Memory (ROM) 136 (or other non-volatile memory) or other static storage device coupled to bus 137 for storing static information and instructions for processor 138. A storage device 135, such as a magnetic disk or optical disk, a hard disk drive for reading from and writing to a hard disk, a magnetic disk drive for reading from and writing to a magnetic disk, and/or an optical disk drive (such as DVD) for reading from and writing to a removable optical disk, is coupled to bus 137 for storing information and instructions. The hard disk drive, magnetic disk drive, and optical disk drive may be connected to the system bus by a hard disk drive interface, a magnetic disk drive interface, and an optical disk drive interface, respectively. The drives and their associated computer-readable media provide non-volatile storage of computer readable instructions, data structures, program modules and other data for the general purpose computing devices. Typically computer system 140 includes an Operating System (OS) stored in a non-volatile storage for managing the computer resources and provides the applications and programs with an access to the computer resources and interfaces. An operating system commonly processes system data and user input, and responds by allocating and managing tasks and internal system resources, such as controlling and allocating memory, prioritizing system requests, controlling input and output devices, facilitating networking and managing files. Non-limiting examples of operating systems are Microsoft Windows, Mac OS X, and Linux.

The term "processor" is meant to include any integrated circuit or other electronic device (or collection of devices) capable of performing an operation on at least one instruction including, without limitation, Reduced Instruction Set Core (RISC) processors, CISC microprocessors, Microcontroller Units (MCUs), CISC-based Central Processing Units (CPUs), and Digital Signal Processors (DSPs). The hardware of such devices may be integrated onto a single substrate (e.g., silicon "die"), or distributed among two or more substrates. Furthermore, various functional aspects of the processor may be implemented solely as software or firmware associated with the processor.

Computer system 140 may be coupled via bus 137 to a display 131, such as a Cathode Ray Tube (CRT), a Liquid Crystal Display (LCD), a flat screen monitor, a touch screen monitor or similar means for displaying text and graphical data to a user. The display may be connected via a video adapter for supporting the display. The display allows a user to view, enter, and/or edit information that is relevant to the operation of the system. An input device 132, including alphanumeric and other keys, is coupled to bus 137 for communicating information and command selections to processor 138. Another type of user input device is cursor control 133, such as a mouse, a trackball, or cursor direction keys for communicating direction information and command selections to processor 138 and for controlling cursor movement on display 131. This input device typically has two degrees of freedom in two axes, a first axis (e.g., x) and a second axis (e.g., y), that allows the device to specify positions in a plane.

The computer system 140 may be used for implementing the methods and techniques described herein. According to one embodiment, those methods and techniques are performed by computer system 140 in response to processor 138 executing one or more sequences of one or more instructions contained in main memory 134. Such instructions may be read into main memory 134 from another computer-readable medium, such as storage device 135. Execution of the sequences of instructions contained in main memory 134 causes processor 138 to perform the process steps described herein. In alternative embodiments, hardwired circuitry may be used in place of or in combination with software instructions to implement the arrangement. Thus, embodiments of the invention are not limited to any specific combination of hardware circuitry and software.

The term "computer-readable medium" (or "machine-readable medium") as used herein is an extensible term that refers to any medium or any memory, that participates in providing instructions to a processor, (such as processor 138) for execution, or any mechanism for storing or transmitting information in a form readable by a machine (e.g., a computer). Such a medium may store computer-executable instructions to be executed by a processing element and/or control logic, and data which is manipulated by a processing element and/or control logic, and may take many forms, including but not limited to, non-volatile medium, volatile medium, and transmission medium. Transmission media includes coaxial cables, copper wire and fiber optics, including the wires that comprise bus 137. Transmission media can also take the form of acoustic or light waves, such as those generated during radio-wave and infrared data communications, or other form of propagated signals (e.g., carrier waves, infrared signals, digital signals, etc.). Common forms of computer-readable media include, for example, a floppy disk, a flexible disk, hard disk, magnetic tape, or any other magnetic medium, a CD-ROM, any other optical medium, punch-cards, paper-tape, any other physical medium with patterns of holes, a RAM, a PROM, and EPROM, a FLASH-EPROM, any other memory chip or cartridge, a carrier wave as described hereinafter, or any other medium from which a computer can read.

Various forms of computer-readable media may be involved in carrying one or more sequences of one or more instructions to processor 138 for execution. For example, the instructions may initially be carried on a magnetic disk of a remote computer. The remote computer can load the instructions into its dynamic memory and send the instructions over a telephone line using a modem. A modem local to computer system 140 can receive the data on the telephone line and use an infra-red transmitter to convert the data to an infra-red signal. An infra-red detector can receive the data carried in the infra-red signal and appropriate circuitry can place the data on bus 137. Bus 137 carries the data to main memory 134, from which processor 138 retrieves and executes the instructions. The instructions received by main memory 134 may optionally be stored on storage device 135 either before or after execution by processor 138.

Computer system 140 also includes a communication interface 141 coupled to bus 137. Communication interface 141 provides a two-way data communication coupling to a network link 139 that is connected to a local network 111. For example, communication interface 141 may be an Integrated Services Digital Network (ISDN) card or a modem to provide a data communication connection to a corresponding type of telephone line. As another non-limiting example, communication interface 141 may be a local area network (LAN) card to provide a data communication connection to a compatible LAN. For example, Ethernet based connection based on IEEE802.3 standard may be used such as 10/100BaseT, 1000BaseT (gigabit Ethernet), 10 gigabit Ethernet (10 GE or 10 GbE or 10 GigE per IEEE Std 802.3ae-2002 as standard), 40 Gigabit Ethernet (40 GbE), or 100 Gigabit Ethernet (100 GbE as per Ethernet standard IEEE P802.3ba), as described in Cisco Systems, Inc. Publication number 1-587005-001-3 (June 1999), "Internetworking Technologies Handbook", Chapter 7: "Ethernet Technologies", pages 7-1 to 7-38, which is incorporated in its entirety for all purposes as if fully set forth herein. In such a case, the communication interface 141 typically include a LAN transceiver or a modem, such as Standard Microsystems Corporation (SMSC) LAN91C111 10/100 Ethernet transceiver described in the Standard Microsystems Corporation (SMSC) data-sheet "LAN91C111 10/100 Non-PCI Ethernet Single Chip MAC+PHY" Data-Sheet, Rev. 15 (Feb. 20, 2004), which is incorporated in its entirety for all purposes as if fully set forth herein.

Wireless links may also be implemented. In any such implementation, communication interface 141 sends and receives electrical, electromagnetic or optical signals that carry digital data streams representing various types of information.

Network link 139 typically provides data communication through one or more networks to other data devices. For example, network link 139 may provide a connection through local network 111 to a host computer or to data equipment operated by an Internet Service Provider (ISP) 142. ISP 142 in turn provides data communication services through the world wide packet data communication network Internet 11. Local network 111 and Internet 11 both use electrical, electromagnetic or optical signals that carry digital data streams. The signals through the various networks and the signals on the network link 139 and through the communication interface 141, which carry the digital data to and from computer system 140, are exemplary forms of carrier waves transporting the information.

A received code may be executed by processor 138 as it is received, and/or stored in storage device 135, or other non-volatile storage for later execution. In this manner, computer system 140 may obtain application code in the form of a carrier wave.

The concept of retroactively assessing risk of hypoglycemia, retroactively assessing risk-based reduction of insulin delivery, and reporting the same on how to prevent hypoglycemia as well as enjoying other related benefits, may be implemented and utilized with the related processors, networks, computer systems, internet, and components and functions according to the schemes disclosed herein.

PUBLICATIONS

The following patents, applications and publications as listed below and throughout this document are hereby incorporated by reference in their entirety herein, and which are not admitted to be prior art with respect to the present invention by inclusion in this section.

1. Albisser A M, Leibel B S, Ewart T G, Davidovac Z, Botz C K, Zinggg W. An artificial endocrine pancreas. *Diabetes*, 23:389-396, 1974.
2. Bellazzi R, Nucci G, Cobelli C: The subcutaneous route to insulin-dependent diabetes therapy: closed-loop and partially closed-loop control strategies for insulin delivery and measuring glucose concentration. *IEEE Eng Med Biol* 22: 54-64, 2001.
3. Bequette B W. Analysis of Algorithms for Intensive Care Unit Blood Glucose Control. *J Diabetes Sci Technol*, 1: 813-824, 2007.
4. Bergman R N, Ider Y Z, Bowden C R, Cobelli C. Quantitative estimation of insulin sensitivity. *Am J Physiol*. 236: E667-E677, 1979.
5. Boyne M, Silver D, Kaplan J, and Saudek C: Timing of Changes in Interstitial and Venous Blood Glucose Measured With a Continuous Subcutaneous Glucose Sensor. *Diabetes*, 52:2790-2794, 2003.
6. Broekhuyse H M, Nelson J D, Zinman B, and Albisser A M: Comparison of algorithms for the closed-loop control of blood glucose using the artificial beta cell. *IEEE Trans Biomed Eng BME*-28: 678-687, 1981.
7. Brunetti P., Cobelli C., Cruciani P., Fabietti P. G., Filippucci F., Santeusanio F.: A simulation study on a self-tuning portable controller of blood glucose. *Int J Artificial Organs* 16: 51-57, 1993.
8. Clarke W L and Kovatchev B P. The Artificial Pancreas: How Close We Are to Closing the Loop? *Ped Endocrinol Rev*, 4: 314-316, 2007.
9. Clarke W L, Cox D J, Gonder-Frederick L A, Julian D M, Kovatchev B P, Young-Hyman D. The bio-psycho-behavioral model of severe hypoglycemia II: Self-management behaviors. *Diabetes Care* 22: 580-584, 1999.
10. Clemens A H, Chang P H, Myers R W. The development of Biostator, a glucose-controlled insulin infusion system. *Horm Metab Res Supplement*, 7: 23-33, 1977.
11. Clemens A H: Feedback control dynamics for glucose controlled insulin infusion system. *MedProg Technol* 6: 91-98, 1979.

12. Cobelli C and Kovatchev B P. Clinical Trial of Model-Predictive Control Powered by In Silico Studies. *Proc. 8th Diabetes Technology Meeting*, Bethesda, Md., 2008.
13. Cobelli C, Ruggeri A: Evaluation of portal/peripheral route and of algorithms for insulin delivery in the closed-loop control of glucose in diabetes. A modelling study. *IEEE Trans Biomed Eng* 30: 93-103, 1983.
14. Cryer P E, Davis S N, Shamoon H. Hypoglycemia in Diabetes. *Diabetes Care*, 26: 1902-1912, 2003.
15. Cryer P E. Hypoglycaemia: The limiting factor in the glycaemic management of type I and type II diabetes. *Diabetologia* 45: 937-948, 2002.
16. Cryer P E. Iatrogenic hypoglycemia as a cause of hypoglycemia-associated autonomic failure in IDDM: A vicious cycle. *Diabetes* 41:255-260, 1992.
17. Cryer P E: Hypoglycemia: The Limiting factor in the management of IDDM. *Diabetes* 43: 1378-1389, 1994.
18. Dassau E, Bequette B W, Buckingham B A, Doyle F J 3rd. Detection of a meal using continuous glucose monitoring: implications for an artificial beta-cell. *Diabetes Care*, 31:295-300, 2008.
19. Dassau E, Cameron F, Neimeyer G, Chase P, Buckingham B. Real-time Hypoglycemic Prediction Using Continuous Glucose Monitoring (CGM). *Diabetes*, 57 Suppl 1, 2008.
20. Dua P, Doyle F J 3rd, Pistikopoulos E N. "Model-Based Blood Glucose Control for Type 1 Diabetes via Parametric Programming." *IEEE Trans Biomed Eng.* 53:1478-1491, 2006.
21. E W, Campbell L V, Chia Y O, Meler H, and Lazarus L: Control of blood glucose in diabetics using an artificial pancreas. *Aust N Z J Med* 7: 280-286, 1977.
22. Fischer U, Jutzi E, Freyse E-J, and Salzsieder E: Derivation and experimental proof of a new algorithm for the artificial beta-cell based on the individual analysis of the physiological insulin-glucose relationship. *Endokrinologie* 71:65-75, 1978.
23. Fischer U, Schenk W, Salzsieder E, Albrecht G, Abel P, and Freyse E-J: Does physiological blood glucose control require an adaptive strategy? *IEEE Trans Biomed Eng* 34:575-582, 1987.
24. Fisher M E: A semi closed-loop algorithm for the control of blood glucose levels in diabetics. *IEEE Trans Biomed Eng* 38: 57-61, 1991.
25. Gold A E, Deary I J, Frier B M. Recurrent severe hypoglycaemia and cognitive function in type I diabetes. *Diabet Med* 10:503-508, 1993.
26. Gonder-Frederick L, Cox D, Kovatchev B, Schlundt D, Clarke W. A biopsychobehavioral model of risk of severe hypoglycemia. *Diabetes Care*, 20:661-669, 1997.
27. Hovorka R, Canonico V, Chassin L J, et al. Nonlinear model predictive control of glucose concentration in subjects with type 1 diabetes. *Physiol Meas* 25:905-920, 2004.
28. Hovorka R, Chassin L J, Wilinska M E, et al. Closing the loop: the ADICOL experience. *Diabetes Technol Ther.* 6: 307-318, 2004.
29. Hovorka R: Continuous glucose monitoring and closed-loop systems. *Diabet Med* 2: 1-12, 2006.
30. Hughes C S, S. D. Patek S D, M. Breton M D, and B P Kovatchev. Hypoglycemia Prevention via Pump Attenuation and Red-Yellow-Green "Traffic" Lights using CGM and Insulin Pump Data, *J Diab Sci and Tech*, 4: 1146-1155, 2010.
31. Klonoff D C: The Artificial Pancreas: How Sweet Engineering Will Solve Bitter Problems. *J Diabetes Sci Technol*, 1: 72-81, 2007.
32. Kovatchev B P, Clarke W L. Continuous glucose monitoring reduces risks for hypo- and hyperglycemia and glucose variability in diabetes. *Diabetes*, 56, Supplement 1: 0086OR, 2007.
33. Kovatchev B P, Cox D J, Farhy L S, Straume M, Gonder-Frederick L A, Clarke, W L. Episodes of Severe Hypoglycemia in Type 1 Diabetes are Preceded, and Followed, within 48 Hours by Measurable Disturbances in Blood Glucose. *J of Clinical Endocrinology and Metabolism*, 85: 4287-4292, 2000.
34. Kovatchev B P, Cox D J, Gonder-Frederick L A, and W L Clarke. Symmetrization of the blood glucose measurement scale and its applications, *Diabetes Care*, 20: 1655-1658, 1997.
35. Kovatchev B P, Straume M, Cox D J, Farhy L S. Risk analysis of blood glucose data: A quantitative approach to optimizing the control of insulin dependent diabetes. *J of Theoretical Medicine*, 1:1-10, 2001.
36. Kulcu E, Tamada J A, Reach G, Potts R O, Lesho M J: Physiological differences between interstitial glucose and blood glucose measured in human subjects. *Diabetes Care*, 26:2405-2409, 2003.
37. Leblanc H, Chauvet D, Lombrail P, Robert J J: Glycemic control with closed-loop intraperitoneal insulin in type I diabetes. *Diabetes Care*, 9: 124-128, 1986.
38. Magni L, Raimondo F, Bossi L, Dalla Man C, De Nicolao G, Kovatchev B P, Cobelli C. Model Predictive Control of Type 1 Diabetes: An In Silico Trial *J Diabetes Sci Technol*, 1: 804-812, 2007.
39. Marliss E B, Murray F T, Stokes E F, Zinman B, Nakhooda A F, Denoga A, Leibel B S, and Albisser A M: Normalization of glycemia in diabetics during meals with insulin and glucagon delivery by the artificial pancreas. *Diabetes* 26: 663-672, 1977.
40. Nucci G., Cobelli C. Models of subcutaneous insulin kinetics. A critical review. Comput Methods Programs Biomed., 62:249-57 Review, 2000.
41. Ollerton R L: Application of optimal control theory to diabetes mellitus. *Int J Control* 50: 2503-2522, 1989.
42. Owens C, Zisser H, Jovanovic L, Srinivasan B, Bonvin D, Doyle F J 3rd. Run-to-run control of glucose concentrations for people with Type 1 diabetes mellitus. *IEEE Trans Biomed Eng.* 53:996-1005, 2006.
43. Palerm C C, Zisser H, Bevier W C, Jovanovic L, Doyle F J 3rd. Prandial insulin dosing using run-to-run control: application of clinical data and medical expertise to define a suitable performance metric. *Diabetes Care.* 3: 1131-1136, 2007.
44. Palerm C C, Zisser H, Jovanovič, Doyle F J 3rd. A Run-to-Run Control Strategy to Adjust Basal Insulin Infusion Rates in Type 1 Diabetes. *J Process Control.* 18:258-265, 2008.
45. Parker R S, Doyle F J 3rd, Peppas N A. A model-based algorithm for blood glucose control in Type I diabetic patients. *IEEE Trans Biomed Eng*, 48:148-157, 1999.
46. Patek S D, Breton M D, Cobelli C, Dalla Man C, and Kovatchev B P. Adaptive meal detection algorithm enabling closed-loop control in type 1 diabetes. *Proc. 7th Diabetes Technology Meeting*, San Francisco, Calif., 2007.
47. Patek S D. Open-Loop Feedback Control under Multiple Disturbance Function Hypotheses, Proc. of the IEEE Conference on Decision and Control, 2010, Atlanta.
48. Pfeiffer E F, Thum Ch, and Clemens A H: The artificial beta cell—A continuous control of blood sugar by external regulation of insulin infusion (glucose controlled insulin infusion system). *Horm Metab Res* 487: 339-342, 1974.
49. Reichard P, Phil M. Mortality and treatment side effects during long-term intensified conventional insulin treatment in the Stockholm Diabetes Intervention study. *Diabetes* 43: 313-317, 1994.
50. Reifman J, Rajaraman S, Gribok A, Ward W K. Predictive monitoring for improved management of glucose levels. *J Diabetes Sci Technol* 1: 478-486, 2007.
51. Renard E: Implantable closed-loop glucose-sensing and insulin delivery: the future for insulin pump therapy, *Current Opinion in Pharmacology,* 2: 708-716, 2002.
52. Salzsieder E, Albrecht G, Fischer U, and Freyse E-J: Kinetic modeling of the gluco-regulatory system to improve insulin therapy. *IEEE Trans Biomed Eng* 32: 846-855, 1985.
53. Santiago J V, Clemens A H, Clarke W L, Kipnis D M. Closed-loop and open-loop devices for blood glucose control in normal and diabetic subjects. *Diabetes,* 28: 71-84, 1979.
54. Schaller H C, Schaupp L, Bodenlenz M, Wilinska M E, Chassin L J, Wach P, Vering T, Hovorka R, Pieber T R: On-line adaptive algorithm with glucose prediction capacity for subcutaneous closed loop control of glucose: evaluation under fasting conditions in patients with Type 1 diabetes. *Diabet Med* 23:90-93, 2006.
55. Selam J L, Micossi P, Dunn F L, and Nathan D M: Clinical trial of programmable implantable insulin pump for type I diabetes, *Diabetes Care* 15: 877-885, 1992.
56. Sorensen J T: A Physiologic Model of Glucose Metabolism in Man and its Use to Design and Assess Improved Insulin Therapies for Diabetes, Ph.D. dissertation, Dept Chemical Engineering, MIT, 1985.
57. Sparacino G, Zanderigo F, Corazza G, Maran A, Facchinetti A, Cobelli C. Glucose concentration can be predicted ahead in time from continuous glucose monitoring sensor time-series. *IEEE Trans Biomed Eng,* 54:931-937, 2007.
58. Steil G M, Rebrin K, Darwin C, Hariri F, Saad M F. Feasibility of automating insulin delivery for the treatment of type 1 diabetes. *Diabetes* 55: 3344-3350, 2006.
59. Stout P J, Racchini J R, Hilgers M E: A Novel Approach to Mitigating the Physiological Lag between Blood and Interstitial Fluid Glucose Measurements. *Diabetes Technol Ther,* 6:635-644, 2004.
60. The Diabetes Control and Complications Trial Research Group. Hypoglycemia in the Diabetes Control and Complications Trial. *Diabetes* 46: 271-286, 1997.
61. The Diabetes Control and Complications Trial Research Group. The effect of intensive treatment of diabetes on the development and progression of long-term complications of insulin-dependent diabetes mellitus. *N Engl J Med* 329: 978-986, 1993.
62. Weinzimer S A, Steil G M, Swan K L, Dziura J, Kurtz N, Tamborlane W V: Fully automated closed-loop insulin delivery versus semi-automated hybrid control in pediatric patients with type 1 diabetes using an artificial pancreas. *Diabetes Care* 31:934-939, 2008.
63. Wentholt I M E, Hart A A M, Hoekstra J B L, DeVries J H. Relationship Between Interstitial and Blood Glucose in Type 1 Diabetes Patients: Delay and the Push-Pull Phenomenon Revisited. *Diabetes Technol Ther,* 9:169-175, 2004.
64. Wilinska M E, Chassin L J, Schaller H C, Schaupp L, Pieber T R, Hovorka R. Insulin kinetics in type-1 diabetes: continuous and bolus delivery of rapid acting insulin. *IEEE Trans. Biomed. Eng.* 52:3-12, 2005.
65. Zanderigo F, Sparacino G, Kovatchev B, Cobelli C. Glucose Prediction Algorithms from continuous monitoring: Assessment of accuracy via Continuous Glucose-Error Grid Analysis. *J Diabetes Sci Technol,* 1: 645-651, 2007
66. Zisser H, Jovanovic L, Doyle F J 3rd, Ospina P, Owens C. Run-to-Run Control of Meal-Related Insulin Dosing. *Diab Technol Ther* 2:48-57, 2005.
67. C. S. Hughes, S. D. Patek, A. Taylor, R. Park, K. Laub-scher, S. Pillutla, M. Breton, and B. P. Kovatchev. In-silico experiments of human eating patterns: Making a case for behavior-informed control of T1DM. In Proc. UKACC International Conference of Control, 2010.

REFERENCES

The devices, systems, computer readable medium, and methods of various embodiments of the invention disclosed herein may utilize aspects disclosed in the following references, applications, publications and patents and which are hereby incorporated by reference herein in their entirety, and which are not admitted to be prior art with respect to the present invention by inclusion in this section:
A. International Patent Application Serial No. PCT/US2012/043910, Kovatchev, et al., "Unified Platform For Monitoring and Control of Blood Glucose Levels in Diabetic Patients", filed Jun. 23, 2012.
B. International Patent Application Serial No. PCT/US2012/043883, Kovatchev, et al., "Methods and Apparatus for Modular Power Management and Protection of Critical Services in Ambulatory Medical Devices", filed Jun. 22, 2012.
C. International Patent Application Serial No. PCT/US2011/029793, Kovatchev et al., entitled Method, System, and Computer Program Product for Improving the Accuracy of Glucose Sensors Using Insulin Delivery Observation in Diabetes," filed Mar. 24, 2011
D. PCT/US2011/028163, Breton, et al., entitled "Method and System for the Safety, Analysis and Supervision of Insulin Pump Action and Other Modes of Insulin Delivery in Diabetes", filed Mar. 11, 2011.
E. International Patent Application Serial No. PCT/US2010/047711, Kovatchev, et al., "Tracking the Probability for Imminent Hypoglycemia in Diabetes from Self-Monitoring Blood Glucose (SMBG) Data", filed Sep. 2, 2010.
F. International Patent Application Serial No. PCT/US2010/047386, Kovatchev, et al., "System, Method and Computer Program Product for Adjustment of Insulin Delivery (AID) in Diabetes Using Nominal Open-Loop Profiles", filed Aug. 31, 2010.
G. International Patent Application Serial No. PCT/US2010/040097, Kovatchev, et al., "System, Method, and Computer Simulation Environment for In Silico Trials in Prediabetes and Type 2 Diabetes", filed Jun. 25, 2010.
H. International Patent Application Serial No. PCT/US2010/036629, Kovatchev, et al., "System Coordinator and Modular Architecture for Open-Loop and Closed-Loop Control of Diabetes", filed May 28, 2010 (Publication No. WO 2010/138848, Dec. 2, 2010).
I. International Patent Application Serial No. PCT/US2010/025405, Kovatchev, et al., entitled "Method, System and Computer Program Product for CGM-Based Prevention of Hypoglycemia via Hypoglycemia Risk Assessment and Smooth Reduction Insulin Delivery," filed Feb. 25, 2010.
J. International Patent Application Serial No. PCT/US2009/065725, Kovatchev, et al., filed Nov. 24, 2009, entitled "Method, System, and Computer Program Product for Tracking of Blood Glucose Variability in Diabetes from Data."

K. International Patent Application Serial No. PCT/US2008/082063, Magni, et al., entitled "Model Predictive Control Based Method for Closed-Loop Control of Insulin Delivery in Diabetes Using Continuous Glucose Sensing", filed Oct. 31, 2008; U.S. patent application Ser. No. 12/740,275, Magni, et al., entitled "Predictive Control Based System and Method for Control of Insulin Delivery in Diabetes Using Glucose Sensing", filed Apr. 28, 2010.

L. International Patent Application Serial No. PCT/US2008/069416, Breton, et al., entitled "Method, System and Computer Program Product for Evaluation of Insulin Sensitivity, Insulin/Carbohydrate Ratio, and Insulin Correction Factors in Diabetes from Self-Monitoring Data", filed Jul. 8, 2008, (Publication No. WO 2009/009528, Jan. 15, 2009); U.S. patent application Ser. No. 12/665,149, Breton, et al., "Method, System and Computer Program Product for Evaluation of Insulin Sensitivity, Insulin/Carbohydrate Ratio, and Insulin Correction Factors in Diabetes from Self-Monitoring Data", filed Dec. 17, 2009.

M. International Patent Application Serial No. PCT/US2008/067725, Kovatchev, et al., entitled "Method, System and Computer Simulation Environment for Testing of Monitoring and Control Strategies in Diabetes," filed Jun. 20, 2008, (Publication No. WO 2008/157781, Dec. 24, 2008); U.S. patent application Publication Ser. No. 12/664,444, Kovatchev, et al., filed Dec. 14, 2009, entitled "Method, System and Computer Simulation Environment for Testing of Monitoring and Control Strategies in Diabetes", (Publication No. 2010/0-179768, Jul. 15, 2010).

N. International Patent Application Serial No. PCT/US2008/067723, Patek, et al., entitled "LQG Artificial Pancreas Control System and Related Method", filed on Jun. 20, 2008.

O. U.S. patent application Ser. No. 12/516,044, Kovatchev, et al., filed May 22, 2009, entitled "Method, System, and Computer Program Product for the Detection of Physical Activity by Changes in Heart Rate, Assessment of Fast Changing Metabolic States, and Applications of Closed and Open Control Loop in Diabetes".

P. International Patent Application Serial No. PCT/US2007/085588, Kovatchev, et al., filed Nov. 27, 2007, entitled "Method, System, and Computer Program Product for the Detection of Physical Activity by Changes in Heart Rate, Assessment of Fast Changing Metabolic States, and Applications of Closed and Open Control Loop in Diabetes", (Publication No. WO2008/067284, Jun. 5, 2008)

Q. U.S. patent application Ser. No. 11/943,226, Kovatchev, et al., filed Nov. 20, 2007, entitled "Systems, Methods and Computer Program Codes for Recognition of Patterns of Hyperglycemia and Hypoglycemia, Increased Glucose Variability, and Ineffective Self-Monitoring in Diabetes".

R. U.S. patent application Ser. No. 11/578,831, Kovatchev, et al., filed Oct. 18, 2006 entitled "Method, System and Computer Program Product for Evaluating the Accuracy of Blood Glucose Monitoring Sensors/Devices", (Publication No. US2007/0232878, Oct. 4, 2007), U.S. Pat. No. 7,815,569, Kovatchev, et al., issued Oct. 29, 2010

S. International Application Serial No. PCT/US2005/013792, Kovatchev, et al., filed Apr. 21, 2005, entitled "Method, System, and Computer Program Product for Evaluation of the Accuracy of Blood Glucose Monitoring Sensors/Devices", (Publication No. WO 05106017, Nov. 10, 2005

T. International Patent Application Serial No. PCT/US01/09884, Kovatchev, et al., filed Mar. 29, 2001, entitled "Method, System, and Computer Program Product for Evaluation of Glycemic Control in Diabetes Self-Monitoring Data", (Publication No. WO 01/72208, Oct. 4, 2001).

U. U.S. patent application Ser. No. 10/240,228, Kovatchev, et al., filed Sep. 26, 2002, (Publication No. 0212317, Nov. 13, 2003), U.S. Pat. No. 7,025,425 B2, Kovatchev, et al., issued Apr. 11, 2006, entitled "Method, System, and Computer Program Product for the Evaluation of Glycemic Control in Diabetes from Self-Monitoring Data".

V. U.S. patent application Ser. No. 11/305,946, Kovatchev, et al., filed Dec. 19, 2005 entitled "Method, System, and Computer Program Product for the Evaluation of Glycemic Control in Diabetes from Self-Monitoring Data" (Publication No. 2006/0094947, May 4, 2006), U.S. Pat. No. 7,874,985, Kovatchev, et al., issued Jan. 25, 2011.

W. U.S. patent application Ser. No. 12/975,580, Kovatchev, et al., "Method, System, and Computer Program Product for the Evaluation of Glycemic Control in Diabetes from Self-Monitoring Data", filed Dec. 22, 2010.

X. International Patent Application Serial No. PCT/US2003/025053, Kovatchev, et al., filed Aug. 8, 2003, entitled "Method, System, and Computer Program Product for the Processing of Self-Monitoring Blood Glucose (SMBG) Data to Enhance Diabetic Self-Management", (Publication No. WO 2004/015539, Feb. 19, 2004).

Y. U.S. patent application Ser. No. 10/524,094, Kovatchev, et al., filed Feb. 9, 2005 entitled "Managing and Processing Self-Monitoring Blood Glucose" (Publication No. 2005/214892, Sep. 29, 2005).

Z. U.S. patent application Ser. No. 12/065,257, Kovatchev, et al., filed Aug. 29, 2008, entitled "Accuracy of Continuous Glucose Sensors", (Publication No. 2008/0314395, Dec. 25, 2008).

AA. International Patent Application Serial No PCT/US2006/033724, Kovatchev, et al., filed Aug. 29, 2006, entitled "Method for Improvising Accuracy of Continuous Glucose Sensors and a Continuous Glucose Sensor Using the Same", (Publication No. WO 07027691, Mar. 8, 2007).

BB. U.S. patent application Ser. No. 12/159,891, Kovatchev, B., filed Jul. 2, 2008, entitled "Method, System and Computer Program Product for Evaluation of Blood Glucose Variability in Diabetes from Self-Monitoring Data", (Publication No. 2009/0171589, Jul. 2, 2009).

CC. International Application No. PCT/US2007/000370, Kovatchev, B., filed Jan. 5, 2007, entitled "Method, System and Computer Program Product for Evaluation of Blood Glucose Variability in Diabetes from Self-Monitoring Data", (Publication No. WO 07081853, Jul. 19, 2007).

DD. U.S. patent application Ser. No. 11/925,689 and PCT International Patent Application No. PCT/US2007/082744, Breton, et al., both filed Oct. 26, 2007, entitled "For Method, System and Computer Program Product for Real-Time Detection of Sensitivity Decline in Analyte Sensors", (Publication Nos. 2008/0172205, Jul. 17, 2008 and WO 2008/052199, May 2, 2008).

EE. U.S. patent application Ser. No. 10/069,674, Kovatchev, et al., filed Feb. 22, 2002, entitled "Method and Apparatus for Predicting the Risk of Hypoglycemia".

FF. International Application No. PCT/US00/22886, Kovatchev, et al., filed Aug. 21, 2000, entitled "Method and Apparatus for Predicting the Risk of Hypoglycemia", (Publication No. WO 01/13786, Mar. 1, 2001).

GG. U.S. Pat. No. 6,923,763 B1, Kovatchev, et al., issued Aug. 2, 2005, entitled "Method and Apparatus for Predicting the Risk of Hypoglycemia".

HH. U.S. Patent Application Publication No. US 2004/0254434 A1, "Glucose Measuring Module and "Insulin Pump Combination", published Dec. 16, 2004, Goodnow, et al. Ser. No. 10/458,914, filed Jun. 10, 2003.

II. U.S. Patent Application Publication No. US 2009/00697456 A1, Estes, et al., "Operating an Infusion Pump System", published Mar. 12, 2009. Ser. No. 11/851,194, Sep. 6, 2007.

JJ. Fernandez-Luque, et al., eDiab: A System for Monitoring, Assisting and Educating People with Diabetes", ICCHP 2006, LNCS 4061, pp. 1342-1349, 2006.

KK. U.S. Pat. No. 6,602,191 B2, Quy, R., Method and Apparatus for Health and Disease Management Combining Patient Data Monitoring with Wireless Internet Connectivity, Aug. 5, 2003.

LL. International Patent Application Publication No. WO 2008/064053 A2, Patel, et al., Systems and Methods for Diabetes Management Using Consumer Electronic Devices, May 29, 2008; International Patent Application Serial No. PCT/US2007/084769, filed Nov. 15, 2007.

MM. International Patent Application Publication No. WO 2010/138817 A1, Ow-Wing, K., Glucose Monitoring System with Wireless Communications, Dec. 2, 2010; International Patent Application Serial No. WO 2010/138817 A1, filed May 28, 2010.

NN. International Patent Application Publication No. WO 2004/052204 A1, Kim, Kwan-Ho, Blood Glucose Monitoring System, Jun. 24, 2004; International Patent Application Serial No. PCT/KR2003/000398, filed Feb. 28, 2003.

EXAMPLES

Practice of an aspect of an embodiment (or embodiments) of the invention will be still more fully understood from the following examples, which are presented herein for illustration only and should not be construed as limiting the invention in any way.

Example 1

A processor-based method for providing posterior assessment of the risk of hypoglycemic of a patient, said method comprises:
providing an algorithm to compute a statistic, $R_{hypo}$ (record), for the risk of hypoglycemia based on the absolute BG levels, BG variability, and insulin delivery that is highly correlated to the posterior (conditional) probability of hypoglycemia, $P(E_{hypo}|record)$, where $E_{hypo}$ denotes the event of hypoglycemia in the next day and record refers to the subject's historical BG, insulin delivery, and activities record; and providing the computed statistic, $R_{hypo}$(record), whereby actionable prior warning of the possibility of hypoglycemia about the patient is so provided to patient or user.

Example 2

The method of example 1, wherein the absolute BG levels and BG variability may be data derived from a CGM device and the absolute insulin delivery may be data obtained from an insulin pump device.

Example 3

The method of example 1, wherein the absolute BG levels and BG variability may be data derived from a CGM device and the absolute insulin delivery may be data obtained from a manual insulin injection device.

Example 4

The method of example 1, wherein the absolute BG levels and BG variability may be data derived from an SMBG device and/or the absolute insulin delivery may be data obtained from an insulin pump device.

Example 5

The method of example 1, wherein the absolute BG levels and BG variability may be data derived from an SMBG device and/or the absolute insulin delivery may be data obtained from a manual insulin injection device.

Example 6

A processor-based method for retroactively providing a safe level of insulin for the patient, said method comprises:
providing an algorithm to retroactively compute a risk-based insulation attenuation factor to the subject's record of insulin delivery; and
providing the computed risk-based insulation attenuation factor and applying the risk-based attenuation factor so that any internal threshold is provided to the patient or user for deciding on reduced temporary basal rates before meals and/or following exercise in the future that may be implemented.

Example 7

The method of example 6, wherein the record of the insulin delivery may be data obtained from an insulin pump device.

Example 8

The method of example 6, wherein the record of the insulin delivery may be data obtained from a manual insulin injection device.

Example 9

The method of example 6, wherein the risk-based attenuation factor would be computed as follows:

$$\phi(R(t, \tau)) = \frac{1}{1 + k_{patient} R(t, \tau)}$$

where $R(t, \tau)$ is a measure of the risk of hypoglycemia between time t and t+τ based on the historical record of BG and insulin data up to time t, based on the BG symmetrization of function and $k_{patient}$ is a patient-specific "aggressiveness" factor.

Example 10

A processor-based method for providing a "net effect" based patient adoptive model, said method comprises:
providing an algorithm to compute:
a dynamic model of the patient's metabolic system, wherein said dynamic model includes descriptive parameters of an individual physiology of the model patient;
a corresponding inferred history of behavioral "net effect" model that explains the glucose variability in the historical record through the dynamic model;
wherein said "net effect" model includes a mathematical representation perturbations of the model patient; and
an update of the patient's physiological parameters based on both (i) the ability of the dynamic model to predict future BG based on known inputs and (ii) the ability of the model to produce net effect curves that are consistent with the patient's record of the perturbations; and
providing said update to the patient or user whereby patient or user can use the update for future course of action.

Example 11

The method of example 10, wherein said descriptive parameters include a representation of the dynamic relationship between oral carbs d (g/min), physical activity e (cal/min), subcutaneous insulin u (U/hr), and the model patient's metabolic state vector $\chi$ whose elements include glucose and insulin concentrations (mg/dl) in various compartments of the body and carbohydrate mass (mg) in the gut.

Example 12

The method of example 11, wherein the glucose concentration (mg/dl) may be data derived from a CGM device and the subcutaneous insulin u and the insulin concentration (mg/dl) may be data obtained from an insulin pump device.

Example 13

The method of example 11, wherein the glucose concentration (mg/dl) may be data derived from a CGM device and the subcutaneous insulin u and the insulin concentration (mg/dl) may be data obtained from a manual insulin injection device.

Example 14

The method of example 11, wherein the glucose concentration (mg/dl) may be data derived from a SMBG device and/or the subcutaneous insulin u and the insulin concentration (mg/dl) may be data obtained from an insulin pump device.

Example 15

The method of example 11, wherein the glucose concentration (mg/dl) may be data derived from a SMBG device and/or the subcutaneous insulin u and the insulin concentration (mg/dl) may be data obtained from a manual insulin injection device.

Example 16

The method of example 11, wherein relationship of said descriptive parameters can be described as a set of discrete-time nonlinear difference equations:

$$\chi(k+1)=F(\chi(k),u(k),d(k),e(k);\theta(k))$$

$$BG_{model}(k)=G(\chi(k),u(k),d(k),e(k);\theta(k))$$

where F and G are nonlinear system equations and $\theta(k)$ is a vector of parameter values that are characteristic of the patient, such as body weight, volumes of distribution in various compartments, various time constant that describe the rates of absorption and clearance between various compartments, some of which are prone to varying as a function of time k.

Example 17

The method of example 11, wherein relationship of said of descriptive parameters can be described as a set of continuous-time nonlinear differential equations:

$$\dot{\chi}(t)=F(\chi(t),u(t),d(t),e(t);\theta(t))$$

$$BG_{model}(t)=G(\chi(t),u(t),d(t),e(t);\theta(t)).$$

Example 18

The method of example 17, wherein nonlinear representation can be linearized around any desired operating point (e.g. steady state glucose concentration) to yield a linear dynamic model:

$$x(k+1)=Ax(k)+B_u u_\delta(k)+B_d d(k)+B_e e(k)$$

$$y(k)=Cx(k)$$

where x is the vector of metabolic state differentials (away from the operating point), $u_\delta$ (U/hr) is the deviation in insulin delivery from the patient's steady state (basal) insulin delivery rate, A, $B_u$, $B_d$, $B_e$ are the state space matrices of the linear model, and y(k) represents BG deviation away from the desired operating point, and the dependence on $\theta(k)$ is embedded within the state space matrices A, $B_u$, $B_d$, $B_e$.

Example 19

The method of example 10, wherein said perturbations include meal profiles, physical activity, and sleep/awake periods.

Example 20

The method of example 10, wherein said "net effect" model provides a "history" of virtual system inputs that reconciles the patient's historical record of BG and historical record of insulin delivery.

Example 21

The method of example 20, wherein the patient's historical record of BG concentration, $\{BG(k)\}_{k \in day}$, and historical record of insulin delivery, $\{u(k)\}_{k \in day}$, the net effect that reconciles the historical information is the vector of virtual carbohydrate inputs $\{d_{n.e.}(k)\}_{k \in day}$ that minimizes the error function:

$$\text{dist}(\{BG(k)\}_{k \in day}, \{BG_{model}(k)_{k \in day}|(u(k)\}_{k \in day}, \{d_{n.e.}(k)\}_{k \in day}),$$

where dist measures the distance between two vectors of BG concentration (in this case actual BG versus model-predicted BG) given the fixed record of insulin delivery $\{u(k)\}_{k \in day}$ and the candidate net effect vector $\{d_{n.e.}(k)\}_{k \in day}$.

Example 22

The method of example 21, wherein the resulting optimal net effect vector (aka. net effect curve), $\{d_{n.e.}(k)\}_{k \in day}$, optimally reconciles the BG and insulin data collected by the patient through a virtual carbohydrate signal, which captures all external influences on the patient as a single external disturbance signal measured in (mg/min).

Example 23

The method of example 22, wherein:
when the net effect curve is positive this shall correspond to the patient actually eating, or it may correspond a period of the day in which the patient is experiencing enhanced insulin sensitivity; and
when the net effect curve is negative then this shall correspond to the patient engaging in intense physical activity or exercise.

Example 24

The method of example 10, wherein:
the patients physiological model parameters, $\{\theta(k)\}_{k \in day}$, includes daily variability due to the patients circadian rhythm; and
the model updater, includes a formula that takes the form having the following:

$$\theta := \theta + U(BG_{res}, NE_{res}; \theta),$$

where U is the recursive parameter update function, which could be gradient-based, $BG_{res}$ is a vector of BG model prediction errors (residuals) and $NE_{res}$ is a vector of errors between the computed net effect curve and the patient's record of actual (verified) behavioral inputs.

Example 25

The method of example 24, wherein the dynamic model is adjusted on multiple time scales, whereby parameter updates can be computed daily based on BG residuals:

$$\theta := \theta + U_1(BG_{res}; \theta),$$

and updates based on net effect mismatch can be computed on a longer time scale, such as every week or month:

$$\theta := \theta + U_2(NE_{res}; \theta).$$

Example 26

The method of example 10, further comprising providing a retroactive assessment of the patient's optimal rate of insulin delivery, wherein said algorithm:
retroactively computes what the patient's optimal rate of insulin delivery would have been over a predetermined period of historical time given that the disturbances to the system are exactly the historical of net effect curves computed for the patient over that interval of time, wherein for each "history" of net effect curves there is a corresponding "history" of insulin delivery rates that account for meals, exercise, and corrections for each day in the considered interval of time;
maps between the net effect curve for a given day and the model-based response of an optimal controller, wherein these vectors of optimal responses are collected and analyzed, and presented to the patient or user for a day-by-day review of insulin treatment;
extracts features from the optimal responses that correspond to important but random events by subtracting discrete amounts of insulin associated with meals or accounting for discrete insulin deficits associated with temporary basal rates around exercise, whereby the remaining schedule of insulin delivery corresponds to a representation of the patient's "optimal" basal pattern each day in the historical record; and
identifies consistency in the retroactively computed optimal basal rates, such optimal basal rates in a plurality of duration segments representing the patient's treatment duration; and
said method further comprising:
providing to the patient or user the median level of basal insulin that would have been applied in each segment, wherein the patient or user could use this information to (i) decide upon on reduced temporary basal rates before meals and/or following exercise in the future or (ii) adjust the patient's long-term basal rate profile.

Example 27

The method of example 10, further comprising providing an on-demand adaptive correction of insulin advice model, said method comprises:
providing an algorithm to include the following computations:
retrospective detecting for meal and exercise activities;
stochastic modeling to provide a description about the timing and content of meals and exercise; and
providing insulin correction advice to a patient or user that would be in response to a patient and user request.

Example 28

The method of example 27, wherein:
said retrospective detection for meal and exercise activities includes the algorithm for reconciling current history of said patient "net effect curves" with the historical record of patient-acknowledged meals and exercise events to produce a validated (high-confidence) record of relevant patient behaviors, wherein the reconciling includes identifying discrepancies between (i) the net effect curves computed from the available BG and insulin data for the patient and (ii) the meal and exercise events that are acknowledged by the patient or user through the systems user interface; and
said method comprises:
providing suggestions from said discrepancies, wherein suggestions are communicated to patient or user; and
receiving any responses resultant from user or patient to form the final, validated record of relevant patient activities.

Example 29

The method of example 28, wherein:
said stochastic modeling includes the algorithm for receiving said final, validated record of relevant patient activities and stochastically modeling to represent the timing and content of meals and exercise of the patient's behavior.

Example 30

The method of example 29, wherein:
said insulin correction includes the algorithm for monitoring the patient's status and to provide insulin correction advice in the moment the patient or user asks for it, based on (i) the stochastic modeling for upcoming behavioral disturbances and (ii) the current dynamic model of the patient's metabolic system that allows for the prediction of the impact of various alternative correction insulin amounts.

Example 31

A system for providing posterior assessment of the risk of hypoglycemic of a patient, said system comprises:
a retroactive risk-based safety module having a processor to compute a statistic, $R_{hypo}(record)$, for the risk of hypoglycemia based on the absolute BG levels, BG variability, and insulin delivery that is highly correlated to the posterior (conditional) probability of hypoglycemia, $P(E_{hypo}|record)$, where $E_{hypo}$ denotes the event of hypoglycemia in the next day and record refers to the subject's historical BG, insulin delivery, and activities record; and
said processor outputs the computed statistic, $R_{hypo}(record)$, whereby actionable prior warning of the possibility of hypoglycemia about the patient is so provided to patient or user.

Example 32

The system of example 31, wherein the absolute BG levels and BG variability may be data derived from a CGM device and the absolute insulin delivery may be data obtained from an insulin pump device.

Example 33

The system of example 31, wherein the absolute BG levels and BG variability may be data derived from a CGM device and the absolute insulin delivery may be data obtained from a manual insulin injection device.

Example 34

The system of example 31, wherein the absolute BG levels and BG variability may be data derived from an SMBG device and the absolute insulin delivery may be data obtained from an insulin pump device.

Example 35

The system of example 31, wherein the absolute BG levels and BG variability may be data derived from an SMBG device and the absolute insulin delivery may be data obtained from a manual insulin injection device.

Example 36

The system of example 31, further comprising:
a CGM device, wherein the absolute BG levels and BG variability may be data derived from said CGM device; and
an insulin pump device, wherein the absolute insulin delivery may be data obtained from said insulin pump device.

Example 37

The system of example 31, further comprising:
a CGM device, wherein the absolute BG levels and BG variability may be data derived from said CGM device; and
a manual insulin injection device, wherein the absolute insulin delivery may be data obtained from said manual insulin injection device.

Example 38

The system of example 31, further comprising:
an SMBG device, wherein the absolute BG levels and BG variability may be data derived from said SMBG device; and/or
an insulin pump device, wherein the absolute insulin delivery may be data obtained from said insulin pump device.

Example 39

The system of example 31, further comprising:
an SMBG device, wherein the absolute BG levels and BG variability may be data derived from said SMBG device; and/or
a manual insulin injection device, wherein the absolute insulin delivery may be data obtained from said manual insulin injection device.

Example 40 system for retroactively providing a safe level of insulin for the patient, said system comprises:
a retroactive risk-based safety module having a processor to retroactively compute a risk-based insulation attenuation factor to the subject's record of insulin delivery; and
said processor outputs the computed risk-based insulation attenuation factor and applying the risk-based attenuation factor so that any internal threshold is provided to the patient or user for deciding on reduced temporary basal rates before meals and/or following exercise in the future that may be implemented.

Example 41

The system of example 40, wherein the insulin delivery may be data obtained from an insulin pump device.

Example 42

The system of example 40, wherein the insulin delivery may be data obtained from a manual insulin injection device.

Example 43

The system of example 40, further comprising:
an insulin pump device, wherein the insulin delivery may be data obtained from said insulin pump device.

Example 44

The system of example 40, further comprising:
a manual insulin injection device, wherein the insulin delivery may be data obtained from said manual insulin injection device.

Example 45

The system of example 40, wherein the risk-based attenuation factor would be computed as follows:

$$\phi(R(t,\tau)) = \frac{1}{1 + k_{patient}R(t,\tau)}$$

where $R(t, \tau)$ is a measure of the risk of hypoglycemia between time t and t+τ based on the historical record of BG and insulin data up to time t, based on the BG symmetrization of function and $k_{patient}$ is a patient-specific "aggressiveness" factor.

Example 46

A system for providing a "net effect" based patient adoptive model, said system comprises:
a net effect estimator module having a processor to compute:
  a dynamic model of the patient's metabolic system,
  wherein said dynamic model includes descriptive parameters of an individual physiology of the model patient; and
  a corresponding inferred history of behavioral "net effect" model that explains the glucose variability in the historical record through the dynamic model;
wherein said "net effect" model includes a mathematical representation perturbations of the model patient; and
a model updater module having a processor to compute:
  an update of the patient's physiological parameters based on both (i) the ability of the dynamic model to predict future BG based on known inputs and (ii) the ability of the model to produce net effect curves that are consistent with the patient's record of the perturbations; and
said system outputs said update to the patient or user whereby patient or user can use the update for future course of action.

Example 47

The system of example 46, wherein said descriptive parameters include a representation of the dynamic relationship between oral carbs d (g/min), physical activity e (cal/min), subcutaneous insulin u (U/hr), and the model patient's metabolic state vector X whose elements include glucose and insulin concentrations (mg/dl) in various compartments of the body and carbohydrate mass (mg) in the gut.

Example 48

The system of example 47, wherein the glucose concentration (mg/dl) may be data derived from a CGM device and the subcutaneous insulin u and the insulin concentration (mg/dl) may be data obtained from an insulin pump device.

Example 49

The system of example 47, wherein the glucose concentration (mg/dl) may be data derived from a CGM device and the subcutaneous insulin u and the insulin concentration (mg/dl) may be data obtained from a manual insulin injection device.

Example 50

The system of example 47, wherein the glucose concentration (mg/dl) may be data derived from a SMBG device and the subcutaneous insulin u and the insulin concentration (mg/dl) may be data obtained from an insulin pump device.

Example 51

The system of example 47, wherein the glucose concentration (mg/dl) may be data derived from a SMBG device and the subcutaneous insulin u and the insulin concentration (mg/dl) may be data obtained from a manual insulin injection.

Example 52

The system of example 47, further comprising:
an CGM device, wherein the glucose concentration (mg/dl) may be data derived from said CGM device; and
an insulin pump, wherein the subcutaneous insulin u and the insulin concentration (mg/dl) may be data obtained from an insulin pump device.

Example 53

The system of example 47, further comprising:
an SMBG device, wherein the glucose concentration (mg/dl) may be data derived from said SMBG device; and
an insulin pump device or an insulin injection device, wherein the subcutaneous insulin u and the insulin concentration (mg/dl) may be data obtained from said insulin pump device or said insulin injection device.

Example 54

The system of example 47, wherein relationship said descriptive parameters can be described as a set of discrete-time nonlinear difference equations:

$$\chi(k+1) = F(\chi(k), u(k), d(k), e(k); \theta(k))$$

$$BG_{model}(k) = G(\chi(k), u(k), d(k), e(k); \theta(k))$$

where F and G are nonlinear system equations and $\theta(k)$ is a vector of parameter values that are characteristic of the patient, such as body weight, volumes of distribution in various compartments, various time constant that describe the rates of absorption and clearance between various compartments, some of which are prone to varying as a function of time k.

Example 55

The system of example 47, wherein relationship of said of descriptive parameters can be described as a set of continuous-time nonlinear differential equations:

$$\dot{\chi}(t) = F(\chi(t), u(t), d(t), e(t); \theta(t))$$

$$BG_{model}(t) = G(\chi(t), u(t), d(t), e(t); \theta(t)).$$

Example 56

The system of example 55, wherein nonlinear representation can be linearized around any desired operating point (e.g. steady state glucose concentration) to yield a linear dynamic model:

$$x(k+1) = Ax(k) + B_u u_\delta(k) + B_d d(k) + B_e e(k)$$

$$y(k) = Cx(k)$$

where x is the vector of metabolic state differentials (away from the operating point), $u_\delta$ (U/hr) is the deviation in insulin delivery from the patient's steady state (basal) insulin delivery rate, A, $B_u$, $B_d$, $B_e$ are the state space matrices of the linear model, and y(k) represents BG deviation away from the desired operating point, and the dependence on θ(k) is embedded within the state space matrices A, $B_u$, $B_d$, $B_e$.

Example 57

The system of example 46, wherein said perturbations include meal profiles, physical activity, and sleep/awake periods.

Example 58

The system of example 46, wherein said "net effect" model provides a "history" of virtual system inputs that reconciles the patient's historical record of BG and historical record of insulin delivery.

Example 59

The system of example 58, wherein the patient's historical record of BG concentration, $\{BG(k)\}_{k \in day}$, and historical record of insulin delivery, $\{u(k)\}_{k \in day}$, the net effect that reconciles the historical information is the vector of virtual carbohydrate inputs $\{d_{n.e.}(k)\}_{k \in day}$ that minimizes the error function:

$$\text{dist}(\{BG(k)\}_{k \in day}, \{BG_{model}(k)\}_{k \in day} | \{u(k)\}_{k \in day}, \{d_{n.e.}(k)\}_{k \in day}),$$

where dist measures the distance between two vectors of BG concentration (in this case actual BG versus model-predicted BG) given the fixed record of insulin delivery $\{u(k)\}_{k \in day}$ and the candidate net effect vector $\{d_{n.e.}(k)\}_{k \in day}$.

Example 60

The system of example 59, wherein the resulting optimal net effect vector (aka. net effect curve), $\{d_{n.e.}(k)\}_{k \in day}$, optimally reconciles the BG and insulin data collected by the patient through a virtual carbohydrate signal, which captures all external influences on the patient as a single external disturbance signal measured in (mg/min).

Example 61

The system of example 60, wherein:
when the net effect curve is positive this shall correspond to the patient actually eating, or it may correspond a period of the day in which the patient is experiencing enhanced insulin sensitivity; and
when the net effect curve is negative then this shall correspond to the patient engaging in intense physical activity or exercise.

Example 62

The system of example 46, wherein:
the patients physiological model parameters, $\{\theta(k)\}_{k \in day}$, includes daily variability due to the patients circadian rhythm; and
the processor of the model updater module is configured to compute the following:

$$\theta := \theta + U(BG_{res}, NE_{res}; \theta),$$

where U is the recursive parameter update function, which could be gradient-based, $BG_{res}$ is a vector of BG model prediction errors (residuals) and $NE_{res}$ is a vector of errors between the computed net effect curve and the patient's record of actual (verified) behavioral inputs.

Example 63

The system of example 62, wherein the dynamic model is adjusted on multiple time scales, whereby parameter updates can be computed daily based on BG residuals:

$$\theta := \theta + U_1(BG_{res}; \theta),$$

and updates based on net effect mismatch can be computed on a longer time scale, such as every week or month:

$$\theta := \theta + U_2(NE_{res}; \theta).$$

Example 64

The system of example 46, further configured to provide a retroactive assessment of the patient's optimal rate of insulin delivery, wherein said system comprises:
a retrospective optimal control analyzer module having a processor configured to:
retroactively compute what the patient's optimal rate of insulin delivery would have been over a predetermined period of historical time given that the disturbances to the system are exactly the historical of net effect curves computed for the patient over that interval of time, wherein for each "history" of net effect curves there is a corresponding "history" of insulin delivery rates that account for meals, exercise, and corrections for each day in the considered interval of time; and
map between the net effect curve for a given day and the model-based response of an optimal controller, wherein these vectors of optimal responses are collected and analyzed, and presented to the patient or user for a day-by-day review of insulin treatment;
a retro-optimal basal rate extractor module having a processor configured to:
extract features from the optimal responses that correspond to important but random events by subtracting discrete amounts of insulin associated with meals or accounting for discrete insulin deficits associated with temporary basal rates around exercise, whereby the remaining schedule of insulin delivery corresponds to a representation of the patient's "optimal" basal pattern each day in the historical record; and
identify consistency in the retroactively computed optimal basal rates, such optimal basal rates in a plurality of duration segments representing the patient's treatment duration; and
said system being configured to:
provide an output to the patient or user the median level of basal insulin that would have been applied in each segment, wherein the patient or user could use this information to (i) decide upon on reduced temporary basal rates before meals and/or following exercise in the future or (ii) adjust the patient's long-term basal rate profile.

Example 65

The system of example 46, further configured to provide an on-demand adaptive correction of insulin advice model, said system comprises:
a retrospective meal and exercise detector module having a processor to provide retrospective detecting for meal and exercise activities;

a meal and exercise stochastic modeler module having a processor to provide stochastic modeling to provide a description about the timing and content of meals and exercise; and a correction bolus advisor module having a processor to provide and output insulin correction advice to a patient or user that would be in response to a patient and user request.

Example 66

The system of example 65, wherein:
said retrospective detection for meal and exercise activities includes the algorithm for reconciling current history of said patient "net effect curves" with the historical record of patient-acknowledged meals and exercise events to produce a validated (high-confidence) record of relevant patient behaviors, wherein the reconciling includes identifying discrepancies between (i) the net effect curves computed from the available BG and insulin data for the patient and (ii) the meal and exercise events that are acknowledged by the patient or user through the systems user interface; and
said system configured to comprise:
an output module to provide suggestions from said discrepancies, wherein suggestions are communicated to patient or user; and
an input module to receive any responses resultant from user or patient to form the final, validated record of relevant patient activities.

Example 67

The system of example 66, wherein:
said processor of said stochastic modeling module being configured for receiving said final, validated record of relevant patient activities and stochastically modeling to represent the timing and content of meals and exercise of the patient's behavior.

Example 68

The system of example 67, wherein:
said processor of said correction bolus advisor module being configured for monitoring the patient's status and to provide insulin correction advice output in the moment the patient or user asks for it, based on (i) the stochastic modeling for upcoming behavioral disturbances and (ii) the current dynamic model of the patient's metabolic system that allows for the prediction of the impact of various alternative correction insulin amounts.

Example 69

A non-transitory computer readable medium containing program instructions for providing posterior assessment of the risk of hypoglycemic of a patient, wherein execution of the program instructions by one or more processors of a computer system causes the processor to carry out the following steps of:
providing an algorithm to compute a statistic, $R_{hypo}$(record), for the risk of hypoglycemia based on the absolute BG levels, BG variability, and insulin delivery that is highly correlated to the posterior (conditional) probability of hypoglycemia, $P(E_{hypo}|record)$, where $E_{hypo}$ denotes the event of hypoglycemia in the next day and record refers to the subject's historical BG, insulin delivery, and activities record; and providing the computed statistic, $R_{hypo}$(record), whereby actionable prior warning of the possibility of hypoglycemia about the patient is so provided to patient or user.

Example 70

The non-transitory computer readable medium of example 69, wherein the absolute BG levels and BG variability may be data derived from a CGM device and the absolute insulin delivery may be data obtained from an insulin pump device.

Example 71

The non-transitory computer readable medium of example 69, wherein the absolute BG levels and BG variability may be data derived from a CGM device and the absolute insulin delivery may be data obtained from a manual insulin injection device.

Example 72

The non-transitory computer readable medium of example 69, wherein the absolute BG levels and BG variability may be data derived from an SMBG device and/or the absolute insulin delivery may be data obtained from an insulin pump device.

Example 73

The non-transitory computer readable medium of example 69, wherein the absolute BG levels and BG variability may be data derived from an SMBG device and/or the absolute insulin delivery may be data obtained from a manual insulin injection device.

Example 74

A non-transitory computer readable medium containing program instructions for retroactively providing a safe level of insulin for the patient, wherein execution of the program instructions by one or more processors of a computer system causes the processor to carry out the following steps of:
providing an algorithm to retroactively compute a risk-based insulation attenuation factor to the subject's record of insulin delivery; and
providing the computed risk-based insulation attenuation factor and applying the risk-based attenuation factor so that any internal threshold is provided to the patient or user for deciding on reduced temporary basal rates before meals and/or following exercise in the future that may be implemented.

Example 75

The non-transitory computer readable medium of example 74, wherein the record of the insulin delivery may be data obtained from an insulin pump device.

Example 76

The non-transitory computer readable medium of example 74, wherein the record of the insulin delivery may be data obtained from a manual insulin injection device.

Example 77

The non-transitory computer readable medium of example 202, wherein the risk-based attenuation factor would be computed as follows:

$$\phi(R(t,\tau)) = \frac{1}{1+k_{patient}R(t,\tau)}$$

where R(t, τ) is a measure of the risk of hypoglycemia between time t and t+τ based on the historical record of BG and insulin data up to time t, based on the BG symmetrization of function and $k_{patient}$ is a patient-specific "aggressiveness" factor.

Example 78

A non-transitory computer readable medium containing program instructions for providing a "net effect" based patient adoptive model, wherein execution of the program instructions by one or more processors of a computer system causes the processor to carry out the following steps of:
computing a dynamic model of the patient's metabolic system,
wherein said dynamic model includes descriptive parameters of an individual physiology of the model patient;
computing a corresponding inferred history of behavioral "net effect" model that explains the glucose variability in the historical record through the dynamic model;
wherein said "net effect" model includes a mathematical representation perturbations of the model patient;
computing an update of the patient's physiological parameters based on both (i) the ability of the dynamic model to predict future BG based on known inputs and (ii) the ability of the model to produce net effect curves that are consistent with the patient's record of the perturbations; and
providing said update to the patient or user whereby patient or user can use the update for future course of action.

Example 79

The non-transitory computer readable medium of example 78, wherein said descriptive parameters include a representation of the dynamic relationship between oral carbs d (g/min), physical activity e (cal/min), subcutaneous insulin u (U/hr), and the model patient's metabolic state vector X whose elements include glucose and insulin concentrations (mg/dl) in various compartments of the body and carbohydrate mass (mg) in the gut.

Example 80

The non-transitory computer readable medium of example 79, wherein the glucose concentration (mg/dl) may be data derived from a CGM device and the subcutaneous insulin u and the insulin concentration (mg/dl) may be data obtained from an insulin pump device.

Example 81

The non-transitory computer readable medium of example 79, wherein the glucose concentration (mg/dl) may be data derived from a CGM device and the subcutaneous insulin u and the insulin concentration (mg/dl) may be data obtained from a manual insulin injection device.

Example 82

The non-transitory computer readable medium of example 79, wherein the glucose concentration (mg/dl) may be data derived from a SMBG device and/or the subcutaneous insulin u and the insulin concentration (mg/dl) may be data obtained from an insulin pump device.

Example 83

The non-transitory computer readable medium of example 79, wherein the glucose concentration (mg/dl) may be data derived from a SMBG device and/or the subcutaneous insulin u and the insulin concentration (mg/dl) may be data obtained from a manual insulin injection device.

Example 84

The non-transitory computer readable medium of example 79, wherein relationship said descriptive parameters can be described as a set of discrete-time nonlinear difference equations:

$$\chi(k+1)=F(\chi(k),u(k),d(k),e(k);\theta(k))$$

$$BG_{model}(k)=G(\chi(k),u(k),d(k),e(k);\theta(k))$$

where F and G are nonlinear system equations and θ(k) is a vector of parameter values that are characteristic of the patient, such as body weight, volumes of distribution in various compartments, various time constant that describe the rates of absorption and clearance between various compartments, some of which are prone to varying as a function of time k.

Example 85

The non-transitory computer readable medium of example 79, wherein relationship of said of descriptive parameters can be described as a set of continuous-time nonlinear differential equations:

$$\dot{\chi}(t)=F(\chi(t),u(t),d(t),e(t);\theta(t))$$

$$BG_{model}(t)=G(\chi(t),u(t),d(t),e(t);\theta(t)).$$

Example 86

The non-transitory computer readable medium of example 185, wherein nonlinear representation can be linearized around any desired operating point (e.g. steady state glucose concentration) to yield a linear dynamic model:

$$x(k+1)=Ax(k)+B_u u_\delta(k)+B_d d(k)+B_e e(k)$$

$$y(k)=Cx(k)$$

where x is the vector of metabolic state differentials (away from the operating point), $u_\delta$ (U/hr) is the deviation in insulin delivery from the patient's steady state (basal) insulin delivery rate, A, $B_u$, $B_d$, $B_e$ are the state space matrices of the linear model, and y(k) represents BG deviation away from the desired operating point, and the dependence on θ(k) is embedded within the state space matrices A, $B_u$, $B_d$, $B_e$.

Example 87

The non-transitory computer readable medium of example 78, wherein said perturbations include meal profiles, physical activity, and sleep/awake periods.

Example 88

The non-transitory computer readable medium of example 78, wherein said "net effect" model provides a "history" of virtual system inputs that reconciles the patient's historical record of BG and historical record of insulin delivery.

Example 89

The non-transitory computer readable medium of example 88, wherein the patient's historical record of BG concentration, $\{BG(k)\}_{k \in day}$, and historical record of insulin delivery, $\{u(k)\}_{k \in day}$, the net effect that reconciles the historical information is the vector of virtual carbohydrate inputs $\{d_{n.e.}(k)\}_{k \in day}$ that minimizes the error function:

$$\text{dist}(\{BG(k)\}_{k \in day}, \{BG_{model}(k)\}_{k \in day} | \{u(k)\}_{k \in day}, \{d_{n.e.}(k)\}_{k \in day}),$$

where dist measures the distance between two vectors of BG concentration (in this case actual BG versus model-predicted BG) given the fixed record of insulin delivery $\{u(k)\}_{k \in day}$ and the candidate net effect vector $\{(d_{n.e.}(k)\}_{k \in day}$.

Example 90

The non-transitory computer readable medium of example 89, wherein the resulting optimal net effect vector (aka. net effect curve), $\{d_{n.e.}(k)\}_{k \in day}$, optimally reconciles the BG and insulin data collected by the patient through a virtual carbohydrate signal, which captures all external influences on the patient as a single external disturbance signal measured in (mg/min).

Example 91

The non-transitory computer readable medium of example 90, wherein:
when the net effect curve is positive this shall correspond to the patient actually eating, or it may correspond a period of the day in which the patient is experiencing enhanced insulin sensitivity; and
when the net effect curve is negative then this shall correspond to the patient engaging in intense physical activity or exercise.

Example 92

The non-transitory computer readable medium of example 78, wherein:
the patients physiological model parameters, $\{\theta(k)\}_{k \in day}$, includes daily variability due to the patients circadian rhythm; and
the model updater, includes a formula that takes the form having the following:

$$\theta := \theta + U(BG_{res}, NE_{res}; \theta),$$

where U is the recursive parameter update function, which could be gradient-based, $BG_{res}$ is a vector of BG model prediction errors (residuals) and $NE_{res}$ is a vector of errors between the computed net effect curve and the patient's record of actual (verified) behavioral inputs.

Example 93

The non-transitory computer readable medium of example 92, wherein the dynamic model is adjusted on multiple time scales, whereby parameter updates can be computed daily based on BG residuals:

$$\theta := \theta + U_1(BG_{res}; \theta),$$

and updates based on net effect mismatch can be computed on a longer time scale, such as every week or month:

$$\theta := \theta + U_2(NE_{res}; \theta).$$

Example 94

The non-transitory computer readable medium of example 78, further comprising providing a retroactive assessment of the patient's optimal rate of insulin delivery, wherein execution of the program instructions by one or more processors of a computer system causes the processor to carry out the following steps of:
retroactively computing what the patient's optimal rate of insulin delivery would have been over a predetermined period of historical time given that the disturbances to the system are exactly the historical of net effect curves computed for the patient over that interval of time, wherein for each "history" of net effect curves there is a corresponding "history" of insulin delivery rates that account for meals, exercise, and corrections for each day in the considered interval of time;
mapping between the net effect curve for a given day and the model-based response of an optimal controller, wherein these vectors of optimal responses are collected and analyzed, and presented to the patient or user for a day-by-day review of insulin treatment;
extracting features from the optimal responses that correspond to important but random events by subtracting discrete amounts of insulin associated with meals or accounting for discrete insulin deficits associated with temporary basal rates around exercise, whereby the remaining schedule of insulin delivery corresponds to a representation of the patient's "optimal" basal pattern each day in the historical record;
identifying consistency in the retroactively computed optimal basal rates, such optimal basal rates in a plurality of duration segments representing the patient's treatment duration; and
providing to the patient or user the median level of basal insulin that would have been applied in each segment, wherein the patient or user could use this information to (i) decide upon on reduced temporary basal rates before meals and/or following exercise in the future or (ii) adjust the patient's long-term basal rate profile.

Example 95

The non-transitory computer readable medium of example 78, further comprising providing an on-demand adaptive correction of insulin advice model, wherein execution of the program instructions by one or more processors of a computer system causes the processor to carry out the following steps of:
retrospectively detecting for meal and exercise activities;
stochastic modeling to provide a description about the timing and content of meals and exercise; and
providing insulin correction advice to a patient or user that would be in response to a patient and user request.

Example 96

The non-transitory computer readable medium of example 95, wherein:
said retrospective detection for meal and exercise activities includes the algorithm for reconciling current history of said patient "net effect curves" with the historical record of patient-acknowledged meals and exercise events to produce a validated (high-confidence) record of relevant patient behaviors, wherein the reconciling includes identifying discrepancies between (i) the net effect curves computed from the available BG and insulin data for the patient and (ii) the meal and exercise events that are acknowledged by the patient or user through the systems user interface; and wherein execution of the program instructions by one or more processors of a computer system causes the processor to carry out the following steps of:

providing suggestions from said discrepancies, wherein suggestions are communicated to patient or user; and receiving any responses resultant from user or patient to form the final, validated record of relevant patient activities.

Example 97

The non-transitory computer readable medium of example 96, wherein:

said stochastic modeling includes the algorithm for receiving said final, validated record of relevant patient activities and stochastically modeling to represent the timing and content of meals and exercise of the patient's behavior.

Example 98

The non-transitory computer readable medium of example 97, wherein:

said insulin correction includes the algorithm for monitoring the patient's status and to provide insulin correction advice in the moment the patient or user asks for it, based on (i) the stochastic modeling for upcoming behavioral disturbances and (ii) the current dynamic model of the patient's metabolic system that allows for the prediction of the impact of various alternative correction insulin amounts.

It should be appreciated that any one or more of the example nos. 1-98 may be combined with any one or more of example nos. 1-98 as desired or required.

It should be appreciated that as discussed herein, a subject or patient may be a human or any animal. It should be appreciated that an animal may be a variety of any applicable type, including, but not limited thereto, mammal, veterinarian animal, livestock animal or pet type animal, etc. As an example, the animal may be a laboratory animal specifically selected to have certain characteristics similar to human (e.g. rat, dog, pig, monkey), etc. It should be appreciated that the subject may be any applicable human patient, for example.

Unless clearly specified to the contrary, there is no requirement for any particular described or illustrated activity or element, any particular sequence or such activities, any particular size, speed, material, duration, contour, dimension or frequency, or any particularly interrelationship of such elements. Moreover, any activity can be repeated, any activity can be performed by multiple entities, and/or any element can be duplicated. Further, any activity or element can be excluded, the sequence of activities can vary, and/or the interrelationship of elements can vary. It should be appreciated that aspects of the present invention may have a variety of sizes, contours, shapes, compositions and materials as desired or required.

In summary, while the present invention has been described with respect to specific embodiments, many modifications, variations, alterations, substitutions, and equivalents will be apparent to those skilled in the art. The present invention is not to be limited in scope by the specific embodiment described herein. Indeed, various modifications of the present invention, in addition to those described herein, will be apparent to those of skill in the art from the foregoing description and accompanying drawings. Accordingly, the invention is to be considered as limited only by the spirit and scope of the following claims, including all modifications and equivalents.

Still other embodiments will become readily apparent to those skilled in this art from reading the above-recited detailed description and drawings of certain exemplary embodiments. It should be understood that numerous variations, modifications, and additional embodiments are possible, and accordingly, all such variations, modifications, and embodiments are to be regarded as being within the spirit and scope of this application. For example, regardless of the content of any portion (e.g., title, field, background, summary, abstract, drawing figure, etc.) of this application, unless clearly specified to the contrary, there is no requirement for the inclusion in any claim herein or of any application claiming priority hereto of any particular described or illustrated activity or element, any particular sequence of such activities, or any particular interrelationship of such elements. Moreover, any activity can be repeated, any activity can be performed by multiple entities, and/or any element can be duplicated. Further, any activity or element can be excluded, the sequence of activities can vary, and/or the interrelationship of elements can vary. Unless clearly specified to the contrary, there is no requirement for any particular described or illustrated activity or element, any particular sequence or such activities, any particular size, speed, material, dimension or frequency, or any particularly interrelationship of such elements. Accordingly, the descriptions and drawings are to be regarded as illustrative in nature, and not as restrictive. Moreover, when any number or range is described herein, unless clearly stated otherwise, that number or range is approximate. When any range is described herein, unless clearly stated otherwise, that range includes all values therein and all sub ranges therein. Any information in any material (e.g., a United States/foreign patent, United States/foreign patent application, book, article, etc.) that has been incorporated by reference herein, is only incorporated by reference to the extent that no conflict exists between such information and the other statements and drawings set forth herein. In the event of such conflict, including a conflict that would render invalid any claim herein or seeking priority hereto, then any such conflicting information in such incorporated by reference material is specifically not incorporated by reference herein.

We claim:

1. A processor-based method for treating a patient with insulin, the patient suffering from type 1 diabetes mellitus (T1DM), by providing a posterior assessment of a risk of hypoglycemia in the patient, the method comprising:

receiving, via a processor, historical data including a patient's absolute blood glucose (BG) levels, BG variability, insulin delivery, and activities;

determining, via said processor or another processor and via kernel density estimates of BG time series from the historical data, a parameter, $R_{hypo}$(record), that is representative of the risk of hypoglycemia associated with the posterior probability of hypoglycemia, $P(E_{hypo}|\text{record})$, where $E_{hypo}$ denotes the event of hypoglycemia in the next day and record refers to a record of the patient's historical BG levels, insulin delivery, and activities record;

comparing, via said processor or said another processor, the historical insulin delivery data with the $R_{hypo}$(record) associated with the $P(E_{hypo}|record)$;

receiving, via said processor or said another processor, real-time BG and real-time insulin delivery data and adjusting a basal rate profile for the patient based on the comparison so as to ameliorate risk of entering hypoglycemia; and calculating, via said processor or said another processor, a correction bolus based on the adjusted basal rate profile and delivering insulin in accordance with the correction bolus calculation.

2. The method of claim 1, wherein the absolute BG levels and the BG variability are data derived from a continuous glucose monitoring (CGM) device and the insulin delivery is data obtained from an insulin pump device.

3. The method of claim 1, wherein the absolute BG levels and the BG variability are data derived from a continuous glucose monitoring (CGM) device and the insulin delivery is data obtained from a manual insulin injection device.

4. The method of claim 1, wherein the absolute BG levels and the BG variability are data derived from a self-monitoring blood glucose (SMBG) device and the insulin delivery is data obtained from an insulin pump device.

5. The method of claim 1, wherein the absolute BG levels and the BG variability are data derived from a self-monitoring blood glucose (SMBG) device and the insulin delivery are data obtained from a manual insulin injection device.

6. The method of claim 1, wherein the output device is configured to store the $R_{hypo}$(record) in a memory.

7. A processor-based method for treating a patient by using retroactive analysis to provide a safe level of insulin dosage for the patient, the patient suffering from type 1 diabetes mellitus (T1DM), the method comprising:

receiving, via a processor, a historical record of blood glucose (BG) levels and insulin delivery for a patient;

determining, via said processor or another processor, a risk of hypoglycemia for patient activities using a symmetrization function;

determining, via said processor or said another processor, an attenuation factor that acts as a threshold when delivering insulin;

receiving, via said processor or said another processor, real-time BG and activity data and adjusting a basal rate profile for the patient to incorporate the attenuation factor so as to ameliorate risk of entering hypoglycemia, wherein adjusting the basal rate profile involves reducing temporary basal rates before meals and/or following exercise; and calculating, via said processor or said another processor, a correction bolus based on the adjusted basal rate profile and delivering insulin in accordance with the correction bolus calculation.

8. The method of claim 7, wherein the record of the insulin delivery are data obtained from an insulin pump device.

9. The method of claim 7, wherein the record of the insulin delivery are data obtained from a manual insulin injection device.

10. The method of claim 7, wherein the attenuation factor is computed as follows:

$$\phi(R(t,\tau)) = \frac{1}{1 + k_{patient} R(t,\tau)}$$

where $R(t, \tau)$ is a measure of the risk of hypoglycemia between time t and t+τ based on the historical record of BG and insulin data up to time t, based on the BG symmetrization of function and kpatient is a patient-specific aggressiveness factor.

11. A processor-based method for treating a patient with insulin, the patient suffering from type 1 diabetes mellitus (T1DM), by providing a net effect based patient adaptive model, the method comprising:

delivering insulin based on a patient's metabolic system;
computing, by a processor:
a dynamic model of the patient's metabolic system, wherein said dynamic model includes descriptive parameters of an individual physiology of the model patient;
a corresponding inferred history of a behavioral net effect model that explains the glucose variability in the historical record through the dynamic model, wherein said net effect model includes a mathematical representation of perturbations of the model patient; and
an update of the patient's physiological parameters based on both (i) the ability of the dynamic model to predict future blood glucose (BG) based on known inputs and (ii) the ability of the model to produce net effect curves that are consistent with the patient's record of the perturbations; and estimating, via said processor or another processor, the patient's current metabolic system using the updated physiological parameters;

adjusting, via said processor or said another processor, a basal rate profile for the patient in accordance with said patient's estimated current metabolic system; and calculating, via said processor or said another processor, a correction bolus based on the adjusted basal rate profile and delivering insulin in accordance with the correction bolus calculation.

12. The method of claim 11, wherein said descriptive parameters include a representation of the dynamic relationship between oral carbs d (g/min), physical activity e (cal/min), subcutaneous insulin u (U/hr), and the model patient's metabolic state vector χ whose elements include glucose and insulin concentrations (mg/dl) in various compartments of the body and carbohydrate mass (mg) in the gut.

13. The method of claim 12, wherein the glucose concentration (mg/dl) are data derived from a continuous glucose monitoring (CGM) device and the subcutaneous insulin u and the insulin concentration (mg/dl) are data obtained from an insulin pump device.

14. The method of claim 12, wherein the glucose concentration (mg/dl) are data derived from a continuous glucose monitoring (CGM) device and the subcutaneous insulin u and the insulin concentration (mg/dl) are data obtained from a manual insulin injection device.

15. The method of claim 12, wherein the glucose concentration (mg/dl) are data derived from a self-monitoring blood glucose (SMBG) device and/or the subcutaneous insulin u and the insulin concentration (mg/dl) are data obtained from an insulin pump device.

16. The method of claim 12, wherein the glucose concentration (mg/dl) are data derived from a self-monitoring blood glucose (SMBG) device and/or the subcutaneous insulin u and the insulin concentration (mg/dl) are data obtained from a manual insulin injection device.

17. The method of claim 12, wherein relationship of said descriptive parameters is described as a set of discrete-time nonlinear difference equations:

$$x(k+1)=F(x(k),u(k),d(k),e(k);\theta(k))$$

$$BG_{model}(k)=G(X(k),u(k),d(k),e(k);\theta(k))$$

where F and G are nonlinear system equations and $\theta(k)$ is a vector of parameter values that are characteristic of the patient, such as body weight, volumes of distribution in various compartments, various time constant that describe the rates of absorption and clearance between various compartments, at least some of which are prone to varying as a function of time k.

18. The method of claim 12, wherein relationship of said of descriptive parameters is described as a set of continuous-time nonlinear differential equations:

$$\dot{x}(t)=F(x(t),u(t),d(t),e(t);\theta(t))$$

$$BG_{model}(t)=G(x(t),u(t),d(t),e(t);\theta(t)).$$

19. The method of claim 18, wherein nonlinear representation is linearized around an operating point to yield a linear dynamic model:

$$x(k+1)=Ax(k)+B_u u_s(k)+B_d d(k)+B_e e(k)$$

$$y(k)=Cx(k)$$

where x is the vector of metabolic state differentials, $u_\delta$ (U/hr) is the deviation in insulin delivery from the patient's steady state (basal) insulin delivery rate, A, Bu, Bd, Be are the state space matrices of the linear model, and y(k) represents BG deviation from the operating point, and the dependence on $\theta(k)$ is embedded within the state space matrices A, Bu, Bd, Be.

20. The method of claim 11, wherein said perturbations include meal profiles, physical activity, and sleep/awake periods.

21. The method of claim 11, wherein said net effect model provides a history of virtual system inputs that reconciles the patient's historical record of BG and historical record of insulin delivery.

22. The method of claim 21, wherein the patient's historical record of BG concentration, $\{BG(k)\}_{k \in day}$, and historical record of insulin delivery, $\{u(k)\}_{k \in day}$, the net effect that reconciles the historical information is the vector of virtual carbohydrate inputs $\{d_{n.e.}(k)\}_{k \in day}$ that minimizes the error function:

$$\text{dist}(\{BG(k)\}_{k \in day}\{BG_{model}(k)\}_{k \in day} | \{u(k)\}_{k \in day}, \{d_{n.e.}(k)\}_{k \in day}),$$

where dist measures the distance between two vectors of BG concentration given the fixed record of insulin delivery $\{u(k)\}_{k \in day}$ and the candidate net effect vector $\{d_{n.e.}(k)\}_{k \in day}$.

23. The method of claim 22, wherein the resulting optimal net effect vector, $\{d_{n.e.}(k)\}_{k \in day}$, optimally reconciles the BG and insulin data collected by the patient through a virtual carbohydrate signal, which captures all external influences on the patient as a single external disturbance signal measured in (mg/min).

24. The method of claim 23, wherein:
the net effect vector being positive corresponds to the patient actually eating, or it corresponds to a period of the day in which the patient is experiencing enhanced insulin sensitivity; and
the net effect vector being negative corresponds to the patient engaging in intense physical activity or exercise.

25. The method of claim 11, wherein:
the patient's physiological model parameters, $\{\theta(k)\}_{k \in day}$, include daily variability due to the patients circadian rhythm; and
the model updater includes a formula:

$$\theta := \theta + U(BG_{res}, NE_{res}; \theta),$$

where U is the recursive parameter update function, which is gradient-based, $BG_{res}$ is a vector of BG model prediction errors and $NE_{res}$ is a vector of errors between the computed net effect curve and the patient's record of actual behavioral inputs.

26. The method of claim 25, wherein the dynamic model is adjusted on multiple time scales, whereby parameter updates are computed daily based on BG residuals:

$$\theta := \theta + U_1(BG_{res}; \theta),$$

and updates based on net effect mismatch are computed on a longer time scale, such as every week or month:

$$\theta := \theta + U_2(NE_{res}; \theta).$$

27. The method of claim 11, further comprising providing a retroactive assessment of the patient's optimal rate of insulin delivery by:
computing, via said processor or said another processor, what the patient's optimal rate of insulin delivery would have been over a predetermined period of historical time given that the disturbances to the system are exactly the historical of net effect curves computed for the patient over that interval of time, wherein for each history of net effect curves there is a corresponding history of insulin delivery rates that account for meals, exercise, and corrections for each day in the considered interval of time;
mapping, via said processor or said another processor, between the net effect vector for a given day and the model-based response of an optimal controller, wherein these vectors of optimal responses are collected and analyzed, and presented to the patient or user for a day-by-day review of insulin treatment;
extracting, via said processor or said another processor, features from the optimal responses that correspond to important but random events by subtracting discrete amounts of insulin associated with meals or accounting for discrete insulin deficits associated with temporary basal rates around exercise, whereby the remaining schedule of insulin delivery corresponds to a representation of the patient's optimal basal pattern each day in the historical record; and
identifying, via said processor or said another processor, consistency in the retroactively computed optimal basal rates, such optimal basal rates in a plurality of duration segments representing the patient's treatment duration; and
said method further comprising:
providing, via said processor or said another processor, to the patient or user the median level of basal insulin that would have been applied in each segment, wherein the patient or user uses this information to (i) decide upon on reduced temporary basal rates before meals and/or following exercise in the future or (ii) adjust the patient's long-term basal rate profile.

28. The method of claim 11, further comprising providing, via said processor or said another processor, an on-demand adaptive correction of insulin advice model, the model comprising:

an algorithm to include the following computations:
retrospective detecting for meal and exercise activities;
stochastic modeling to provide a description about the timing and content of meals and exercise; and
providing insulin correction advice to a patient or user that would be in response to a patient and user request.

29. The method of claim 28, wherein:
said retrospective detection for meal and exercise activities includes the algorithm for reconciling current history of said patient net effect curves with the historical record of patient-acknowledged meals and exercise events to produce a validated record of patient behaviors, wherein the reconciling includes identifying discrepancies between (i) the net effect curves computed from the available BG and insulin data for the patient and (ii) the meal and exercise events that are acknowledged by the patient or user through the systems user interface; and
said method comprises:
providing, via said processor or said another processor, suggestions from said discrepancies, wherein suggestions are communicated to patient or user; and
receiving, via said processor or said another processor, any responses resultant from the user or the patient to form the final, validated record of patient activities.

30. The method of claim 29, wherein:
said stochastic modeling includes the algorithm for receiving said final, validated record of patient activities and stochastically modeling to represent the timing and content of meals and exercise of the patient's behavior.

31. The method of claim 30, wherein:
said insulin correction includes the algorithm for monitoring the patient's status and to provide insulin correction advice in the moment the patient or user asks for it, based on (i) the stochastic modeling for upcoming behavioral disturbances and (ii) the current dynamic model of the patient's metabolic system that allows for the prediction of the impact of various alternative correction insulin amounts.

32. A system for treating a patient with insulin, the patient suffering from type 1 diabetes mellitus (T1DM), by providing a posterior assessment of a risk of hypoglycemia in the patient, the system comprising:
an insulin delivery device; and
a retroactive risk-based safety module having a processor configured to:
receive historical data including a patient's absolute blood glucose (BG) levels, BG variability, insulin delivery, and activities;
compute, via kernel density estimates of BG time series from the historical data, a statistic, $R_{hypo}(\text{record})$, that is representative of the risk of hypoglycemia associated with the posterior probability of hypoglycemia, $P(E_{hypo}|\text{record})$, where $E_{hypo}$ denotes the event of hypoglycemia in the next day and record refers to the patient's historical BG, insulin delivery, and activities record;
compare the historical insulin delivery data with the $R_{hypo}(\text{record})$ associated with the $P(E_{hypo}|\text{record})$; and
receive real-time BG and real-time insulin delivery data and adjust a basal rate profile for the patient based on the comparison so as to ameliorate risk of entering hypoglycemia;
calculate a correction bolus based on the adjusted basal rate profile; and
delivering, via the insulin delivery device, insulin in accordance with the correction bolus calculation.

33. The system of claim 32, wherein the absolute BG levels and the BG variability are data derived from a continuous glucose monitoring (CGM) device and the insulin delivery is data obtained from an insulin pump device.

34. The system of claim 32, wherein the absolute BG levels and the BG variability are data derived from a continuous glucose monitoring (CGM) device and the insulin delivery is data obtained from a manual insulin injection device.

35. The system of claim 32, wherein the absolute BG levels and the BG variability are data derived from a self-monitoring blood glucose (SMBG) device and the insulin delivery is data obtained from an insulin pump device.

36. The system of claim 32, wherein the absolute BG levels and the BG variability are data derived from a self-monitoring blood glucose (SMBG) device and the insulin delivery is data obtained from a manual insulin injection device.

37. The system of claim 32, further comprising:
a continuous glucose monitoring (CGM) device, wherein the absolute BG levels and the BG variability are data derived from said CGM device; and
an insulin pump device, wherein the insulin delivery are data obtained from said insulin pump device.

38. The system of claim 32, further comprising:
a continuous glucose monitoring (CGM) device, wherein the absolute BG levels and the BG variability are data derived from said CGM device; and
a manual insulin injection device, wherein the insulin delivery are data obtained from said manual insulin injection device.

39. The system of claim 32, further comprising:
a self-monitoring blood glucose (SMBG) device, wherein the absolute BG levels and the BG variability are data derived from said SMBG device; and/or
an insulin pump device, wherein the insulin delivery are data obtained from said insulin pump device.

40. The system of claim 32, further comprising:
a self-monitoring blood glucose (SMBG) device, wherein the absolute BG levels and the BG variability are data derived from said SMBG device; and/or
a manual insulin injection device, wherein the insulin delivery are data obtained from said manual insulin injection device.

41. A system for treating a patient by using retroactive analysis to provide a safe level of insulin dosage for the patient, the patient suffering from type 1 diabetes mellitus (T1DM), the system comprising:
an insulin delivery device; and
a retroactive risk-based safety module having a processor to:
receive a historical record of blood glucose (BG) levels and insulin delivery for a patient;
determine a risk of hypoglycemia for patient activities using a symmetrization function;
determine an attenuation factor that acts as a threshold when delivering insulin;
receive real-time BG and activity data and adjust a basal rate profile for the patient to incorporate the attenuation factor so as to ameliorate risk of entering hypoglycemia, wherein adjusting the basal rate profile involves reducing temporary basal rates before meals and/or following exercise;

calculate a correction bolus based on the adjusted basal rate profile; and deliver, via the insulin delivery device, insulin in accordance with the correction bolus calculation.

42. The system of claim 41, wherein the insulin delivery are data obtained from an insulin pump device.

43. The system of claim 41, wherein the insulin delivery are data obtained from a manual insulin injection device.

44. The system of claim 41, further comprising:
an insulin pump device, wherein the insulin delivery are data obtained from said insulin pump device.

45. The system of claim 41, further comprising:
a manual insulin injection device, wherein the insulin delivery are data obtained from said manual insulin injection device.

46. The system of claim 41, wherein the attenuation factor is computed as follows:

$$\phi(R(t,\tau)) = \frac{1}{1 + k_{patient} R(t,\tau)}$$

where $R(t, \tau)$ is a measure of the risk of hypoglycemia between time t and t+τ based on the historical record of BG and insulin data up to time t, based on the BG symmetrization of function and kpatient is a patient-specific aggressiveness factor.

47. A system for treating a patient with insulin, the patient suffering from type 1 diabetes mellitus (T1DM), by providing a net effect based patient adaptive model, the system comprising:
a net effect estimator module having a processor to compute:
a dynamic model of the patient's metabolic system, wherein said dynamic model includes descriptive parameters of an individual physiology of the model patient; and
a corresponding inferred history of a behavioral net effect model that explains the glucose variability in the historical record through the dynamic model, wherein said net effect model includes a mathematical representation of perturbations of the model patient; and
a model updater module having a processor to compute:
an update of the patient's physiological parameters based on both (i) the ability of the dynamic model to predict future blood glucose (BG) based on known inputs and (ii) the ability of the model to produce net effect curves that are consistent with the patient's record of the perturbations; and
estimate the patient's current metabolic system using the updated physiological parameters;
an insulin delivery device configured to:
deliver insulin to the patient based on a patient's metabolic system;
adjust a basal rate profile for the patient in accordance with said patient's estimated current metabolic system;
calculate a correction bolus based on the adjusted basal rate profile; and
deliver insulin in accordance with the correction bolus calculation.

48. The system of claim 47, wherein said descriptive parameters include a representation of the dynamic relationship between oral carbs d (g/min), physical activity e (cal/min), subcutaneous insulin u (U/hr), and the model patient's metabolic state vector x whose elements include glucose and insulin concentrations (mg/dl) in various compartments of the body and carbohydrate mass (mg) in the gut.

49. The system of claim 48, wherein the glucose concentration (mg/dl) is data derived from a continuous glucose monitoring (CGM) device and the subcutaneous insulin u and the insulin concentration (mg/dl) is data obtained from an insulin pump device.

50. The system of claim 48, wherein the glucose concentration (mg/dl) is data derived from a continuous glucose monitoring (CGM) device and the subcutaneous insulin u and the insulin concentration (mg/dl) is data obtained from a manual insulin injection device.

51. The system of claim 48, wherein the glucose concentration (mg/dl) is data derived from a self-monitoring blood glucose (SMBG) device and the subcutaneous insulin u and the insulin concentration (mg/dl) is data obtained from an insulin pump device.

52. The system of claim 48, wherein the glucose concentration (mg/dl) is data derived from a self-monitoring blood glucose (SMBG) device and the subcutaneous insulin u and the insulin concentration (mg/dl) is data obtained from a manual insulin injection.

53. The system of claim 48, further comprising:
a continuous glucose monitoring (CGM) device, wherein the glucose concentration (mg/dl) is data derived from said CGM device; and
an insulin pump, wherein the subcutaneous insulin u and the insulin concentration (mg/dl) are data obtained from an insulin pump device.

54. The system of claim 48, further comprising:
a self-monitoring blood glucose (SMBG) device, wherein the glucose concentration (mg/dl) is data derived from said SMBG device; and
an insulin pump device or an insulin injection device, wherein the subcutaneous insulin u and the insulin concentration (mg/dl) are data obtained from said insulin pump device or said insulin injection device.

55. The system of claim 48, wherein relationship said descriptive parameters are described as a set of discrete-time nonlinear difference equations:

$$x(k+1)=F(x(k),u(k),d(k),e(k);\theta(k))$$

$$BG_{model}(k)=G(X(k),u(k),d(k),e(k);\theta(k))$$

where F and G are nonlinear system equations and θ(k) is a vector of parameter values that are characteristic of the patient, such as body weight, volumes of distribution in various compartments, various time constant that describe the rates of absorption and clearance between various compartments, some of which are prone to varying as a function of time k.

56. The system of claim 48, wherein relationship of said of descriptive parameters is described as a set of continuous-time nonlinear differential equations:

$$\dot{x}(t)=F(x(t),u(t),d(t),e(t);\theta(t))$$

$$BG_{model}(t)=G(x(t),u(t),d(t),e(t);\theta(t)).$$

57. The system of claim 56, wherein nonlinear representation is linearized around an operating point to yield a linear dynamic model:

$$x(k+1)=Ax(k)+B_u u_\delta(k)+B_d d(k)+B_e e(k)$$

$$y(k)=Cx(k)$$

where x is the vector of metabolic state differentials, $u_\delta$ (U/hr) is the deviation in insulin delivery from the patient's steady state (basal) insulin delivery rate, A, $B_u$, $B_d$, $B_e$ are the state space matrices of the linear model, and y(k) represents BG deviation away from the operating point, and the dependence on θ(k) is embedded within the state space matrices A, $B_u$, $B_d$, $B_e$.

58. The system of claim 47, wherein said perturbations include meal profiles, physical activity, and sleep/awake periods.

59. The system of claim 47, wherein said net effect model provides a history of virtual system inputs that reconciles the patient's historical record of BG and historical record of insulin delivery.

60. The system of claim 59, wherein the patient's historical record of BG concentration, $\{BG(k)\}_{k \in day}$, and historical record of insulin delivery, $\{u(k)\}_{k \in day}$, the net effect that reconciles the historical information is the vector of virtual carbohydrate inputs $\{d_{n.e.}(k)\}_{k \in day}$, that minimizes the error function:

$$\text{dist}(\{BG(k)\}_{k \in day}, \{BG_{model}(k)\}_{k \in day} | \{u(k)\}_{k \in day}, \{d_{n.e.}(k)\}_{k \in day}),$$

where dist measures the distance between two vectors of BG concentration given the fixed record of insulin delivery $\{u(k)\}_{k \in day}$ and the candidate net effect vector $\{d_{n.e.}(k)\}_{k \in da}$.

61. The system of claim 60, wherein the resulting optimal net effect vector, $\{d_{n.e.}(k)\}_{k \in da}$, optimally reconciles the BG and insulin data collected by the patient through a virtual carbohydrate signal, which captures all external influences on the patient as a single external disturbance signal measured in (mg/min).

62. The system of claim 61, wherein:
the net effect curve being positive corresponds to the patient actually eating, or to a period of the day in which the patient is experiencing enhanced insulin sensitivity; and
the net effect curve being negative corresponds to the patient engaging in intense physical activity or exercise.

63. The system of claim 47, wherein:
the patient's physiological model parameters, $\{\theta(k)\}_{k \in day}$, include daily variability due to the patients circadian rhythm; and
the processor of the model updater module is configured to compute the following:

$$\theta := \theta + U(BG_{res}, NE_{res}; \theta),$$

where u is the recursive parameter update function, which is gradient-based, $BG_{recs}$ is a vector of BG model prediction errors and $NE_{res}$ is a vector of errors between the computed net effect curve and the patient's record of actual behavioral inputs.

64. The system of claim 63, wherein the dynamic model is adjusted on multiple time scales, whereby parameter updates are computed daily based on BG residuals:

$$\theta := \theta + U_1(BG_{res}; \theta),$$

and updates based on net effect mismatch are computed on a longer time scale:

$$\theta := \theta + U_2(NE_{res}; \theta).$$

65. The system of claim 47, further configured to provide a retroactive assessment of the patient's optimal rate of insulin delivery, wherein said system comprises:
a retrospective optimal control analyzer module having a processor configured to:
retroactively compute what the patient's optimal rate of insulin delivery would have been over a predetermined period of historical time given that the disturbances to the system are exactly the historical of net effect curves computed for the patient over that interval of time, wherein for each history of net effect curves there is a corresponding history of insulin delivery rates that account for meals, exercise, and corrections for each day in the considered interval of time; and
map between the net effect curve for a given day and the model-based response of an optimal controller, wherein these vectors of optimal responses are collected and analyzed, and presented to the patient or user for a day-by-day review of insulin treatment;
a retro-optimal basal rate extractor module having a processor configured to:
extract features from the optimal responses that correspond to important but random events by subtracting discrete amounts of insulin associated with meals or accounting for discrete insulin deficits associated with temporary basal rates around exercise, whereby the remaining schedule of insulin delivery corresponds to a representation of the patient's optimal basal pattern each day in the historical record; and
identify consistency in the retroactively computed optimal basal rates, such optimal basal rates in a plurality of duration segments representing the patient's treatment duration; and
said system being configured to provide an output to the patient or user the median level of basal insulin that would have been applied in each segment, wherein the patient or user uses this information to (i) decide upon on reduced temporary basal rates before meals and/or following exercise in the future or (ii) adjust the patient's long-term basal rate profile.

66. The system of claim 47, further configured to provide an on-demand adaptive correction of insulin advice model, said system comprises:
a retrospective meal and exercise detector module having a processor to provide retrospective detecting for meal and exercise activities;
a meal and exercise stochastic modeler module having a processor to provide stochastic modeling to provide a description about the timing and content of meals and exercise; and
a correction bolus advisor module having a processor to provide and output insulin correction advice to a patient or user that would be in response to a patient and user request.

67. The system of claim 66, wherein:
said retrospective detection for meal and exercise activities includes the algorithm for reconciling current history of said patient net effect curves with the historical record of patient-acknowledged meals and exercise events to produce a validated record of patient behaviors, wherein the reconciling includes identifying discrepancies between (i) the net effect curves computed from the available BG and insulin data for the patient and (ii) the meal and exercise events that are acknowledged by the patient or user through the systems user interface; and
said system configured to comprise:
an output module to provide suggestions from said discrepancies, wherein suggestions are communicated to patient or user; and
an input module to receive any responses resultant from user or patient to form the final, validated record of patient activities.

68. The system of claim 67, wherein:
said processor of said stochastic modeling module being configured for receiving said final, validated record of patient activities and stochastically modeling to represent the timing and content of meals and exercise of the patient's behavior.

69. The system of claim 68, wherein:
said processor of said correction bolus advisor module being configured for monitoring the patient's status and to provide insulin correction advice output in the moment the patient or user asks for it, based on (i) the stochastic modeling for upcoming behavioral disturbances and (ii) the current dynamic model of the patient's metabolic system that allows for the prediction of the impact of various alternative correction insulin amounts.

70. A non-transitory computer readable medium containing program instructions for treating a patient with insulin, the patient suffering from type 1 diabetes mellitus (T1DM), by providing a posterior assessment of a risk of hypoglycemia in the patient, wherein execution of the program instructions by one or more processors of a computer system causes the one or more processors to:
receive historical data including a patient's absolute blood glucose (BG) levels, BG variability, insulin delivery, and activities;
compute, via kernel density estimates of BG time series from the historical data, a statistic, $R_{hypo}$(record), that is representative of the risk of hypoglycemia associated with the posterior probability of hypoglycemia, $P(E_{hypo}|record)$, where $E_{hypo}$ denotes the event of hypoglycemia in the next day and record refers to the patient's historical BG, insulin delivery, and activities record;
compare the historical insulin delivery data with the $R_{hypo}$(record) associated with the $P(E_{hypo}|record)$;
receive real-time BG and real-time insulin delivery data and adjust a basal rate profile for the patient based on the comparison so as to ameliorate risk of entering hypoglycemia;
calculate a correction bolus based on the adjusted basal rate profile; and
delivering insulin with an insulin delivery device in accordance with the correction bolus calculation.

71. The non-transitory computer readable medium of claim 70, wherein the absolute BG levels and the BG variability are data derived from a continuous glucose monitoring (CGM) device and the insulin delivery are data obtained from an insulin pump device.

72. The non-transitory computer readable medium of claim 70, wherein the absolute BG levels and the BG variability are data derived from a continuous glucose monitoring (CGM) device and the insulin delivery are data obtained from a manual insulin injection device.

73. The non-transitory computer readable medium of claim 70, wherein the absolute BG levels and the BG variability are data derived from a self-monitoring blood glucose (SMBG) device and/or the insulin delivery are data obtained from an insulin pump device.

74. The non-transitory computer readable medium of claim 70, wherein the absolute BG levels and the BG variability are data derived from a self-monitoring blood glucose (SMBG) device and/or the insulin delivery are data obtained from a manual insulin injection device.

75. A non-transitory computer readable medium containing program instructions for treating a patient with insulin, the patient suffering from type 1 diabetes mellitus (T1DM), by using retroactive analysis to provide a safe level of insulin for the patient, wherein execution of the program instructions by one or more processors of a computer system causes the one or more processors to:
receive a historical record of blood glucose (BG) levels and insulin delivery for a patient;
determine a risk of hypoglycemia for patient activities using a symmetrization function;
determine an attenuation factor that acts as a threshold when delivering insulin;
receive real-time BG and activity data and adjust a basal rate profile for the patient to incorporate the attenuation factor so as to ameliorate risk of entering hypoglycemia, wherein adjusting the basal rate profile involves reducing temporary basal rates before meals and/or following exercise;
calculate a correction bolus based on the adjusted basal rate profile; and
deliver insulin with an insulin delivery device in accordance with the correction bolus calculation.

76. The non-transitory computer readable medium of claim 75, wherein the record of the insulin delivery is data obtained from an insulin pump device.

77. The non-transitory computer readable medium of claim 75, wherein the record of the insulin delivery is data obtained from a manual insulin injection device.

78. The non-transitory computer readable medium of claim 75, wherein the attenuation factor is computed as follows:

$$\phi(R(t, \tau)) = \frac{1}{1 + k_{patient} R(t, \tau)}$$

where $R(t, \tau)$ is a measure of the risk of hypoglycemia between time t and t+τ based on the historical record of BG and insulin data up to time t, based on the BG symmetrization of function and kpatient is a patient-specific aggressiveness factor.

79. A non-transitory computer readable medium containing program instructions for treating a patient with insulin, the patient suffering from type 1 diabetes mellitus (T1DM), by providing a net effect based patient adaptive model, wherein execution of the program instructions by one or more processors of a computer system causes the one or more processors to:
cause an insulin delivery device to deliver insulin to the patient based on a patient's metabolic system;
compute a dynamic model of the patient's metabolic system, wherein said dynamic model includes descriptive parameters of an individual physiology;
compute a corresponding inferred history of a behavioral net effect model that explains the glucose variability in the historical record through the dynamic model, wherein said net effect model includes a mathematical representation of perturbations;
compute an update of the patient's physiological parameters based on (i) the ability of the dynamic model to predict future blood glucose (BG) based on known inputs and (ii) the ability of the model to produce net effect curves that are consistent with the patient's record of perturbations;
estimate the patient's current metabolic system using the updated physiological parameters;
adjust a basal rate profile for the patient in accordance with said patient's estimated current metabolic system;

calculate a correction bolus based on the adjusted basal rate profile; and deliver insulin with the insulin delivery device in accordance with the correction bolus calculation.

80. The non-transitory computer readable medium of claim 79, wherein said descriptive parameters include a representation of the dynamic relationship between oral carbs d (g/min), physical activity e (cal/min), subcutaneous insulin u (U/hr), and the model patient's metabolic state vector x whose elements include glucose and insulin concentrations (mg/dl) in various compartments of the body and carbohydrate mass (mg) in the gut.

81. The non-transitory computer readable medium of claim 80, wherein the glucose concentration (mg/dl) is data derived from a continuous glucose monitoring (CGM) device and the subcutaneous insulin u and the insulin concentration (mg/dl) is data obtained from an insulin pump device.

82. The non-transitory computer readable medium of claim 80, wherein the glucose concentration (mg/dl) is data derived from a continuous glucose monitoring (CGM) device and the subcutaneous insulin u and the insulin concentration (mg/dl) is data obtained from a manual insulin injection device.

83. The non-transitory computer readable medium of claim 80, wherein the glucose concentration (mg/dl) is data derived from a self-monitoring blood glucose (SMBG) device and/or the subcutaneous insulin u and the insulin concentration (mg/dl) is data obtained from an insulin pump device.

84. The non-transitory computer readable medium of claim 80, wherein the glucose concentration (mg/dl) is data derived from a self-monitoring blood glucose (SMBG) device and/or the subcutaneous insulin u and the insulin concentration (mg/dl) is data obtained from a manual insulin injection device.

85. The non-transitory computer readable medium of claim 80, wherein relationship said descriptive parameters is described as a set of discrete-time nonlinear difference equations:

$$x(k+1)=F(x(k),u(k),d(k),e(k);\theta(k))$$

$$BG_{model}(k)=G(X(k),u(k),d(k),e(k);\theta(k))$$

where F and G are nonlinear system equations and $\theta(k)$ is a vector of parameter values that are characteristic of the patient, including body weight, volumes of distribution in various compartments, various time constant that describe the rates of absorption and clearance between various compartments, at least some of which parameter values are prone to varying as a function of time k.

86. The non-transitory computer readable medium of claim 80, wherein relationship of said of descriptive parameters are described as a set of continuous-time nonlinear differential equations:

$$\dot{x}(t)=F(x(t),u(t),d(t),e(t);\theta(t))$$

$$BG_{model}(t)=G(x(t),u(t),d(t),e(t);\theta(t)).$$

87. The non-transitory computer readable medium of claim 86, wherein nonlinear representation is linearized around an operating point to yield a linear dynamic model:

$$x(k+1)=Ax(k)+B_u u_\delta(k)+B_d d(k)+B_e e(k)$$

$$y(k)=Cx(k)$$

where x is a vector of metabolic state differentials $u_\delta$ (U/hr) is deviation in insulin delivery from the patient's steady state insulin delivery rate, A, Bu, Bd, Be are state space matrices of the linear model, and y(k) represents BG deviation away from the operating point, and the dependence on $\theta(k)$ is embedded within the state space matrices A, Bu, Bd, Be.

88. The non-transitory computer readable medium of claim 79, wherein said perturbations include meal profiles, physical activity, and sleep/awake periods.

89. The non-transitory computer readable medium of claim 79, wherein said net effect model provides a history of virtual system inputs that reconciles the patient's historical record of BG and historical record of insulin delivery.

90. The non-transitory computer readable medium of claim 89, wherein the patient's historical record of BG concentration, $\{BG_{model}(k)\}_{k \in day}$, and historical record of insulin delivery, $\{u(k)\}_{k \in day}$, the net effect that reconciles the historical information is the vector of virtual carbohydrate inputs $\{d_{n.e.}(k)\}_{k \in day}$, that minimizes the error function:

$$\text{dist}(\{BG(k)\}_{k \in day}, \{BG_{model}(k)_{k \in day}|\{u(k)_{k \in day}, \{d_{n.e.}(k)\}_{k \in day}),$$

where dist measures the distance between two vectors of BG concentration given the fixed record of insulin delivery $\{u(k)\}_{k \in day}$ and the candidate net effect vector $\{d_{n.e.}(k)\}_{k \in day}$.

91. The non-transitory computer readable medium of claim 90, wherein the resulting optimal net effect vector, $\{d_{n.e.}(k)\}_{k \in day}$, optimally reconciles the BG and insulin data collected by the patient through a virtual carbohydrate signal, which captures all external influences on the patient as a single external disturbance signal measured in (mg/min).

92. The non-transitory computer readable medium of claim 91, wherein:

the net effect curve being positive corresponds to the patient actually eating, or to a period of the day in which the patient is experiencing enhanced insulin sensitivity; and the net effect curve being negative corresponds to the patient engaging in significant physical activity or exercise.

93. The non-transitory computer readable medium of claim 79, wherein:

the patient's physiological model parameters, $\{\theta(k)\}_{k \in day}$, includes daily variability due to the patients circadian rhythm; and the model updater includes the following formula:

$$\theta:=\theta+U(BG_{res},NE_{res};\theta),$$

where U is the recursive parameter update function, which is gradient-based, $BG_{res}$ is a vector of BG model prediction errors and $NE_{res}$ is a vector of errors between the computed net effect curve and the patient's record of actual behavioral inputs.

94. The non-transitory computer readable medium of claim 93, wherein the dynamic model is adjusted on multiple time scales, whereby parameter updates are computed daily based on BG residuals:

$$\theta:=\theta+U_1(BG_{res};\theta),$$

and updates based on net effect mismatch are computed on a longer time scale:

$$\theta:=\theta+U_2(NE_{res};\theta).$$

95. The non-transitory computer readable medium of claim 79, further comprising providing a retroactive assessment of the patient's optimal rate of insulin delivery, wherein execution of the program instructions by one or more processors of a computer system causes the one or more processors to:

compute what the patient's optimal rate of insulin delivery would have been over a predetermined period of historical time given that the disturbances to the system are exactly the historical of net effect curves computed for the patient over that interval of time, wherein for each history of net effect curves there is a corresponding history of insulin delivery rates that account for meals, exercise, and corrections for each day in the considered interval of time;

map between the net effect curve for a given day and the model-based response of an optimal controller, wherein these vectors of optimal responses are collected and analyzed, and presented to the patient or user for a day-by-day review of insulin treatment;

extract features from the optimal responses that correspond to important but random events by subtracting discrete amounts of insulin associated with meals or accounting for discrete insulin deficits associated with temporary basal rates around exercise, whereby the remaining schedule of insulin delivery corresponds to a representation of the patient's optimal basal pattern each day in the historical record;

identify consistency in the retroactively computed optimal basal rates, such optimal basal rates in a plurality of duration segments representing the patient's treatment duration; and output the median level of basal insulin that would have been applied in each segment, wherein the patient or user uses this information to (i) decide upon on reduced temporary basal rates before meals and/or following exercise in the future or (ii) adjust the patient's long-term basal rate profile.

96. The non-transitory computer readable medium of claim 79, further comprising providing an on-demand adaptive correction of insulin advice model, wherein execution of the program instructions by one or more processors of a computer system causes the one or more processors to:

retrospectively detect meal and exercise activities;

perform stochastic modeling to provide a description about the timing and content of meals and exercise; and provide insulin correction advice that would be in response to a request.

97. The non-transitory computer readable medium of claim 96, wherein:

said retrospective detection for meal and exercise activities includes an algorithm for reconciling current history of said patient net effect curves with the historical record of patient-acknowledged meals and exercise events to produce a validated record of patient behaviors, wherein the reconciling includes identifying discrepancies between (i) the net effect curves computed from the available BG and insulin data for the patient and (ii) the meal and exercise events that are acknowledged by the patient or user through the systems user interface; and wherein execution of the program instructions by one or more processors of a computer system causes the one or more processors to:

provide suggestions from said discrepancies, wherein suggestions are communicated to patient or user; and receive any resultant responses to form a final, validated record of patient activities.

98. The non-transitory computer readable medium of claim 97, wherein:

said stochastic modeling includes the algorithm for receiving said final, validated record of patient activities and stochastically modeling to represent the timing and content of meals and exercise of the patient's behavior.

99. The non-transitory computer readable medium of claim 98, wherein:

said insulin correction includes an algorithm for monitoring the patient's status and to provide insulin correction advice in the moment it is requested, based on (i) the stochastic modeling for upcoming behavioral disturbances and (ii) the current dynamic model of the patient's metabolic system that allows for the prediction of the impact of various alternative correction insulin amounts.

* * * * *